US008486948B2

(12) United States Patent
Pouzet et al.

(10) Patent No.: US 8,486,948 B2
(45) Date of Patent: Jul. 16, 2013

(54) PIPERAZINODIHYDROTHIENOPYRIMIDINE DERIVATIVES

(75) Inventors: Pascale Pouzet, Biberach (DE); Christoph Hoenke, Ingelheim am Rhein (DE); Peter Nickolaus, Warthausen (DE); Rolf Goeggel, Ulm (DE); Thomas Fox, Biberach (DE); Dennis Fiegen, Biberach (DE); Klaus Klinder, Oggelshausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 327 days.

(21) Appl. No.: 12/738,425

(22) PCT Filed: Oct. 16, 2008

(86) PCT No.: PCT/EP2008/063970
§ 371 (c)(1),
(2), (4) Date: Sep. 3, 2010

(87) PCT Pub. No.: WO2009/050236
PCT Pub. Date: Apr. 23, 2009

(65) Prior Publication Data
US 2011/0046096 A1    Feb. 24, 2011

(30) Foreign Application Priority Data
Oct. 19, 2007 (EP) .................... 07118906

(51) Int. Cl.
*C07D 495/04* (2006.01)
*A61K 31/519* (2006.01)
*A61P 25/28* (2006.01)
*A61P 25/24* (2006.01)
*A61P 25/22* (2006.01)
*A61P 29/00* (2006.01)
*A61P 11/06* (2006.01)

(52) U.S. Cl.
USPC ................... 514/252.16; 544/278

(58) Field of Classification Search
USPC ..................... 544/278; 514/260.1
See application file for complete search history.

(56) References Cited

U.S. PATENT DOCUMENTS
2008/0096882 A1    4/2008 Pouzet et al.

FOREIGN PATENT DOCUMENTS
| CA | 2605161 A1 | 10/2006 |
| CA | 2647243 A1 | 10/2007 |
| EP | 1847543 A1 | 10/2007 |
| WO | 2006111549 A1 | 10/2006 |

OTHER PUBLICATIONS

DiGirolamo et al. (Br. J. Pharmacol., 2003, 139(6), pp. 1164-1170).*
Chakraborti et al.; 3D-QSAR Studies on Thieno[3,2-d]pyrimidines as Phosphodiesterase IV Inhibitors; Bioorganic & Medicinal Chemistry Letters; 2003; vol. 13; pp. 1403-1408.
Odingo; Inhibitors of PDE4: a review of recent patent literature; Expert Opinion; Jan. 1, 2005; vol. 15; No. 7; pp. 773-787.
International Search Report, Form PCT/ISA/210, for corresponding PCT/EP2008/063970; date of mailing: Apr. 1, 2009.

* cited by examiner

*Primary Examiner* — Susanna Moore
(74) *Attorney, Agent, or Firm* — Michael P. Morris; Wendy A. Petka; Timothy X. Witkowski

(57) ABSTRACT

The invention relates to the novel dihydrothienopyrimidine sulfoxides of formula (I) and to the pharmacologically acceptable salts thereof, wherein X represents SO or $SO_2$, preferably however SO, and wherein $R^3$, $R^4$, $R^{4'}$, $R^5$, $R^6$ and $R^7$ are defined as in claim 1. The invention also relates to pharmaceutical compositions containing said compounds. The novel dihydrothienopyrimidine sulfoxides are suitable for use in the treatment of respiratory or gastrointestinal disorders or diseases, inflammatory diseases of the joints, the skin or the eyes, diseases of the peripheral or central nervous system or cancers.

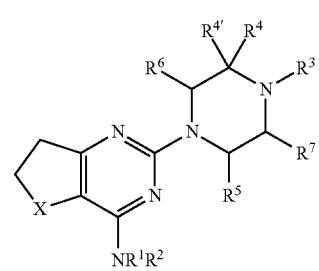

(1)

10 Claims, No Drawings

PIPERAZINODIHYDROTHIENOPYRIMIDINE DERIVATIVES

RELATED APPLICATIONS

This application is a 371 of International Application No. PCT/EP2008/063970, filed Oct. 16, 2008, which claims priority to European Patent Application No. 07118906.2, filed Oct. 19, 2007, the contents of which are incorporated herein by reference in their entirety.

The invention relates to new dihydrothienopyrimidinesulphoxides of formula 1, as well as pharmacologically acceptable salts, diastereomers, enantiomers, racemates, hydrates or solvates thereof,

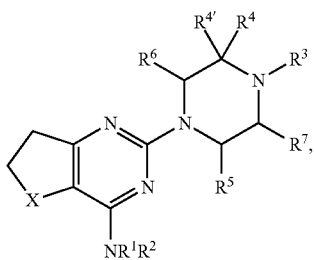

1 wherein X is SO or $SO_2$, but preferably SO, and wherein $R^3$, $R^4$, $R^{4'}$, $R^5$, $R^6$ and $R^7$ may have the meanings given in claim 1, as well as pharmaceutical compositions which contain these compounds.

These new dihydrothienopyrimidinesulphoxides are suitable for the treatment of respiratory or gastrointestinal complaints or diseases, inflammatory diseases of the joints, skin or eyes, diseases of the peripheral or central nervous system or cancers.

PRIOR ART

U.S. Pat. No. 3,318,881 and BE 663693 disclose the preparation of dihydrothieno[3,2-d]pyrimidines which have cardiovascular and sedative properties. WO 2006/111549 and EP06112779.1 (EP1847543) each disclose dihydrothienopyrimidinesulphoxides according to the above formula 1, except that $R^4$, $R^{4'}$, $R^5$, $R^6$, $R^7$ may only be hydrogen.

DESCRIPTION OF THE INVENTION

Surprisingly it has now been found that dihydrothienopyrimidinesulphoxides of formula 1, wherein the piperazine unit of formula 1 is modified beyond the $R^3$ group, i.e. either includes other substituents, is bridged by means of alkylene groups or is annelated with other rings, are particularly suitable for the treatment of inflammatory diseases and are superior to the corresponding dihydrothienopyrimidinesulphoxides from the prior art.

The present invention therefore relates to compounds of formula 1

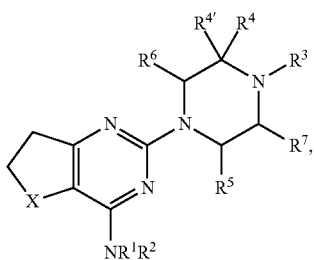

1 wherein
X is SO or $SO_2$,
$R^1$ is H, $C_{1-6}$-alkyl,
$R^2$ is H or a group selected from among $C_{1-10}$-alkyl and $C_{2-6}$-alkenyl, which may optionally be substituted by one or more groups selected from halogen and $C_{1-3}$-fluoroalkyl or which may optionally be substituted by one or more groups selected from among $OR^{2.1}$, $COOR^{2.1}$, $CONR^{2.2}R^{2.3}$, $SR^{2.1}$, $SO-R^{2.1}$, $SO_2-R^{2.1}$, $C_{6-10}$-aryl, a het, a hetaryl, a mono- or bicyclic $C_{3-10}$-cycloalkyl, $CH_2-NR^{2.2}R^{2.3}$ and $NR^{2.2}R^{2.3}$, which in turn may optionally be substituted by one or more groups selected from among OH, halogen, $OR^{2.1}$, oxo, $CF_3$, $CHF_2$, $CH_2F$, $C_{1-6}$-alkyl, $C_{1-6}$-alkanol, $C_{6-10}$-aryl, $COOR^{2.1}$, $CH_2-NR^{2.2}R^{2.3}$ and $NR^{2.2}R^{2.3}$,
wherein $R^{2.1}$ is H or a group selected from among $C_{1-6}$-alkyl, $C_{1-6}$-alkanol, $C_{1-3}$-fluoroalkyl, mono- or bicyclic $C_{3-10}$ cycloalkyl,
$C_{6-10}$-aryl-$C_{1-6}$-alkylene, hetaryl-$C_{1-6}$-alkylene,
het-$C_{1-6}$-alkylene, $C_{3-10}$-cycloalkyl-$C_{1-6}$-alkylene, a mono- or bicyclic $C_{6-10}$-aryl,
a hetaryl and a het, which may optionally be substituted by one or more groups selected from among OH, O—($C_{1-3}$-alkyl), halogen, $C_{1-6}$-alkyl and $C_{6-10}$-aryl,
wherein $R^{2.2}$ and $R^{2.3}$ independently of one another denote H or a group selected from among $C_{1-6}$-alkyl, mono- or bicyclic $C_{3-10}$-cycloalkyl, $C_{6-10}$-aryl-$C_{1-6}$-alkylene, hetaryl-$C_{1-6}$-alkylene, mono- or bicyclic $C_{6-10}$-aryl, a het a hetaryl, $CO-NH_2$, $CO-NH(CH_3)$, $CO-N(CH_3)_2$, $SO_2-(C_{1-2}$-alkyl), $CO-R^{2.1}$ and $COOR^{2.1}$,
which may optionally be substituted by one or more groups selected from among OH, halogen, $C_{1-6}$-alkyl, $C_{6-10}$-aryl and $COOR^{2.1}$,
wherein
het is a three- to eleven-membered, mono- or bicyclic, saturated or partially saturated, optionally annelated or optionally bridged heterocyclic group, which contains 1, 2, 3 or 4 heteroatoms independently selected from among N, S or O, and wherein
hetaryl is a five- to ten-membered, mono- or bicyclic, optionally annelated heteroaryl, which contains 1, 2, 3 or 4 heteroatoms independently selected from among N, S or O, and wherein
cycloalkyl may be saturated or partially saturated,
or
$R^2$ denotes a mono- or polycyclic $C_{3-10}$ cycloalkyl, which may optionally be mono- or poly-bridged via $C_{1-3}$-alkyl groups and which may optionally be substituted by a group selected from among branched or unbranched $C_{1-6}$-alkanol, $C_{1-3}$-fluoroalkyl, $C_{1-3}$-alkylene-$OR^{2.1}$, $OR^{2.1}$, $COOR^{2.1}$, $SO_2-NR^{2.2}R^{2.3}$, het, $C_{6-10}$-aryl, $C_{1-6}$-alkyl, $C_{6-10}$-aryl-$C_{1-6}$-alkylene, hetaryl-$C_{1-6}$-alkylene, mono- or bicyclic $C_{3-10}$ cycloalkyl and $NR^{2.2}R^{2.3}$, which may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$,
or
$R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2-NR^{2.2}R^{2.3}$, $C_{3-10}$-cycloalkyl, het, $C_{1-6}$-alkyl, $C_{1-3}$-fluoroalkyl, $C_{6-10}$-aryl-$C_{1-6}$-alkylene, het-$C_{1-6}$-alkylene, hetaryl-$C_{1-6}$-alkylene, $C_{6-10}$-aryl, $SO_2-CH_3$, $SO_2-CH_2CH_3$ and $SO_2-NR^{2.2}R^{2.3}$,
which in turn may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$,
or
$R^2$ denotes a group selected from among a het and a hetaryl, which in turn may optionally be substituted by one or more groups selected from among halogen, OH, oxo, CF$_3$, CHF$_2$ and CH$_2$F or by one or more groups selected from among OR$^{2.1}$, C$_{1-3}$-alkylene-OR$^{2.1}$, SR$^{2.1}$, SO—R$^{2.1}$, and SO$_2$—R$^{2.1}$ COOR$^{2.1}$, COR$^{2.1}$, C$_{1-6}$-alkanol, C$_{3-10}$-cycloalkyl, C$_{6-10}$-aryl, C$_{6-10}$-aryl-C$_{1-6}$-alkylene, hetaryl-C$_{1-6}$-alkylene, het, hetaryl, C$_{1-3}$-alkylene-OR$^{2.1}$ and NR$^{2.2}$R$^{2.3}$, which in turn may optionally be substituted by one or more groups selected from among OH, OR$^{2.1}$, oxo, halogen, CF$_3$, CHF$_2$, CH$_2$F, C$_{1-6}$-alkyl, C$_{6-10}$-aryl and NR$^{2.2}$R$^{2.3}$, or wherein NR$^1$R$^2$ together denotes a heterocyclic four- to seven-membered ring, which may optionally be bridged, which contains 1, 2 or 3 heteroatoms selected from among N, O and S and which may optionally be substituted by one or more groups selected from among OH, OR$^{2.1}$, C$_{1-3}$-alkylene-O$^{R.1}$, oxo, halogen, C$_{1-6}$-alkyl, C$_{6-10}$-aryl, COOR$^{2.1}$, CH$_2$—NR$^{2.2}$—COO—R$^{2.1}$, CH$_2$—NR$^{2.2}$—CO—R$^{2.1}$, CH$_2$—NR$^{2.2}$—CO—CH$_2$—NR$^{2.2}$R$^{2.3}$, CH$_2$—NR$^{2.2}$—SO$_2$—C$_{1-3}$-alkyl, CH$_2$—NR$^{2.2}$—SO$_2$—NR$^{2.2}$R$^{2.3}$, CH$_2$—NR$^{2.2}$—CO—NR$^{2.2}$R$^{2.3}$, CO—NR$^{2.2}$R$^{2.3}$, CH$_2$—NR$^{2.2}$R$^{2.3}$ and NR$^{2.2}$R$^{2.3}$, and wherein R$^3$ is a group selected from among a mono- or bicyclic C$_{6-10}$-aryl, a het and a hetaryl, which may optionally be substituted by one or more groups selected from among halogen, —C$_{1-3}$-alkyl, cyclopropyl, —C$_{1-3}$-fluoroalkyl, —C$_{1-3}$-alkylene-OR$^{2.1}$, —OH and —O—C$_{1-3}$-alkyl, and wherein R$^4$ denotes H, C$_{1-6}$-alkyl; F, C$_{1-3}$-fluoroalkyl, (C$_{1-6}$-alkylene)-OH, (C$_{1-6}$-alkylene)-OCH$_3$, (C$_{1-6}$-alkylene)-NH$_2$, (C$_{1-6}$-alkylene)-NH(C$_{1-3}$-alkyl) or (C$_{1-6}$-alkylene)-N(C$_{1-3}$-alkyl)$_2$, R$^{4'}$ denotes H or F or wherein R$^4$ and R$^{4'}$ together represent an oxo group, and wherein R$^5$, R$^6$ and R$^7$ independently of one another denote H, F, C$_{1-3}$-fluoroalkyl, C$_{1-6}$-alkylene-OH, C$_{1-5}$-alkylene-OCH$_3$, C$_{1-6}$-alkylene-NH$_2$, C$_{1-6}$-alkylene-NH(C$_{1-3}$-alkyl) and C$_{1-6}$-alkylene-N(C$_{1-3}$-alkyl)$_2$, or wherein R$^6$ and R$^7$ together form a bridge selected from among methylene, ethylene and propylene, which may optionally be substituted by a group selected from among —CH$_3$, —OH, —F, —CF$_3$, —CHF$_2$, —CH$_2$F, —NH$_2$, —NH(C$_{1-3}$-alkyl), —N(C$_{1-3}$-alkyl)$_2$ and O—(C$_{1-3}$-alkyl), or wherein R$^5$ and R$^6$ together form a bridge selected from among methylene, ethylene and propylene, which may optionally be substituted by a group selected from among CH$_3$, —OH, —F, —CF$_3$, —CHF$_2$, —CH$_2$F, —NH$_2$, —NH(C$_{1-3}$-alkyl), —N(C$_{1-3}$-alkyl)$_2$ and OCH$_3$, or wherein R$^3$ and R$^4$ together with the C— and the N atom of the piperazine form a saturated or partially unsaturated 5- or 6-membered heterocyclic group containing two or three, but at least two nitrogen atoms or wherein R$^3$, R$^4$ and R$^{4'}$ together with the C— and the N atom of the piperazine form an unsaturated or partially unsaturated, 5- or 6-membered heterocyclic group containing two or three, but at least two nitrogen atoms, wherein each of these saturated, unsaturated or partially unsaturated, 5- or 6-membered heterocycles may optionally be substituted by one, two or three groups selected from among oxo, OH, halogen, C$_{1-6}$-alkyl, cyclopropyl, C$_{1-3}$-fluoroalkyl, C$_{1-3}$-alkylene-OR$^{2.1}$, C$_{1-6}$-alkanol, COOR$^{2.1}$, C$_{6-10}$-aryl, C$_{1-3}$-alkylene-C$_{6-10}$-aryl, hetaryl, C$_{1-3}$-alkylene-hetaryl, het, CO-het, C$_{1-3}$-alkylene-het, —CO—N(C$_{1-3}$-alkyl)-het, —CO—NH-het, —CO—O—N(C$_{1-3}$-alkyl)-het, —CO—O—NH-het, —CO—N(C$_{1-3}$-alkyl)-het, —CO—NH-cycloalkyl, —CO—NH—C$_{3-7}$-cycloalkyl, —CO—O—N(C$_{1-3}$-alkyl)-C$_{3-7}$-cycloalkyl, —CO—O—NH—C$_{3-7}$-cycloalkyl, —CO—NH—(C$_{1-2}$-alkylene)hetaryl, —CO—N(C$_{1-3}$-alkyl)-(C$_{1-2}$-alkylene)-hetaryl, —CO—NH—CH(C$_{1-3}$-alkyl)-hetaryl, —CO—NH—C(C$_{1-3}$-alkyl)$_2$-hetaryl, —CO—N(cyclopropyl)-het and —CO—N(cyclopropyl)-hetaryl, which in turn may optionally be substituted by one or more groups selected from among OH, oxo, halogen, C$_{1-6}$-alkyl, C$_{1-3}$-fluoroalkyl, C$_{1-6}$-alkanol, and the pharmacologically acceptable salts, diastereomers, enantiomers, racemates, hydrates or solvates thereof.

In one aspect the present invention relates to the compounds of formula A

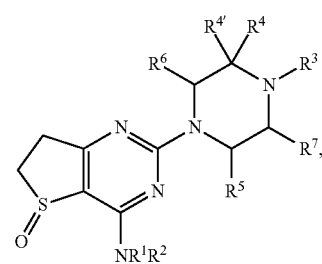

A but particularly to both the R-enantiomers according to formula A' and also the S-enantiomers according to formula A" with respect to the stereocentre at the sulphoxide sulphur atom of the compounds of formula 1,

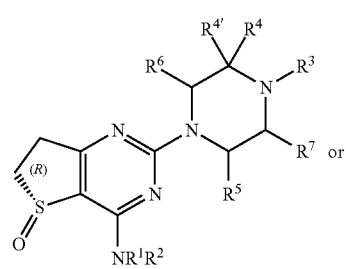

A'

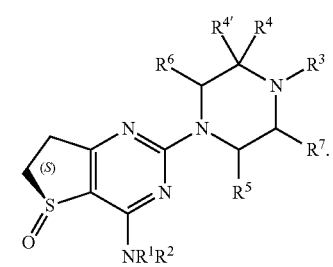

A"

Also preferred are the above-mentioned compounds of formula 1, wherein

X is SO or SO$_2$,

R$^1$ is H

R$^2$ is H or C$_{1-10}$-alkyl, which may optionally be substituted by one or more groups selected from halogen and C$_{1-3}$-fluoroalkyl or which may optionally be substituted by one or more groups selected from among $OR^{2.1}$, $COOR^{2.1}$, $CONR^{2.2}R^{2.3}$, $SR^{2.1}$, $SO—R^{2.1}$, $SO_2—R^{2.1}$, $C_{6-10}$-aryl, a het, a hetaryl, a mono- or bicyclic $C_{3-10}$-cycloalkyl, $CH_2—NR^{2.2}R^{2.3}$ and $NR^{2.2}R^{2.3}$, which in turn may optionally be substituted by one or more groups selected from among OH, halogen, $OR^{2.1}$, oxo, $CF_3$, $CHF_2$, $CH_2F$, $C_{1-6}$-alkyl, $C_{1-6}$-alkanol, $C_{6-10}$-aryl, $COOR^{2.1}$, $CH_2—NR^{2.2}R^{2.3}$ and $NR^{2.2}R^{2.3}$, wherein het is a three- to seven-membered, monocyclic, saturated or partially saturated heterocyclic group or a seven- to eleven-membered, bicyclic, saturated or partially saturated heterocyclic group, which contains 1, 2, 3 or 4 heteroatoms selected independently of one another from among N, S or O, and wherein hetaryl is a five- to six-membered, monocyclic, aromatic heteroaryl or a seven- to eleven-membered, bicyclic, aromatic heteroaryl, which contains in each case 1, 2, 3 or 4 heteroatoms selected independently of one another from among N, S or O, and wherein cycloalkyl may be saturated or partially saturated,
  wherein $R^{2.1}$, $R^{2.2}$ and $R^{2.3}$ are defined as in claim 1 or $R^2$ denotes a mono- or polycyclic $C_{3-10}$ cycloalkyl, which may optionally be mono- or poly-bridged via $C_{1-3}$-alkyl groups and which may optionally be substituted by a group selected from among branched or unbranched $C_{1-6}$-alkanol, $C_{1-3}$-alkylene-$OR^{2.1}$, $OR^{2.1}$, $C_{1-3}$-fluoroalkyl, $COOR^{2.1}$, $SO_2—NR^{2.2}R^{2.3}$, het, $C_{6-10}$-aryl, $C_{1-6}$-alkyl, $C_{6-10}$-aryl-$C_{1-6}$-alkylene, hetaryl-$C_{1-6}$-alkylene, mono- or bicyclic $C_{3-10}$ cycloalkyl and $NR^{2.2}R^{2.3}$, which may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$, or $R^2$ denotes a mono- or polycyclic $C_{6-10}$-aryl, which may optionally be substituted by OH, SH or halogen or by one or more groups selected from among $OR^{2.1}$, $COOR^{2.1}$, $NR^{2.2}R^{2.3}$, $CH_2—NR^{2.2}R^{2.3}$, $C_{3-10}$-cycloalkyl, het, $C_{1-6}$-alkyl, $C_{1-3}$-fluoroalkyl, $C_{6-10}$-aryl-$C_{1-6}$-alkylene, het-$C_{1-6}$-alkylene, hetaryl-$C_{1-6}$-alkylene, $C_{6-10}$-aryl, $SO_2—CH_3$, $SO_2—CH_2CH_3$ and $SO_2—NR^{2.2}R^{2.3}$, which in turn may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$, or $R^2$ denotes a group selected from among a het and a hetaryl, which in turn may optionally be substituted by one or more groups selected from among halogen, $CF_3$, $CHF_2$, $CH_2F$, OH and oxo or by one or more groups selected from among $OR^{2.1}$, $C_{1-3}$-alkylene-$OR^{2.1}$, $SR^{2.1}$, $SO—R^{2.1}$, $SO_2—R^{2.1}$, $COOR^{2.1}$, $COR^{2.1}$, $C_{1-6}$-alkanol, $C_{1-3}$-alkylene-$OR^{2.1}$, $C_{3-10}$-cycloalkyl, $C_{6-10}$-aryl, $C_{1-6}$-alkyl, $C_{6-10}$-aryl-$C_{1-6}$-alkylene, hetaryl-$C_{1-6}$-alkylene, het, hetaryl and $NR^{2.2}R^{2.3}$, which in turn may optionally be substituted by one or more groups selected from among OH, $OR^{2.1}$, oxo, halogen, $CF_3$, $CHF_2$, $CH_2F$, $C_{1-6}$-alkyl, $C_{6-10}$-aryl and $NR^{2.2}R^{2.3}$, and wherein $R^3$ denotes a group selected from among a mono- or bicyclic $C_{6-10}$-aryl, a het and a hetaryl, which may optionally be substituted by one or more groups selected from among halogen, —$C_{1-3}$-alkyl, cyclopropyl, —$C_{1-3}$-fluoroalkyl, —$C_{1-3}$-alkylene-$OR^{2.1}$, —OH and —O—$C_{1-3}$-alkyl and wherein $R^4$ denotes H, $C_{1-6}$-alkyl; F, $C_{1-3}$-fluoroalkyl, $C_{1-6}$-alkylene-OH, $C_{1-6}$-alkylene-$OCH_3$, $C_{1-6}$-alkylene-$NH_2$, $C_{1-6}$-alkylene-$NH(CH_3)$ or $C_{1-6}$-alkylene-$N(CH_3)_2$, $R^{4'}$ denotes H or F or wherein $R^4$ and $R^{4'}$ together represent an oxo group, and wherein $R^5$, $R^6$ and $R^7$ independently of one another denote H, $C_{1-6}$-alkyl; F, $C_{1-3}$-fluoroalkyl, $C_{1-6}$-alkylene-OH, $C_{1-6}$-alkylene-$OCH_3$, $C_{1-6}$-alkylene-$NH_2$, $C_{1-6}$-alkylene-$NH(CH_3)$ or $C_{1-6}$-alkylene-$N(CH_3)_2$, or wherein $R^6$ and $R^7$ together form a bridge selected from among methylene, ethylene and propylene, or wherein $R^5$ and $R^6$ together form a bridge selected from among methylene, ethylene and propylene, or wherein $R^3$, $R^4$ and $R^{4'}$ together with the C— and the N atom of the piperazine form an unsaturated or partially unsaturated, 5- or 6-membered heterocyclic group containing two or three, but at least two nitrogen atoms, wherein this heterocyclic group may optionally be substituted by one, two or three groups selected from among oxo, OH, halogen, $C_{1-6}$-alkyl, cyclopropyl, $C_{1-6}$-fluoroalkyl, $C_{1-3}$-alkylene-$OR^{2.1}$, $C_{1-6}$-alkanol, $COOR^{2.1}$, $C_{6-10}$-aryl, $C_{1-3}$-alkylene-$C_{6-10}$-aryl, hetaryl, $C_{1-3}$-alkylene-hetaryl, het, CO-het, $C_{1-3}$-alkylene-het, —CO—N($CH_3$)-het, —CO—NH-het, —CO—N($CH_3$)—$C_{3-7}$-cycloalkyl, —CO—NH—$C_{3-7}$-cycloalkyl, —CO—NH—$C_{1-2}$-alkylene-hetaryl, —CO—N($CH_3$)—$C_{1-2}$-alkylene-hetaryl, —CO—NH—CH($CH_3$)-hetaryl, —CO—NH—C($CH_3$)$_2$-hetaryl, —CO—N(cyclopropyl)-het and —CO—N(cyclopropyl)-hetaryl, which in turn may optionally be substituted by one or more groups selected from among OH, oxo, halogen, $C_{1-6}$-alkyl, $C_{1-3}$-fluoroalkyl, $C_{1-6}$-alkanol, and the pharmacologically acceptable salts, diastereomers, enantiomers, racemates, hydrates or solvates thereof.

Also preferred are the above compounds of formula 1, wherein

X denotes SO, $R^1$ denotes H $R^2$ denotes H or $C_{1-10}$-alkyl, which may optionally be substituted by one or more groups selected from halogen and $C_{1-3}$-fluoroalkyl or which may optionally be substituted by one or more groups selected from among $OR^{2.1}$, $COOR^{2.1}$, $CONR^{2.2}R^{2.3}$, $SR^{2.1}$, $SO—R^{2.1}$, $SO_2—R^{2.1}$, phenyl, a het, a hetaryl, a monocyclic $C_{3-7}$-cycloalkyl, $CH_2—NR^{2.2}R^{2.3}$ and $NR^{2.2}R^{2.3}$, which in turn may optionally be substituted by one or more groups selected from among OH, halogen, $OR^{2.1}$, oxo, $CF_3$, $CHF_2$, $CH_2F$, $C_{1-6}$-alkyl, $C_{1-6}$-alkanol, phenyl, $COOR^{2.1}$, $CH_2—NR^{2.2}R^{2.3}$ and $NR^{2.2}R^{2.3}$, wherein $R^{2.1}$ is H or a group selected from among $C_{1-6}$-alkyl, $C_{1-6}$-alkanol, $C_{1-3}$-haloalkyl, monocyclic cycloalkyl, phenyl-$C_{1-6}$-alkylene, hetaryl-$C_{1-6}$-alkylene, het-$C_{1-6}$-alkylene, $C_{3-7}$-cycloalkyl-$C_{1-6}$-alkylene, phenyl, a hetaryl and a het, which may optionally be substituted by one or more groups selected from among OH, halogen, $C_{1-6}$-alkyl, O—($C_{1-3}$-alkyl) and phenyl, wherein $R^{2.2}$ and $R^{2.3}$ independently of one another denote H or a group selected from among $C_{1-6}$-alkyl, monocyclic $C_{3-7}$ cycloalkyl, phenyl-$C_{1-3}$-alkylene, hetaryl-$C_{1-3}$-alkylene, phenyl, monocyclic $C_{3-7}$ heterocycle, hetaryl, CO—$NH_2$, CO—$NHCH_3$, CON($CH_3$)$_2$, $SO_2$—($C_1$-$C_2$-alkyl), CO—$R^{2.1}$ and $COOR^{2.1}$, which may optionally be substituted by one or more groups selected from among OH, halogen, $C_{1-6}$-alkyl, phenyl and $COOR^{2.1}$,
wherein
het is a three- to seven-membered, monocyclic, saturated or partially saturated heterocyclic group, which contains 1, 2 or 3 heteroatoms selected independently of one another from among N, S or O,
and wherein
hetaryl is a five- to six-membered, monocyclic, aromatic heteroaryl, which contains 1, 2 or 3 heteroatoms selected independently of one another from among N, S or O,
and wherein
cycloalkyl may be saturated or partially saturated,
or
$R^2$ denotes a monocyclic $C_{3-7}$ cycloalkyl, which may optionally be substituted by a group selected from among branched or unbranched $C_{1-6}$-alkanol, $C_{1-3}$-fluoroalkyl, $C_{1-3}$-alkylene-$OR^{2.1}$, $OR^{2.1}$, $COOR^{2.1}$, $SO_2$—$NR^{2.2}R^{2.3}$, het, phenyl, $C_{1-6}$-alkyl, phenyl-$C_{1-6}$-alkylene, hetaryl-$C_{1-6}$-alkylene, monocyclic $C_{3-7}$ cycloalkyl and $NR^{2.2}R^{2.3}$, which may optionally be substituted by one or more groups selected from among OH, $OR^{2.1}$, oxo, halogen, $CF_3$, $CHF_2$, $CH_2F$, $C_{1-6}$-alkyl, phenyl and $NR^{2.2}R^{2.3}$,
or
$R^2$ denotes a phenyl, which may optionally be substituted by OH, SH or halogen or by one or more groups selected from among $OR^{2.1}$, $COOR^{2.1}$, $NR^{2.2}R^{2.3}$, $CH_2$—$NR^{2.2}R^{2.3}$, $C_{3-7}$-cycloalkyl, het, $C_{1-6}$-alkyl, $CF_3$, $CHF_2$, $CH_2F$, phenyl-$C_{1-6}$-alkylene, het-$C_{1-6}$-alkylene, hetaryl-$C_{1-6}$-alkylene, phenyl, $SO_2$—$CH_3$, $SO_2$—$CH_2CH_3$ and $SO_2$—$NR^{2.2}R^{2.3}$, which in turn may optionally be substituted by one or more groups selected from among OH, $OR^{2.1}$, oxo, halogen, $CF_3$, $CHF_2$, $CH_2F$, $C_{1-6}$-alkyl, phenyl and $NR^{2.2}R^{2.3}$,
or
$R^2$ denotes a group selected from among a het and a hetaryl, which in turn may optionally be substituted by one or more groups selected from among halogen, OH, oxo, $CF_3$, $CHF_2$ and $CH_2F$ or by one or more groups selected from among $OR^{2.1}$, $CH_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, hetaryl-$C_{1-6}$-alkylene, het, hetaryl, $C_{1-6}$-alkanol, $C_{1-3}$-alkylene-$OR^{2.1}$ and $NR^{2.2}R^{2.3}$, which in turn may optionally be substituted by one or more groups selected from among OH, $OR^{2.1}$, oxo, halogen, $CF_3$, $CHF_2$, $CH_2F$, $C_{1-6}$-alkyl, phenyl and $NR^{2.2}R^{2.3}$,
and wherein
$R^3$ denotes a group selected from among a mono- or bicyclic $C_{6-10}$-aryl, a het and a hetaryl, which may optionally be substituted by one or more groups selected from among halogen, $C_{1-3}$-alkyl, cyclopropyl, $C_{1-3}$-fluoroalkyl, $C_{1-3}$-alkanol, $C_{1-3}$-alkylene-$OR^{2.1}$, OH and O—$C_{1-3}$-alkyl
and wherein
$R^4$ denotes H, $C_{1-6}$-alkyl; F, $C_{1-3}$-fluoroalkyl, $C_{1-6}$-alkylene-OH, $C_{1-6}$-alkylene-$OCH_3$,
$C_{1-6}$-alkylene-$NH_2$, $C_{1-6}$-alkylene-$NH(CH_3)$ or $C_{1-6}$-alkylene-$N(CH_3)_2$,
$R^{4'}$ denotes H or F
or wherein $R^4$ and $R^{4'}$ together represent an oxo group,
and wherein
$R^5$, $R^6$ and $R^7$ independently of one another denote H, $C_{1-6}$-alkyl; F, $C_{1-3}$-fluoroalkyl, $C_{1-6}$-alkylene-OH, $C_{1-6}$-alkylene-$OCH_3$, $C_{1-6}$-alkylene-$NH_2$, $C_{1-6}$-alkylene-$NH(CH_3)$ or $C_{1-6}$-alkylene-$N(CH_3)_2$,
or wherein
$R^6$ and $R^7$ together form a bridge selected from among methylene, ethylene and propylene,
or wherein
$R^5$ and $R^6$ together form a bridge selected from among methylene, ethylene and propylene,
or wherein
$R^3$, $R^4$ and $R^{4'}$ together with the C— and the N atom of the piperazine form an unsaturated or partially unsaturated, 5- or 6-membered heterocyclic group containing two or three, but at least two nitrogen atoms,
wherein this heterocyclic group may optionally be substituted by one, two or three groups selected from among oxo, OH, halogen, $C_{1-6}$-alkyl, cyclopropyl, $C_{1-3}$-fluoroalkyl, $C_{1-3}$-alkylene-$OR^{2.1}$, $C_{1-6}$-alkanol, $COOR^{2.1}$, $C_{6-10}$-aryl, $C_{1-3}$-alkylene-$C_{6-10}$-aryl, hetaryl, $C_{1-3}$-alkylene-hetaryl, het, CO-het, $C_{1-3}$-alkylene-het-CO—N($CH_3$)-het, —CO—NH-het, —CO—O—N($CH_3$)-het, —CO—O—NH-het, —CO—N($CH_3$)—$C_{3-7}$-cycloalkyl, —CO—NH—$C_{3-7}$-cycloalkyl, —CO—O—N($CH_3$)—$C_{3-7}$-cycloalkyl, —CO—NH—$C_{3-7}$-cycloalky, —CO—NH—$C_{1-2}$-alkylene-hetaryl, —CO—N($CH_3$)—$C_{1-2}$-alkylene-hetaryl, —CO—NH—CH($CH_3$)-hetaryl, —CO—NH—C($CH_3$)$_2$-hetaryl, —CO—N(cyclopropyl)-het and —CO—N(cyclopropyl)-hetaryl,
which in turn may optionally be substituted by one or more groups selected from among OH, oxo, halogen, $C_{1-6}$-alkyl, $C_{1-3}$-fluoroalkyl and $C_{1-6}$-alkanol,
and the pharmacologically acceptable salts, diastereomers, enantiomers, racemates, hydrates or solvates thereof.

Also preferred are the above-mentioned compounds of formula 1, wherein
X is SO,
$R^2$ is H or $C_{1-6}$-alkyl, which may optionally be substituted by F, $CF_3$, $CHF_2$ or $CH_2F$ or which in turn may optionally be substituted by one or more groups selected from among $OR^{2.1}$, $COOR^{2.1}$, $CONR^{2.2}R^{2.3}$, $SR^{2.1}$, SO—$R^{2.1}$, $SO_2$—$R^{2.1}$, phenyl, a het, a hetaryl, a monocyclic $C_{3-7}$-cycloalkyl, $CH_2$—$NR^{2.2}R^{2.3}$ and $NR^{2.2}R^{2.3}$, which in turn may optionally be substituted by one or more groups selected from among OH, halogen, $CF_3$, $CHF_2$, $CH_2F$, $OR^{2.1}$, oxo, $C_{1-6}$-alkyl, $C_{1-6}$-alkanol, phenyl, $COOR^{2.1}$, $CH_2$—$NR^{2.2}R^{2.3}$ and $NR^{2.2}R^{2.3}$,
wherein $R^{2.1}$ is H or a group selected from among $C_{1-6}$-alkyl, $C_{1-6}$-alkanol, monocyclic $C_{3-7}$ cycloalkyl, phenyl-$CH_2$, hetaryl-methylene, het-methylene, $C_{3-7}$-cycloalkyl-methylene, phenyl, a hetaryl and a het,
which may optionally be substituted by one or more groups selected from among OH, F, Cl, Br, I, methyl, ethyl, propyl, isopropyl, O-methyl, O-ethyl, O-propyl, O-isopropyl and phenyl,
wherein $R^{2.2}$ and $R^{2.3}$ independently of one another denote H or a group selected from among methyl, ethyl, propyl, isopropyl, monocyclic $C_{3-7}$ cycloalkyl, phenyl-methylene, hetaryl-methylene, phenyl, het, hetaryl, CO—$NH_2$, CO—$NHCH_3$, $CON(CH_3)_2$, $SO_2$—($C_1$-$C_2$-alkyl), CO—$R^{2.1}$ and $COOR^{2.1}$, which may optionally be substituted by one or more groups selected from among OH, F, Cl, Br, methyl, ethyl, phenyl and $COOR^{2.1}$,
and wherein $R^1$, $R^3$, $R^4$, $R^{4'}$, $R^5$, $R^6$ and $R^7$ are as hereinbefore defined, and the pharmacologically acceptable salts, diastereomers, enantiomers, racemates, hydrates or solvates thereof.

Also preferred are the above-mentioned compounds of formula 1 wherein
$R^2$ is a group according to formula 2

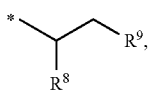

wherein $R^9$ is OH or $NH_2$ and
wherein $R^8$ is a group selected from among $C_{1-6}$-alkyl, hetaryl and phenyl, which may optionally be substituted by one or more groups selected from among OH, F, Br, $OR^{2.1}$, oxo, methyl, ethyl, $C_{1-2}$-alkanol, phenyl, $COOR^{2.1}$, $CH_2$—$NR^{2.2}R^{2.3}$ and $NR^{2.2}R^{2.3}$,
and wherein the remaining groups are as hereinbefore defined,
and the pharmacologically acceptable salts, diastereomers, enantiomers, racemates, hydrates or solvates thereof.

Particularly preferred are the above mentioned compounds of formula 1, wherein
$R^2$ is a group according to formula 2

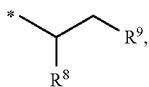

wherein $R^9$ is OH or $NH_2$ and
wherein $R^8$ is methyl, ethyl, propyl, isopropyl
and wherein the remaining groups are as hereinbefore defined,
and the pharmacologically acceptable salts, diastereomers, enantiomers, racemates, hydrates or solvates thereof.

In another preferred aspect the invention relates to the above mentioned compounds of formula 1, wherein
$R^2$ is a monocyclic three-, four-, five-, six- or seven-membered cycloalkyl ring which may optionally be substituted in the spiro position by a group selected from among —$CH_2$—$OR^{2.1}$, branched or unbranched $C_{2-6}$-alkylene-$OR^{2.1}$, methyl, ethyl, propyl, isopropyl, butyl, isobutyl, cyclopropyl, and —$CF_3$, $CHF_2$, $CH_2F$ and $C_{2-4}$-fluoroalkyl, wherein
$R^{2.1}$ is selected from among methyl, ethyl, propyl, isopropyl, butyl, isobutyl,
and wherein the remaining groups are as hereinbefore defined,
and the pharmacologically acceptable salts, diastereomers, enantiomers, racemates, hydrates or solvates thereof.

Particularly preferred are the above mentioned compounds of formula 1 wherein
$R^2$ is a phenyl, which is optionally substituted in one or both meta positions by one or more groups selected from among methyl, ethyl, propyl, isopropyl, cyclopropyl, F, Cl, Br, OH, $OR^{2.1}$, $COOR^{2.1}$, $CF_3$, $CHF_2$, $CH_2F$, $NH_2$, $NH(CH_3)$ and $N(CH_3)_2$, wherein $R^{2.1}$ may be H, methyl or ethyl,
and wherein the remaining groups are as hereinbefore defined,
and the pharmacologically acceptable salts, diastereomers, enantiomers, racemates, hydrates or solvates thereof.

Also particularly preferred are the above mentioned compounds of formula 1, wherein
$R^2$ is a group selected from among monocyclic, saturated three-, four-, five-, six- or seven-membered heterocyclic groups with 1, 2 or 3 heteroatoms in each case selected from among N, O and S, which may optionally be substituted by one or more groups selected from among fluorine, OH, $CF_3$, $CHF_2$, $CH_2F$ and oxo or by one or more groups selected from among $OR^{2.1}$, $C_{1-3}$-alkylene-$OR^{2.1}$, $SR^{2.1}$, SO—$R^{2.1}$, $SO_2$—$R^{2.1}$, $COOR^{2.1}$, $COR^{2.1}$, $C_{1-6}$-alkanol, $C_{3-10}$-cycloalkyl, phenyl, $C_{1-6}$-alkyl, phenyl-$C_{1-6}$-alkylene, hetaryl-$C_{1-6}$-alkylene, het, hetaryl and $NR^{2.2}R^{2.3}$, which in turn may optionally be substituted by one or more groups selected from among OH, $OR^{2.1}$, oxo, F, Cl, $CF_3$, $CHF_2$, $CH_2F$, $C_{1-6}$-alkyl, phenyl and $NR^{2.2}R^{2.3}$,
wherein $R^{2.1}$, $R^{2.2}$ and $R^{2.3}$ and the remaining groups are as hereinbefore defined,
and the pharmacologically acceptable salts, diastereomers, enantiomers, racemates, hydrates or solvates thereof.

Also particularly preferred are the above mentioned compounds of formula 1, wherein
$R^2$ is a group selected from among a monocyclic, saturated six-membered heterocyclic group with at least one heteroatom selected in each case from among N, O and S, which may optionally be substituted by one or more groups selected from among F, Cl, Br, $CF_3$, $CHF_2$, $CH_2F$, OH, oxo, $NH_2$, $NHCH_3$, $N(CH_3)_2$, methyl, ethyl, propyl, isopropyl, cyclopropyl, methoxy and ethoxy,
and wherein the remaining groups are as hereinbefore defined,
and the pharmacologically acceptable salts, diastereomers, enantiomers, racemates, hydrates or solvates thereof.

Also particularly preferred are the above mentioned compounds of formula 1, wherein
$R^2$ is a group selected from among piperidine or tetrahydropyran, which may optionally be substituted by one or more groups selected from among F, Cl, Br, OH, $CF_3$, $CHF_2$, $CH_2F$, $NH_2$, $NHCH_3$, $N(CH_3)_2$, oxo, methyl and methoxy,
and wherein the remaining groups are as hereinbefore defined,
and the pharmacologically acceptable salts, diastereomers, enantiomers, racemates, hydrates or solvates thereof.

Also particularly preferred are the above mentioned compounds of formula 1, wherein
$R^3$ is a group selected from the group comprising a phenyl, which may optionally be substituted by one or more groups selected from among F, Cl, Br, methyl, ethyl, propyl, isopropyl, cyclopropyl, $C_{1-3}$-fluoroalkyl, $C_{1-3}$-alkanol, OH and O—$C_{1-3}$-alkyl,
and wherein the remaining groups are as hereinbefore defined,
and the pharmacologically acceptable salts, diastereomers, enantiomers, racemates, hydrates or solvates thereof.

In another preferred aspect the invention relates to the above mentioned compounds of formula 1, wherein
$R^3$ is a group selected from among a mono- or bicyclic, saturated, unsaturated or partially saturated three- to ten-membered heterocyclic group with 1 to 3 heteroatoms selected from N, O and S, which may optionally be substituted by one or more groups selected from among F, Cl, Br, methyl, ethyl, propyl, isopropyl, cyclopropyl, $C_{1-3}$-fluoroalkyl, $C_{1-3}$-alkanol, OH and O—$C_{1-3}$-alkyl,
and wherein the remaining groups are as hereinbefore defined,
and the pharmacologically acceptable salts, diastereomers, enantiomers, racemates, hydrates or solvates thereof.

In another preferred aspect the invention relates to the above mentioned compounds of formula 1, wherein
$R^3$ and $R^4$ together with the C— and the N atom of the piperazine form a saturated or partially unsaturated 5- or 6-membered heterocyclic group
containing two or three, but at least two nitrogen atoms,
or wherein
$R^3$, $R^4$ and $R^{4'}$ together with the C— and the N atom of the piperazine form an unsaturated or partially unsaturated, 5- or 6-membered heterocyclic group containing two or three, but at least two nitrogen atoms, wherein this heterocyclic group may optionally be substituted by one, two or three groups selected from among oxo, OH, F, Cl, Br, $C_{1-6}$-alkyl, cyclopropyl, $C_{1-3}$-fluoroalkyl, $C_{1-6}$-alkanol, $COOR^{2.1}$, phenyl, $C_{1-3}$-alkylene-phenyl, hetaryl, $C_{1-3}$-alkylene-hetaryl, het, CO-het, $C_{1-3}$-alkylene-het, —CO—N(CH$_3$)-het, —CO—NH-het, —CO—O—N(CH$_3$)-het, —CO—O—NH-het, —CO—N(CH$_3$)—$C_{3-7}$-cycloalkyl, —CO—NH—$C_{3-7}$-cycloalkyl, —CO—O—N(CH$_3$)—$C_{3-7}$-cycloalkyl, —CO—O—NH—$C_{3-7}$-cycloalkyl, —CO—NH—$C_{1-2}$-alkylene-hetaryl, —CO—N(CH$_3$)—$C_{1-2}$-alkylene-hetaryl, —CO—NH—CH(CH$_3$)-hetaryl, —CO—NH—C(CH$_3$)$_2$-hetaryl, —CO—N(cyclopropyl)-het and —CO—N(cyclopropyl)-hetaryl, which in turn may optionally be substituted by one or more groups selected from among OH, oxo, F, Cl, Br, $C_{1-6}$-alkyl, $C_{1-3}$-fluoroalkyl, $C_{1-6}$-alkanol, and wherein the remaining groups are as hereinbefore defined, and the pharmacologically acceptable salts, diastereomers, enantiomers, racemates, hydrates or solvates thereof.

In another preferred aspect the invention relates to the above mentioned compounds of formula 1, wherein
$R^3$, $R^4$ and $R^{4'}$ together with the C and the N atom of the piperazine form a five-membered heterocyclic group selected from among imidazole, pyrazole and triazole, which may optionally be substituted by one, two or three groups selected from among oxo, OH, F, Cl, Br, $C_{1-3}$-fluoroalkyl, methyl, ethyl, propyl, isopropyl, cyclopropyl, $COOR^{2.1}$, phenyl, $C_{1-3}$-alkylene-phenyl, hetaryl, $C_{1-3}$-alkylene-hetaryl, het, CO-het, $C_{1-3}$-alkylene-het, —CO—N(CH$_3$)-het, —CO—NH-het, —CO—O—N(CH$_3$)-het, —CO—O—NH-het, —CO—N(CH$_3$)—$C_{3-7}$-cycloalkyl, —CO—NH—$C_{3-7}$-cycloalkyl, —CO—O—N(CH$_3$)—$C_{3-7}$-cycloalkyl, —CO—O—NH—$C_{3-7}$-cycloalkyl, —CO—NH—$C_{1-2}$-alkylene-hetaryl, —CO—N(CH$_3$)—$C_{1-2}$-alkylene-hetaryl, —CO—NH—CH(CH$_3$)-hetaryl, —CO—NH—C(CH$_3$)$_2$-hetaryl, —CO—N(cyclopropyl)-het and —CO—N(cyclopropyl)-hetaryl, which in turn may optionally be substituted by one or more groups selected from among OH, oxo, F, Cl, Br, $C_{1-6}$-alkyl, $C_{1-3}$-fluoroalkyl and $C_{1-6}$-alkanol, wherein $R^{2.1}$ may be H, methyl, ethyl, propyl or isopropyl, and wherein the remaining groups are as hereinbefore defined, and the pharmacologically acceptable salts, diastereomers, enantiomers, racemates, hydrates or solvates thereof.

Particularly preferred are the above mentioned compounds of formula 1,
wherein
$R^4$ is H or methyl and
$R^{4'}$ is H
or wherein $R^4$ and $R^{4'}$ together represent an oxo group,
and wherein the remaining groups are as hereinbefore defined,
and the pharmacologically acceptable salts, diastereomers, enantiomers, racemates, hydrates or solvates thereof.

Also particularly preferred are the above mentioned compounds of formula 1, wherein
$R^5$, $R^6$ and $R^7$ independently of one another denote H or methyl,
and wherein the remaining groups are as hereinbefore defined,
and the pharmacologically acceptable salts, diastereomers, enantiomers, racemates, hydrates or solvates thereof.

Also particularly preferred are the above mentioned compounds of formula 1, wherein
$R^6$ and $R^7$ together form a bridge selected from among methylene and ethylene, or wherein
$R^5$ and $R^6$ together form a bridge selected from among methylene and ethylene, and wherein the remaining groups are as hereinbefore defined, and the pharmacologically acceptable salts, diastereomers, enantiomers, racemates, hydrates or solvates thereof.

In a particularly preferred aspect the invention also relates to the above mentioned compounds of formula 1, wherein the compounds are selected from among

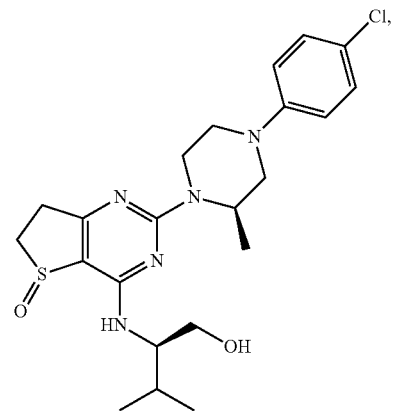

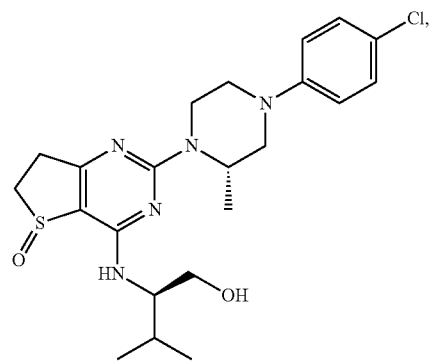

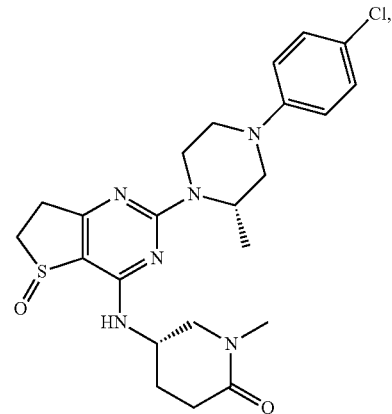

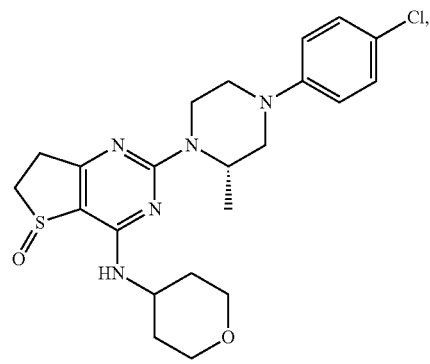

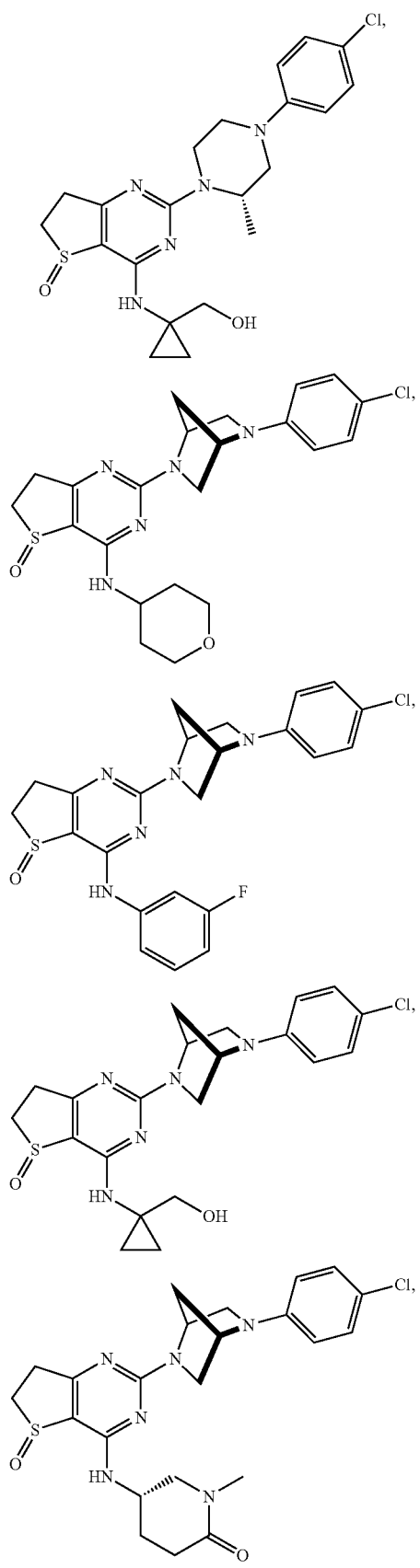
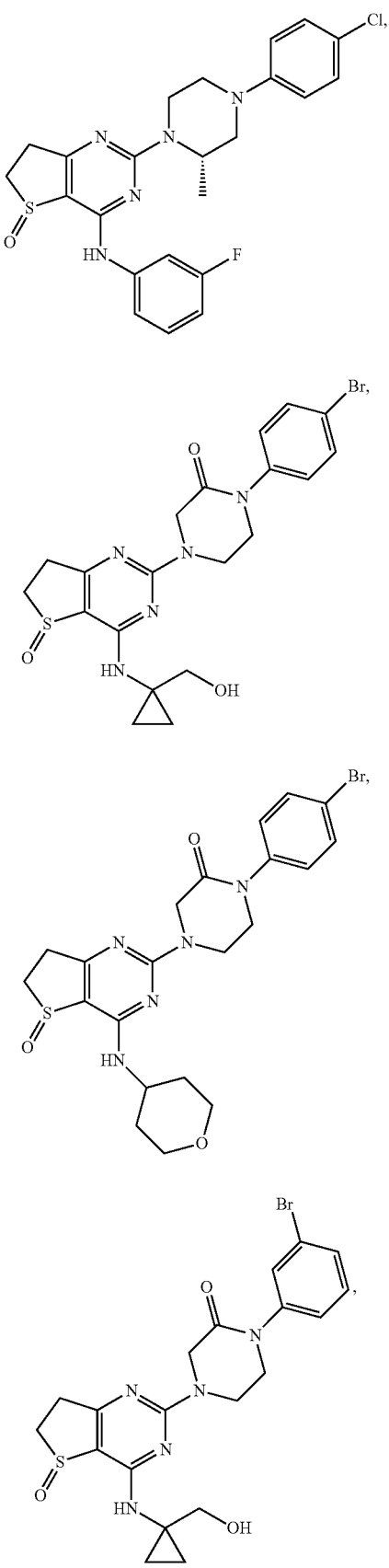 [SMILES: C[C@H]1CN(c2ccc(Cl)cc2)CCN1c1nc2c(c(Nc3cccc(F)c3)n1)S(=O)CC2 ; O=C1CN(c2nc3c(c(NC4(CO)CC4)n2)S(=O)CC3)CCN1c1ccc(Br)cc1 ; O=C1CN(c2nc3c(c(NC4CCOCC4)n2)S(=O)CC3)CCN1c1ccc(Br)cc1 ; O=C1CN(c2nc3c(c(NC4(CO)CC4)n2)S(=O)CC3)CCN1c1cccc(Br)c1]

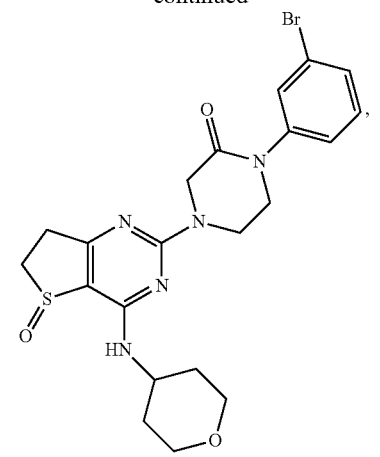
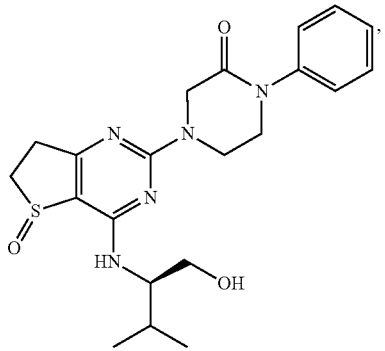
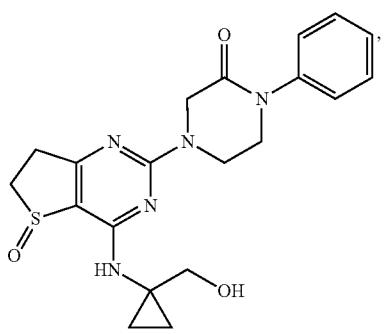
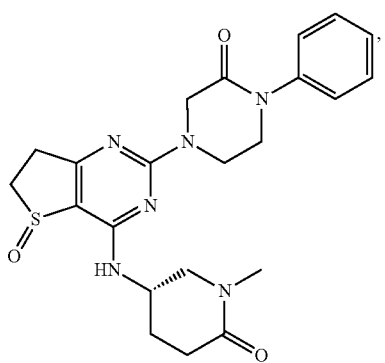
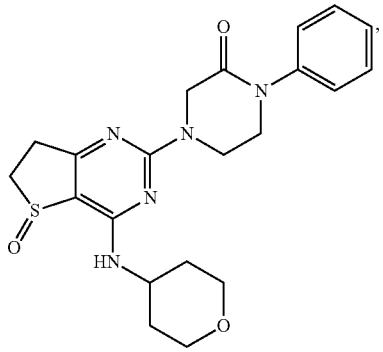
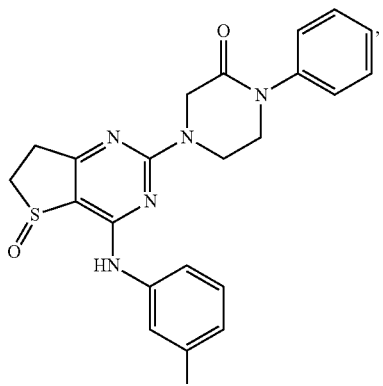
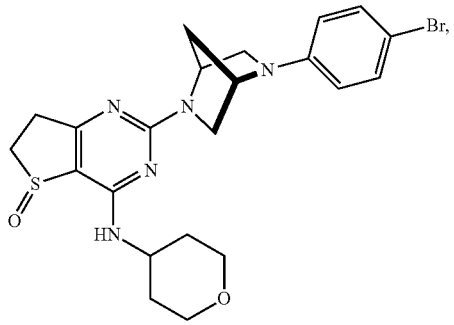
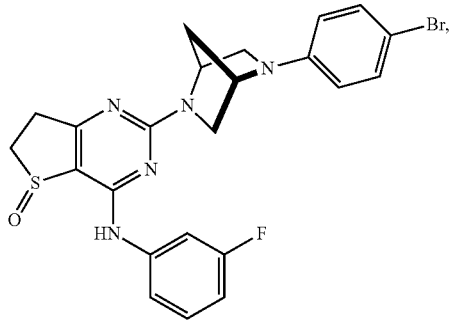
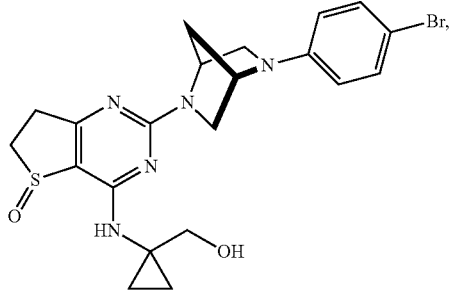

17
-continued
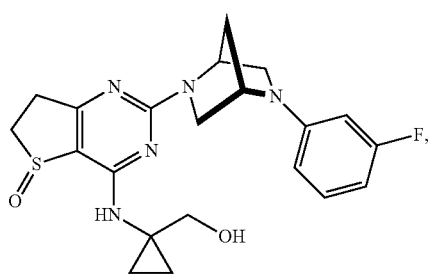
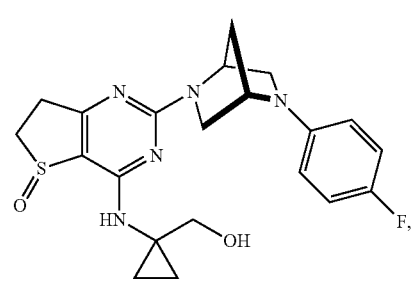
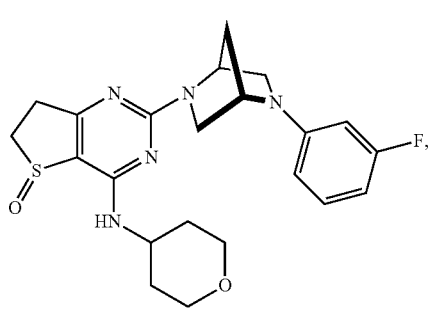
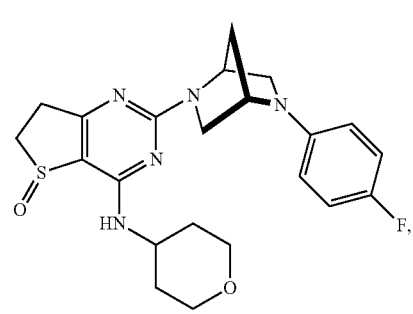
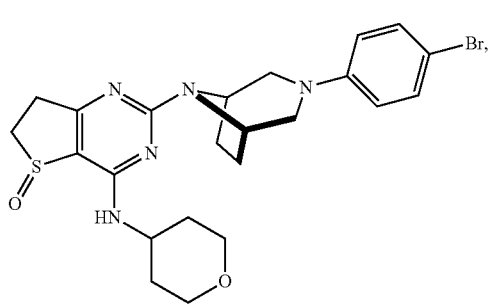
18
-continued
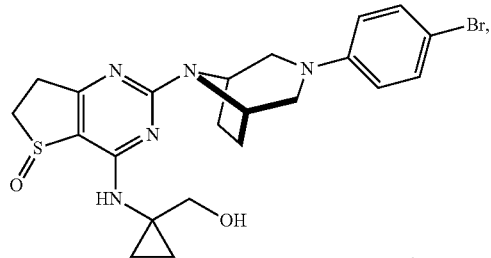
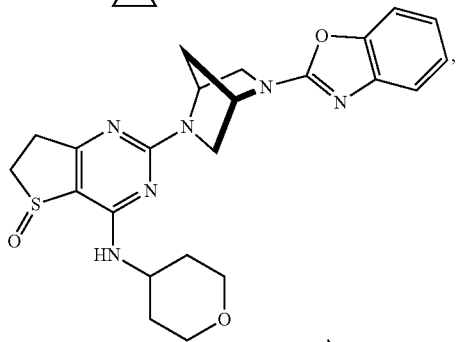
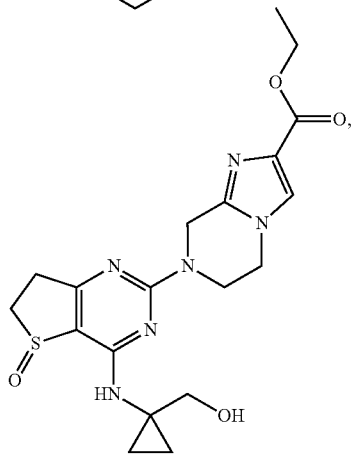
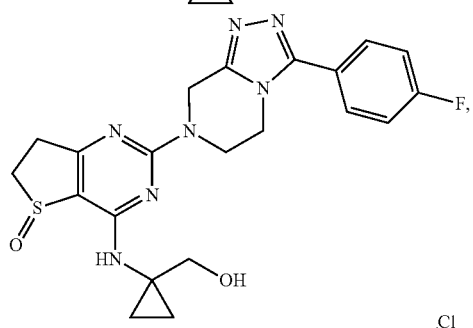
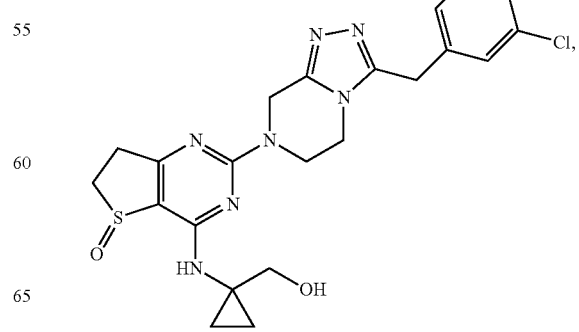

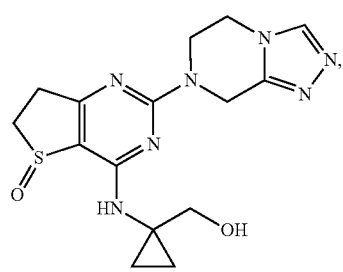
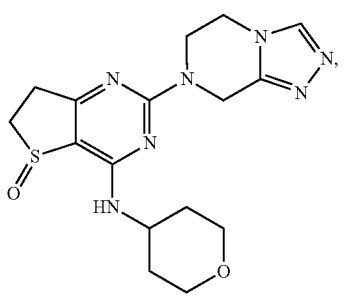
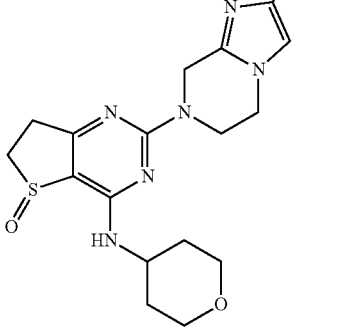
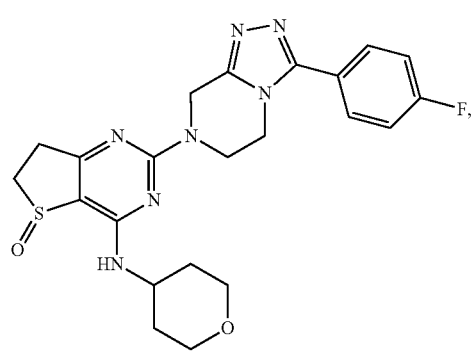
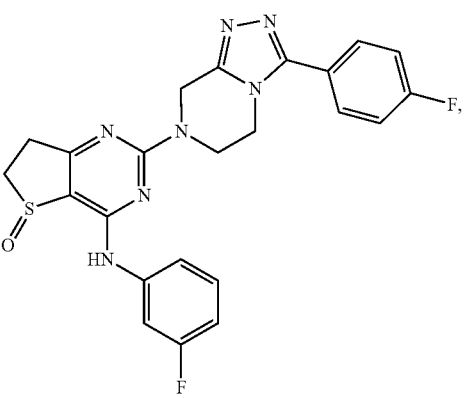
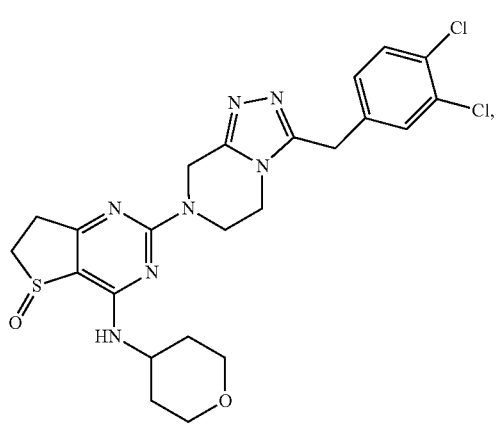

-continued
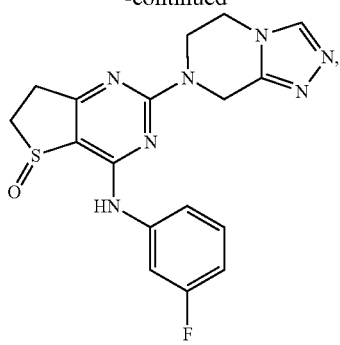
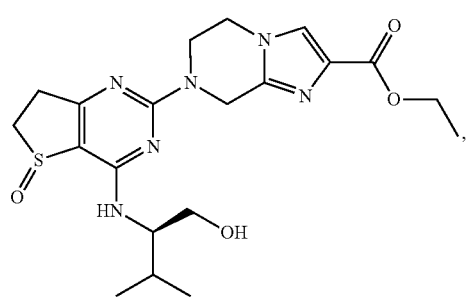
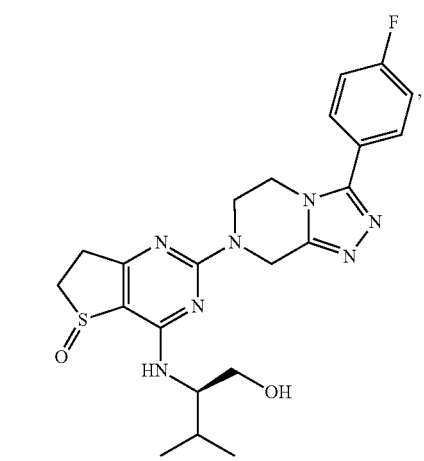
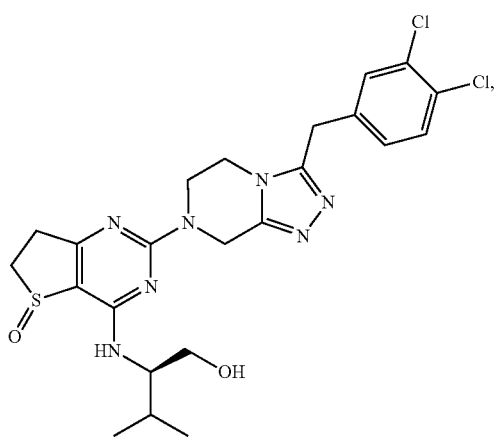
-continued
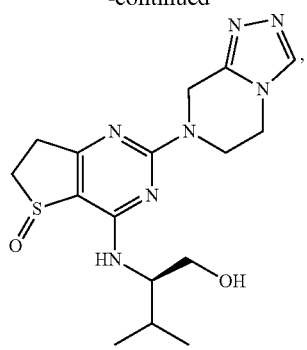
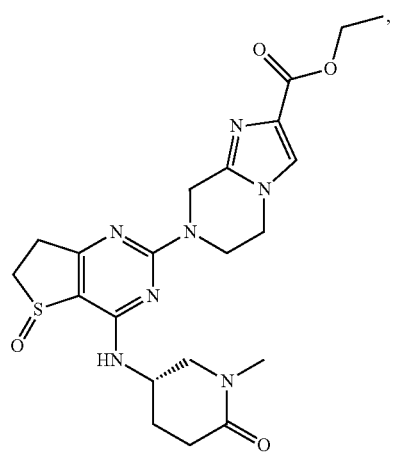
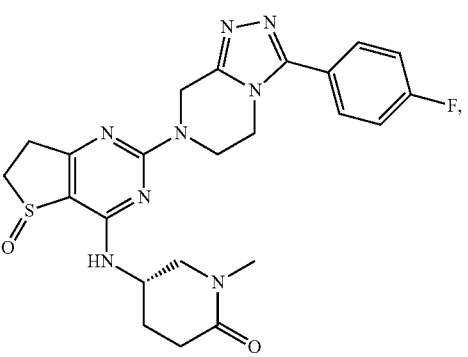
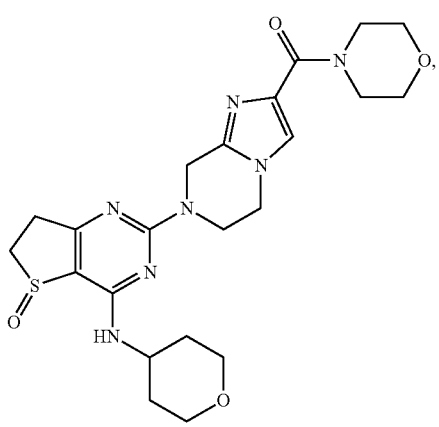

23
-continued
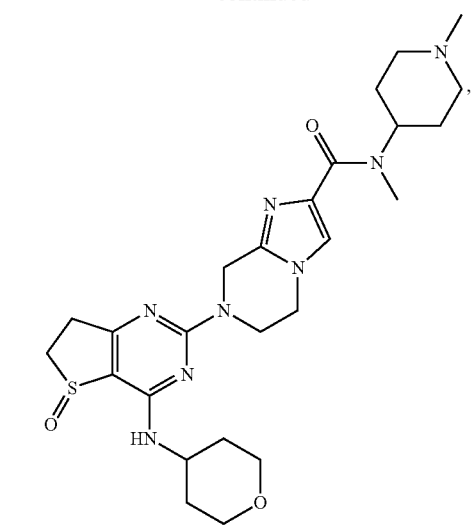
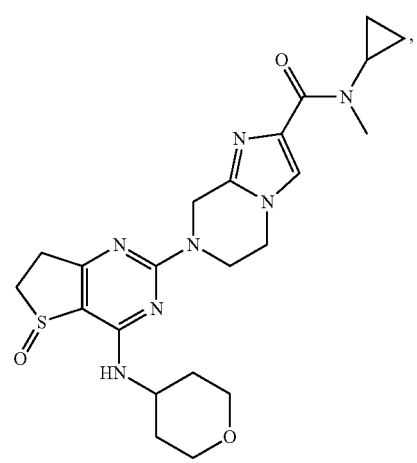
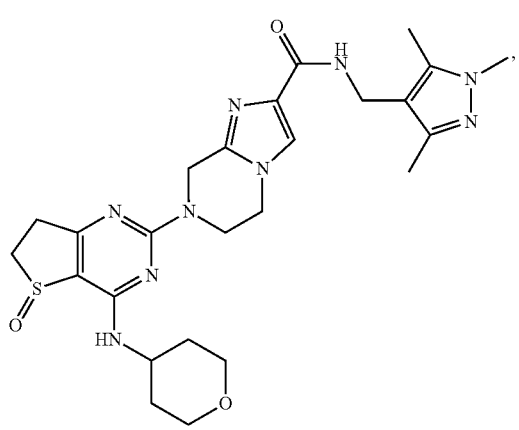 [SMILES: Cc1nn(C)cc1CNC(=O)c1cn2c(n1)CN(c1nc3c(c(NC4CCOCC4)n1)S(=O)CC3)CC2]
24
-continued
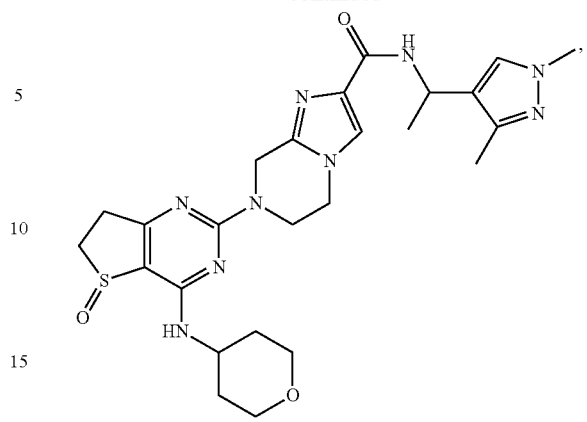
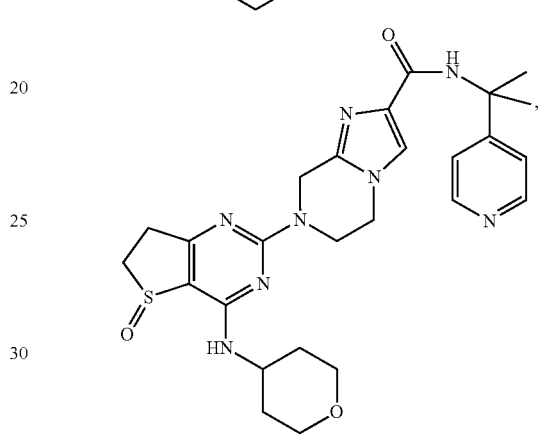
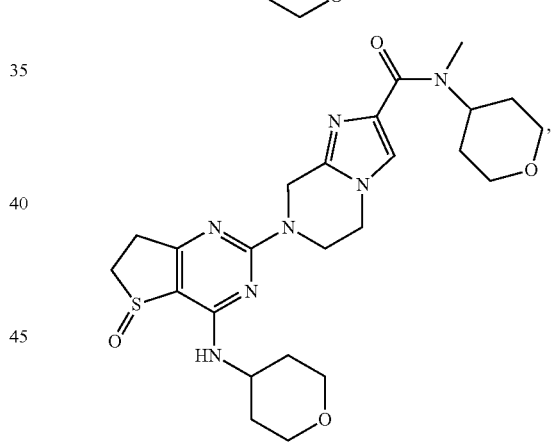
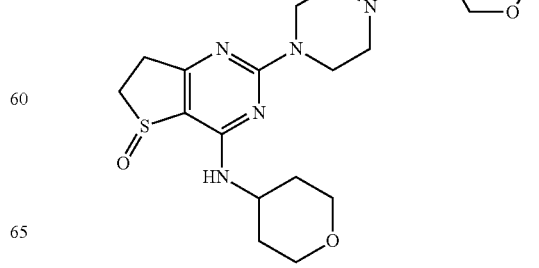

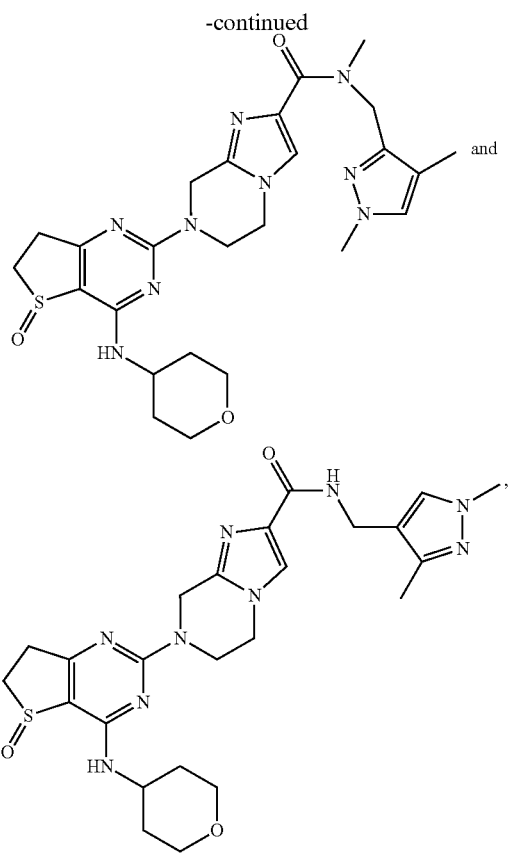

and and the pharmacologically acceptable salts, diastereomers, enantiomers, racemates, hydrates or solvates thereof, but particularly both the R-enantiomers and the S-enantiomers in relation to the stereocentre at the sulphoxide sulphur atom of the above-mentioned compounds.

The invention further relates to the above compounds of formula 1 as medicaments.

The invention further relates to the use of the above compounds according to formula 1 for preparing a medicament for the treatment of diseases that can be treated by inhibiting the PDE4 enzyme.

The invention further relates to the use of the above compounds according to formula 1 for preparing a medicament for the treatment of respiratory or gastrointestinal complaints or diseases, such as inflammatory diseases of the joints, skin or eyes, cancers, and diseases of the peripheral or central nervous system.

The invention further relates to the use of the above compounds according to formula 1 for preparing a medicament for the prevention and treatment of respiratory or pulmonary diseases which are associated with increased mucus production, inflammation and/or obstructive diseases of the respiratory tract.

The invention further relates to the use of the above compounds according to formula 1 for preparing a medicament for the treatment of inflammatory and obstructive diseases such as COPD, chronic sinusitis, asthma, Crohn's disease, ulcerative colitis.

The invention further relates to the use of the above compounds according to formula 1 for preparing a medicament for the treatment of inflammatory diseases of the gastrointestinal tract.

The invention further relates to the use of the above compounds according to formula 1 for preparing a medicament for the prevention and treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain as well as injury to the brain caused by stroke, hypoxia or cranio-cerebral trauma.

The invention further relates to pharmaceutical formulations which contain one or more of the above compounds according to formula 1.

The invention further relates to pharmaceutical formulations containing one or more compounds of formula 1 in combination with one or more active substances selected from among betamimetics, corticosteroids, other PDE4-inhibitors, EGFR-inhibitors and LTD4-antagonists, CCR3-inhibitors, iNOS-inhibitors and SYK-inhibitors.

TERMS AND DEFINITIONS USED

Unless stated otherwise, all the substituents are independent of one another. If for example a number of $C_{1-6}$-alkyl groups are possible substituents at a group, in the case of three substituents, for example, $C_{1-6}$-alkyl could represent, independently of one another, a methyl, an n-propyl and a tert-butyl.

Within the scope of this application, in the definition of possible substituents, these may also be presented in the form of a structural formula. An asterisk (*) in the structural formula of the substituent is to be understood as being the linking point to the rest of the molecule. Moreover, the atom of the substituent following the linking point is understood as being the atom in position number 1. Thus for example the groups N-piperidinyl (I), 4-piperidinyl (II), 2-tolyl (III), 3-tolyl (IV) and 4-tolyl (V) are represented as follows:

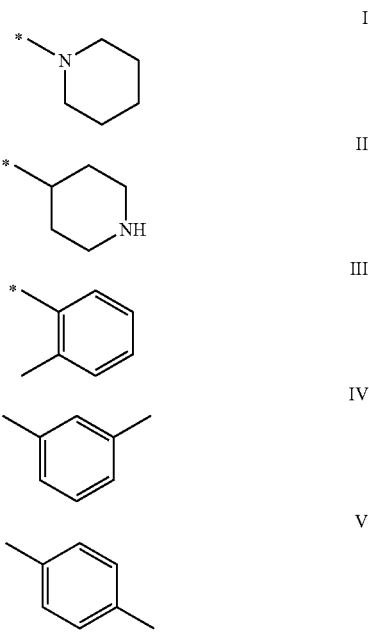

If there is no asterisk (*) in the structural formula of the substituent, each hydrogen atom may be removed at the substituent and the valency thus freed may serve as a binding site to the rest of a molecule, provided that the linking point to the rest of the molecule is not specified or defined in some other manner. Thus, for example, VI may represent 2-tolyl, 3-tolyl, 4-tolyl and benzyl.

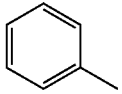

VI

By the term "$C_{1-10}$-alkyl" (including those which are part of other groups) are meant branched and unbranched alkyl group with 1 to 10 carbon atoms and by the term "$C_{1-6}$-alkyl" are meant branched and unbranched alkyl groups with 1 to 6 carbon atoms. "$C_{1-4}$-alkyl" accordingly denotes branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc., may also optionally be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples of these include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl includes also 1-methylethylene and butylene includes 1-methylpropylene, 1,1-dimethylethylene, 1,2-dimethylethylene.

If the carbon chain is substituted by a group which together with one or two carbon atoms of the alkylene chain forms a carbocyclic ring with 3, 5 or 6 carbon atoms, this includes, inter alia, the following examples of the rings:

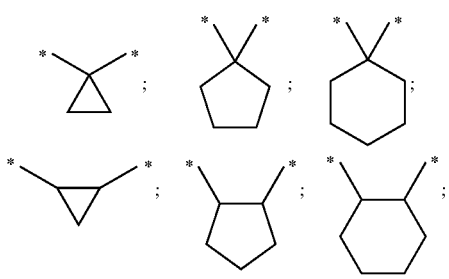

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples of these include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1,2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated, otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include: benzyl, 1- or 2-phenylethyl or 1- or 2-naphthylethyl. Unless otherwise stated, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—even though they are already included under "aryl-$C_{1-6}$-alkylene"—branched and unbranched alkylene groups with 1 to 6 carbon atoms, which are substituted by a heteroaryl.

A heteroaryl of this kind includes five- or six-membered heterocyclic aromatic groups or 5-10-membered, bicyclic heteroaryl rings which may contain one, two or three heteroatoms selected from among oxygen, sulphur and nitrogen, and contain so many conjugated double bonds that an aromatic system is formed. The following are examples of five- or six-membered heterocyclic aromatic groups or bicyclic heteroaryl rings:

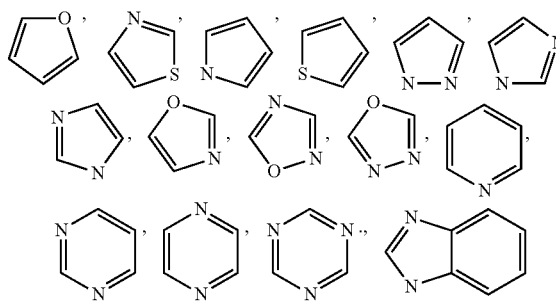

Unless otherwise stated, these heteroaryls may be substituted by one or more groups selected from among methyl, ethyl, iso-propyl, tert-butyl, hydroxy, fluorine, chlorine, bromine and iodine.

The following are examples of heteroaryl-$C_{1-6}$-alkylenes:

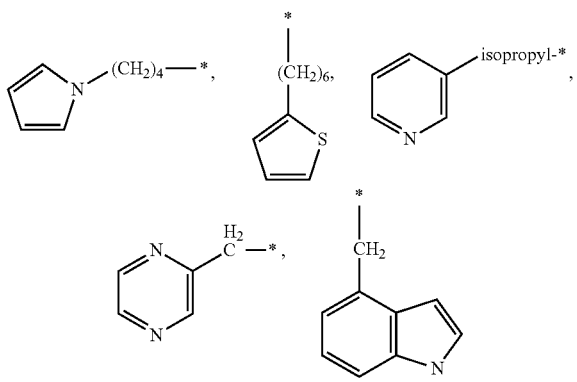

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{3-10}$-cycloalkyl" are also meant monocyclic alkyl groups with 3 to 7 carbon atoms and also bicyclic alkyl groups with 7 to 10 carbon atoms, or monocyclic alkyl groups which are bridged by at least one $C_{1-3}$-carbon bridge.

By the term "heterocyclic rings" or "heterocycle" are meant five-, six- or seven-membered, saturated or unsaturated heterocyclic rings which may contain one, two or three heteroatoms, selected from among oxygen, sulphur and nitrogen, while the ring may be linked to the molecule through a carbon atom or through a nitrogen atom, if there is one. Although included by the term "heterocyclic rings" or "heterocycles", the term "heterocyclic non-aromatic rings" refers to five-, six- or seven-membered unsaturated rings. Examples include:

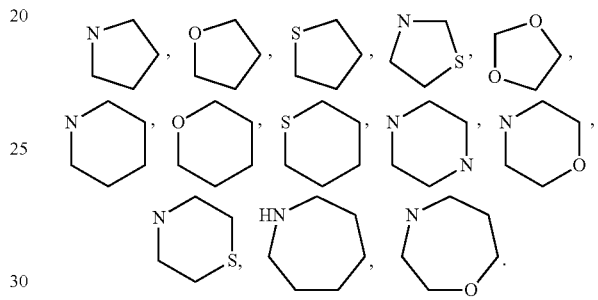

Although included by the term "heterocyclic rings" or "heterocycles", the term "heterocyclic aromatic rings" or "heteroaryl" refers to five- or six-membered heterocyclic aromatic groups or 5-10-membered, bicyclic heteroaryl rings which may contain one, two, three or four heteroatoms, selected from among oxygen, sulphur and nitrogen, and contain so many conjugated double bonds that an aromatic system is formed. Examples of five- or six-membered heterocyclic aromatic groups include:

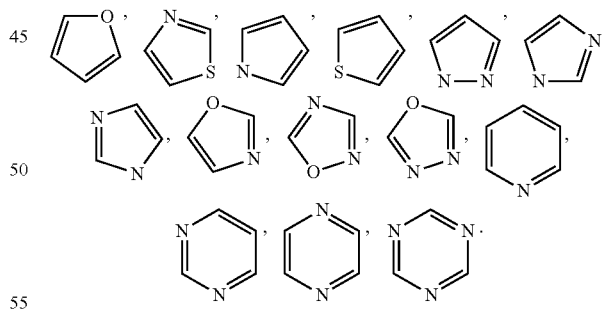

Unless otherwise mentioned, a heterocyclic ring (or heterocycle) may be provided with a keto group. Examples include:

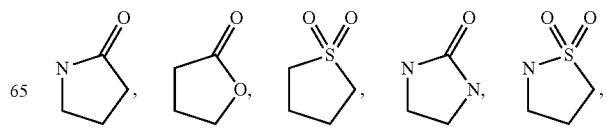

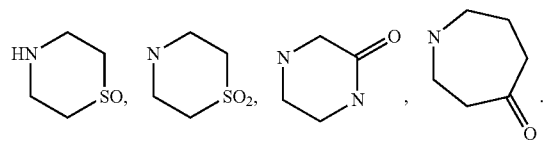

Although covered by the term "cycloalkyl", the subsidiary term "bicyclic cycloalkyls" generally denotes eight-, nine- or ten-membered bicyclic carbon rings. Examples include

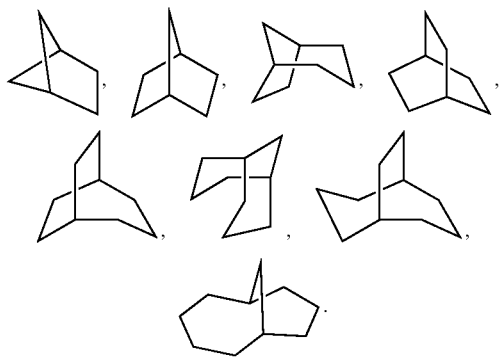

Although already included by the term "heterocycle", the term "bicyclic heterocycles" generally denotes eight-, nine- or ten-membered bicyclic rings which may contain one or more heteroatoms, preferably 1-4, more preferably 1-3, even more preferably 1-2, particularly one heteroatom, selected from among oxygen, sulphur and nitrogen. The ring may be linked to the molecule through a carbon atom of the ring or through a nitrogen atom of the ring, if there is one. Examples include:

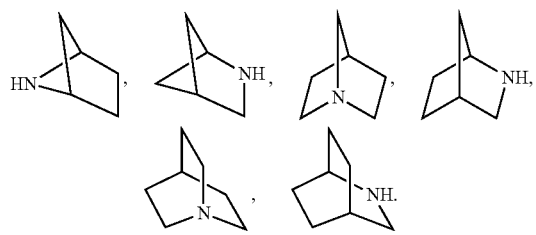

Although already included by the term "aryl", the term "bicyclic aryl" denotes a 5-10 membered, bicyclic aryl ring which contains sufficient conjugated double bonds to form an aromatic system. One example of a bicyclic aryl is naphthyl.

Although already included under "heteroaryl", the term "bicyclic heteroaryl" denotes a 5-10 membered, bicyclic heteroaryl ring which may contain one, two, three or four heteroatoms, selected from among oxygen, sulphur and nitrogen, and contains sufficient conjugated double bonds to form an aromatic system.

Although included by the term "bicyclic cycloalkyls" or "bicyclic aryl", the term "fused cycloalkyl" or "fused aryl" denotes bicyclic rings wherein the bridge separating the rings denotes a direct single bond. The following are examples of a fused, bicyclic cycloalkyl:

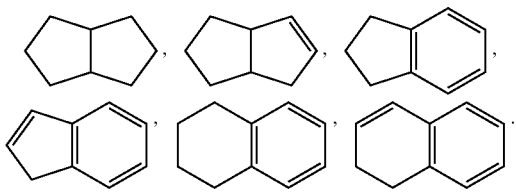

Although included by the term "bicyclic heterocycles" or "bicyclic heteroaryls", the term "fused bicyclic heterocycles" of "fused bicyclic heteroaryls" denotes bicyclic 5-10 membered heterorings which contain one, two or three heteroatoms, selected from among oxygen, sulphur and nitrogen and wherein the bridge separating the rings denotes a direct single bond. The "fused bicyclic heteroaryls" moreover contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

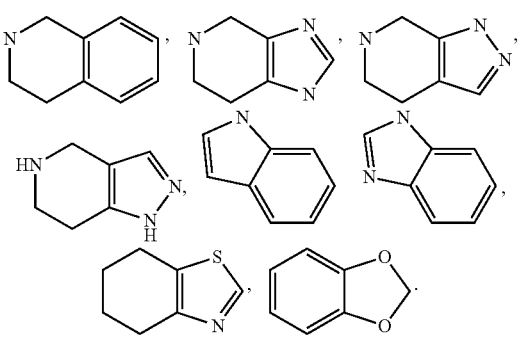

By the term "heterocyclic spiro rings" (Spiro) are meant 5-10 membered, spirocyclic rings which may optionally contain one, two or three heteroatoms, selected from among oxygen, sulphur and nitrogen, while the ring may be linked to the molecule through a carbon atom or if available through a nitrogen atom. Unless otherwise mentioned, a spirocyclic ring may be provided with an oxo, methyl or ethyl group. Examples of this include:

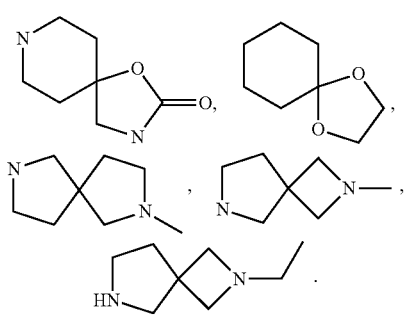

"Halogen" within the scope of the present invention denotes fluorine, chlorine, bromine or iodine. Unless stated to the contrary, fluorine, chlorine and bromine are regarded as preferred halogens.

Compounds of general formula 1 may have acid groups, mainly carboxyl groups, and/or basic groups such as e.g. amino functions. Compounds of general formula 1 may therefore be present as internal salts, as salts with pharmaceutically usable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically usable bases such as alkali metal or alkaline earth metal hydroxides or carbonates, zinc or ammonium hydroxides or organic amines such as e.g. diethylamine, triethylamine, triethanolamine, inter alia.

As mentioned previously, the compounds of formula 1 may be converted into the salts thereof, particularly for pharmaceutical use into the physiologically and pharmacologically acceptable salts thereof. These salts may be present on the one hand as physiologically and pharmacologically acceptable acid addition salts of the compounds of formula 1 with inorganic or organic acids. On the other hand, the compound of formula 1 when R is hydrogen may be converted by reaction with inorganic bases into physiologically and pharmacologically acceptable salts with alkali or alkaline earth metal cations as counter-ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. To prepare the alkali and alkaline earth metal salts of the compound of formula 1 wherein R denotes hydrogen, it is preferable to use the alkali and alkaline earth metal hydroxides and hydrides, of which the hydroxides and hydrides of the alkali metals, particularly sodium and potassium, are preferred, while sodium and potassium hydroxide are particularly preferred.

The compounds of general formula (1) may optionally be converted into the salts thereof, particularly for pharmaceutical use into the pharmacologically acceptable acid addition salts with an inorganic or organic acid. Examples of suitable acids for this purpose include succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The compounds according to the invention may optionally be present as racemates, but may also be obtained as pure enantiomers, i.e. in the (R) or (S) form.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The invention relates to the respective compounds of formula 1 in the form of the pharmacologically acceptable salts thereof as hereinbefore described. These pharmacologically acceptable salts of the compounds of formula 1 may also be present in the form of their respective hydrates (e.g. monohydrates, dihydrates, etc.) as well as in the form of their respective solvates.

By a hydrate of the compound according to the formula 1 is meant, for the purposes of the invention, a crystalline salt of the compound according to formula 1, containing water of crystallisation.

By a solvate of the compound according to formula 1 is meant, for the purposes of the invention, a crystalline salt of the compound according to formula 1, which contains solvent molecules (e.g. ethanol, methanol etc) in the crystal lattice.

The skilled man will be familiar with the standard methods of obtaining hydrates and solvates (e.g. recrystallisation from the corresponding solvent, in the case of solvates, or from water, in the case of hydrates).

Methods of Synthesis

The compounds of general formula (I) may be prepared according to the following general synthesis scheme, wherein the substituents of general formula (I) have the meanings given hereinbefore. These methods are to be understood as being an illustration of the invention without restricting it to the subject-matter thereof.

General Synthesis Scheme

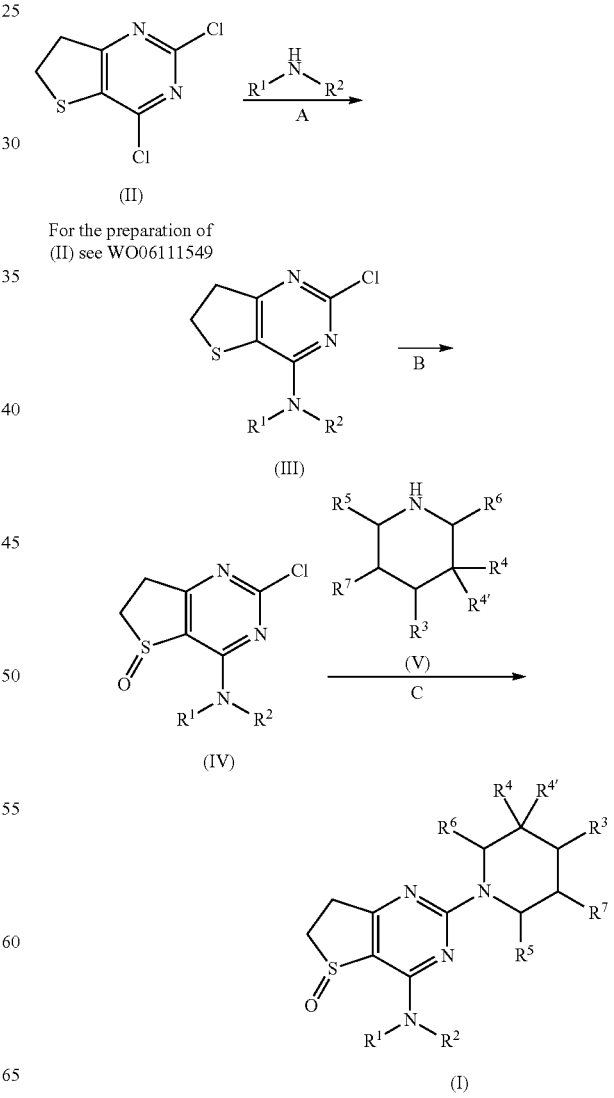

1. SYNTHESIS OF (R)-2-{2-[(R)-4-(4-CHLOROPHENYL)-2-METHYLPIPERAZIN-1-YL]-5-OXO-6,7-DIHYDRO-5H-5λ$^4$-THIENO[3,2-D]PYRIMIDIN-4-YLAMINO}-3-METHYLBUTAN-1-OL

Example 1

1.1 (R)-2-(2-chloro-6,7-dihydrothieno[3,2-d]pyrimidin-4-ylamino)-3-methylbutan-1-ol (III-1)

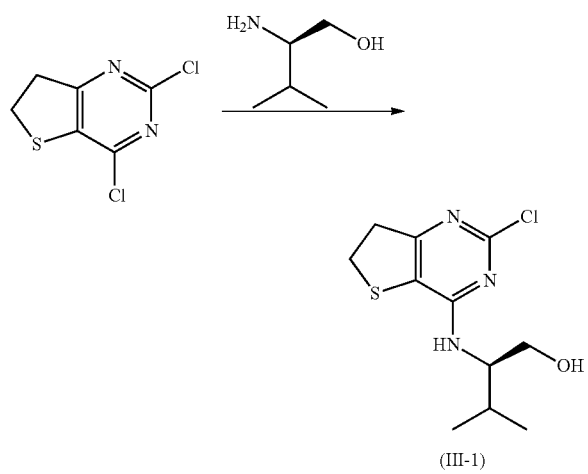

7.2 g 2,4-dichloro-6,7-dihydrothieno[3,2-d]pyrimidine (II) are placed in 36 ml dioxane, then 18 ml diisopropylethylamine and then 6.1 g (R)-(−)-2-amino-3-methyl-1-butanol are added. The reaction mixture is heated to 100° C. until there is no further reaction, and after cooling evaporated down. The residue is treated with petroleum ether/ethyl acetate 9:1 in the ultrasound bath, the solid is suction filtered and dried. 8.3 g (III-1) are obtained as a solid. Analytical HPLC (method A): RT=2.75 min

1.2 (R)-2-(2-chloro-5-oxo-6,7-dihydro-5H-5λ$^4$-thieno[3,2-d]pyrimidin-4-ylamino)-3-methylbutan-1-ol (IV-1)

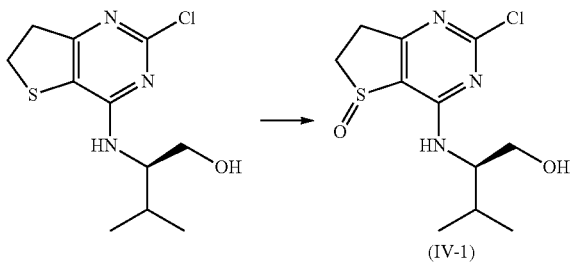

4.1 g S-(−)-1,1'-bi-2-naphthol are placed in 15 ml chloroform under argon, then 0.44 ml titanium(IV)-isopropoxide and 0.54 ml of water are added. The reaction mixture is stirred for 1 hour at ambient temperature. Then a suspension of 4.1 g (III-1) in 107 ml dichloromethane is added. The reaction mixture is cooled to −2° C. and after 30 minutes 2.7 ml tert-butylhydroperoxide 5-6 M in decane are added dropwise. The reaction mixture is stirred at −2° C. until no further reaction takes place, and made basic with NH$_4$OH. The product is extracted with dichloromethane and purified by chromatography (silica gel, ethyl acetate/methanol 100/0 to 86/14). 2.45 g (IV-1) are obtained as a solid.

Analytical HPLC (method A): RT=2.37 min

1.3 (R)-1-(4-chlorophenyl)-3-methylpiperazine (V-1)

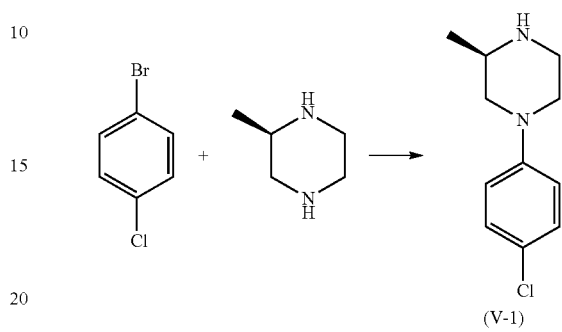

0.068 g 4-bromochlorobenzene, 1 g of (R)-2-methylpiperazine and 1.1 g potassium-tert-butoxide are suspended in 11 ml anhydrous, degassed toluene and heated to 80° C. under argon. 0.055 g tris(dibenzylideneacetone)dipalladium(0) and 0.077 g rac-BINAP are added. The reaction mixture is stirred for 7 hours at 90° C. and mixed with water. The product is extracted with ethyl acetate and purified by chromatography (preparative HPLC, method A). 0.249 g (V-1) are obtained as the trifluoroacetate. Analytical HPLC-MS (method A): RT=1.08 min.

1.4 (R)-2-{2-[(R)-4-(4-chlorophenyl)-2-methylpiperazin-1-yl]-5-oxo-6,7-dihydro-5H-5λ$^4$-thieno[3,2-d]pyrimidin-4-ylamino}-3-methylbutan-1-ol

Example 1

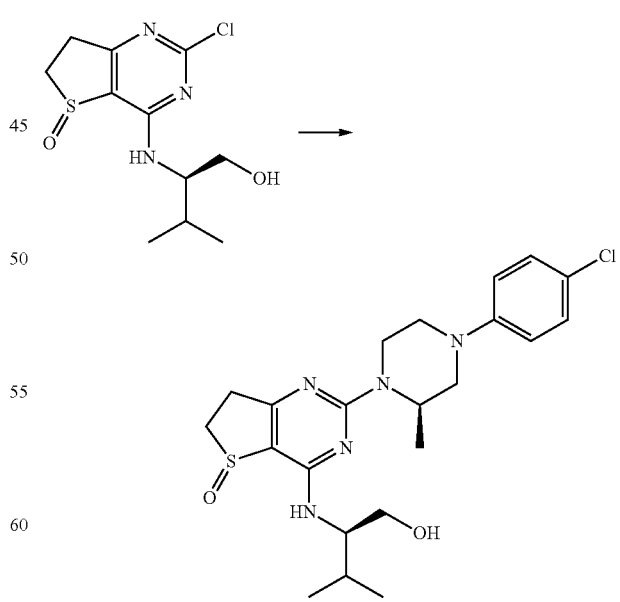

Example 1

0.16 g (IV-1) is placed in 2.5 ml dioxane and 206 μl diisopropylethylamine, mixed with 0.16 g (V-1) (see 1.3) and heated to 140° C. in the microwave until there is no further reaction. The reaction mixture is mixed with water, the product is suction filtered and purified by chromatography (preparative HPLC, method B). 0.03 g of Example 1 are obtained as a solid. Analytical HPLC-MS (method A): RT=1.26 min.

2. SYNTHESIS OF (S)-5-{2-[5-(4-CHLOROPHENYL)-2,5-DIAZABICYCLO[2,2,1]HEPT-2-YL]-5-OXO-6,7-DIHYDRO-5H-5λ⁴-THIENO[3,2-D]PYRIMIDIN-4-YLAMINO}-1-METHYLPIPERIDIN-2-ONE

Example 9

2.1 (S)-5-dibenzylaminopiperidin-2-one

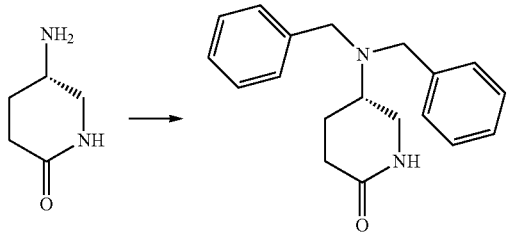 [SMILES: N[C@H]1CCC(=O)NC1 ; O=C1CC[C@H](N(Cc2ccccc2)Cc2ccccc2)CN1]

0.600 g 4-(S)-amino-delta-valerolactam hydrochloride, 0.970 ml benzylbromide and 1.5 g sodium hydrogen carbonate are suspended in 30 ml of ethanol. The reaction mixture is then stirred for 8 hours at 80° C. and then evaporated to dryness. The residue is suspended in water and the product is extracted with dichloromethane and purified by chromatography (silica gel, dichloromethane/methanol 100/0 to 95/5). 0.500 g of the product are obtained as an oil. Analytical HPLC-MS (method A): RT=1.01 min.

2.2 (S)-5-dibenzylamino-1-methylpiperidin-2-one

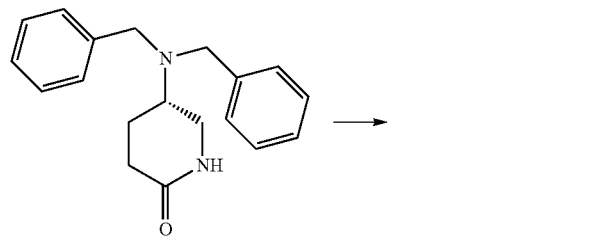

0.500 g (S)-5-dibenzylaminopiperidin-2-one are suspended in 15 ml of tetrahydrofuran. While cooling with the ice bath 0.175 g potassium-tert-butoxide are added. The reaction mixture is then stirred for 30 minutes at ambient temperature. While cooling with the ice bath 0.095 ml methyl iodide are added. The reaction mixture is then stirred for 48 hours at ambient temperature and then mixed with a saturated NaCl solution. The product is extracted with ethyl acetate. 0.450 g of the product are obtained as an oil.
Analytical HPLC-MS (method A): RT=1.07 min.

2.3 (S)-5-amino-1-methylpiperidin-2-one

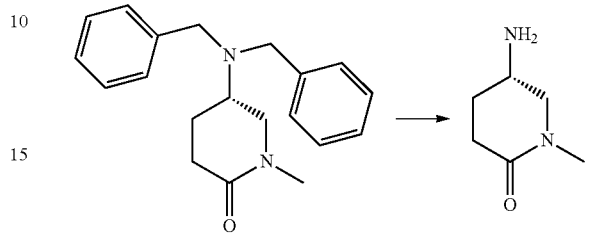

0.450 g (S)-5-dibenzylamino-1-methylpiperidin-2-one are suspended in 25 ml of methanol and hydrogenated with 0.150 g Pd/C 10% at a pressure of 3 bar and a temperature of 60° C. After 16 hours the catalyst is removed by suction filtering and the filtrate is evaporated to dryness. 0.190 g of the product are obtained as an oil. ¹H NMR (400 MHz, DMSO): 2.76 (3H, s).

2.4 (S)-5-(2-chloro-6,7-dihydro-thieno[3,2-d]pyrimidin-4-ylamino)-1-methylpiperidin-2-one (III-2)

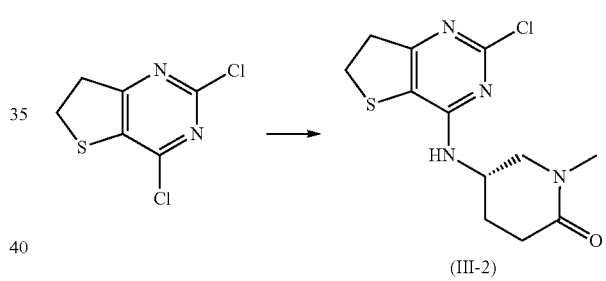

0.27 g (II) are placed in 3 ml dioxane, then 0.45 ml diisopropylethylamine are added followed by 0.25 g (S)-5-amino-1-methylpiperidin-2-one. The reaction mixture is heated to 130° C. until there is no further reaction, and after cooling evaporated down. The product is extracted with dichloromethane and purified by chromatography (preparative HPLC, method A). 0.26 g (III-2) are obtained as a solid. Analytical HPLC-MS (method A): RT=1.06 min.

2.5 (S)-5-(2-chloro-5-oxo-6,7-dihydro-5H-5λ⁴-thieno[3,2-d]pyrimidin-4-ylamino)-1-methylpiperidin-2-one (IV-2)

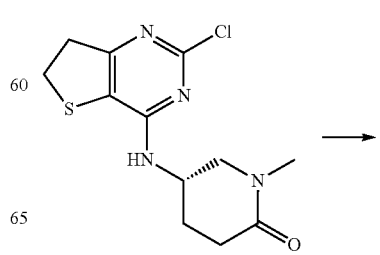

-continued

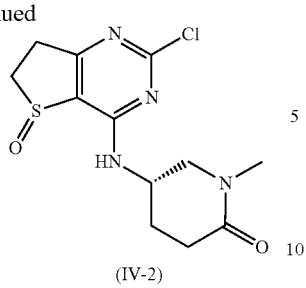

(IV-2)

0.04 g S-(−)-1,1'-bi-2-naphthol are placed in 5 ml chloroform under argon, then 0.02 ml titanium(IV)-isopropoxide and 0.025 ml of water are added. The reaction mixture is stirred for 1 hour at ambient temperature. Then a suspension of 0.2 g (III-2) in 4 ml dichloromethane is added. The reaction mixture is cooled to −5° C. and after 20 minutes 0.12 ml of tert-butylhydroperoxide 5-6 M in decane are added dropwise. The reaction mixture is stirred further at −5° C. until there is no further reaction and made basic with NH$_4$OH. The product is purified by chromatography (silica gel, ethyl acetate/methanol 100/0 to 60/40). 0.09 g (IV-2) are obtained as a solid. Analytical HPLC-MS (method A): RT=0.83 min.

2.6 (S)-5-{2-[5-(4-chlorophenyl)-2,5-diazabicyclo[2,2,1]hept-2-yl]-5-oxo-6,7-dihydro-5H-5λ$^4$-thieno[3,2-d]pyrimidin-4-ylamino}-1-methylpiperidin-2-one Example 9

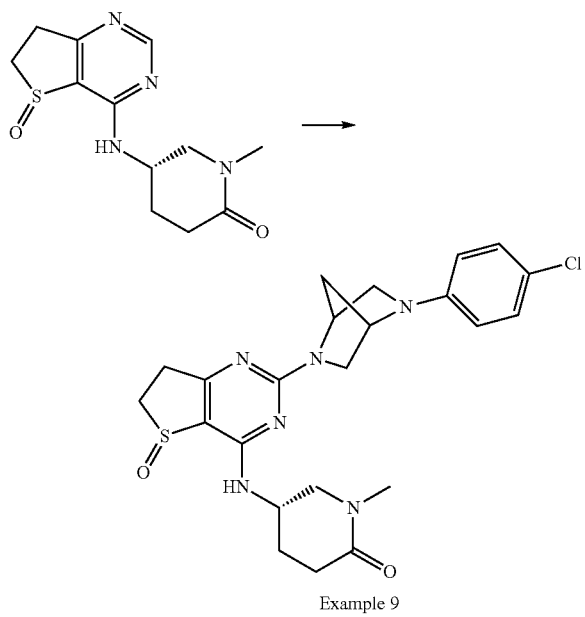

Example 9

0.059 g (IV-2) is placed in 0.5 ml dioxane and 99 µl diisopropylethylamine, mixed with 0.061 g 2-(4-chlorophenyl)-2,5-diazabicyclo[2,2,1]heptane piperazine and heated to 120° C. in the microwave until there is no further reaction. The reaction mixture is mixed with water and the product is extracted with dichloromethane and purified by chromatography (preparative HPLC, method C). The product fractions are made basic with ammonia and extracted with dichloromethane. 0.04 g Example 9 are obtained as a solid.
Analytical HPLC-MS (method A): RT=1.13 min.

3. SYNTHESIS OF {2-[5-(4-BROMOPHENYL)-2,5-DIAZABICYCLO[2,2,1]HEPT-2-YL]-5-OXO-6,7-DIHYDRO-5H-5λ$^4$-THIENO[3,2-D]PYRIMIDIN-4-YL}-(3-FLUOROPHENYL)-AMINE

Example 21

3.1 (2-chloro-6,7-dihydrothieno[3,2-d]pyrimidin-4-yl)-(3-fluorophenyl)-amine (III-3)

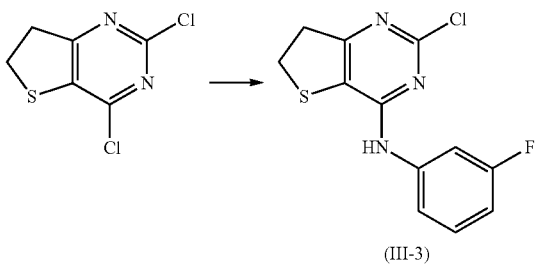 [SMILES: Clc1nc(Cl)c2c(n1)CCS2 ; Fc1cccc(Nc2nc(Cl)nc3c2SCC3)c1 ; "(III-3)"]

(III-3)

4 g (II) are placed in 15 ml dimethylformamide, then 4.5 ml diisopropylethylamine followed by 2.5 ml 3-fluoro-phenylamine are added. The reaction mixture is heated to 120° C. until there is no further reaction and after cooling evaporated down. The residue is mixed with water. The product is extracted with dichloromethane and purified by chromatography (silica gel, petroleum ether/ethyl acetate 80/20 to 60/40). 2.6 g (III-3) are obtained as a solid.

Analytical HPLC (method A): RT=3.27 min.

3.2 2-chloro-5-oxo-6,7-dihydro-5H-5λ$^4$-thieno[3,2-d]pyrimidin-4-yl)-(3-fluorophenyl)-amine (IV-3)

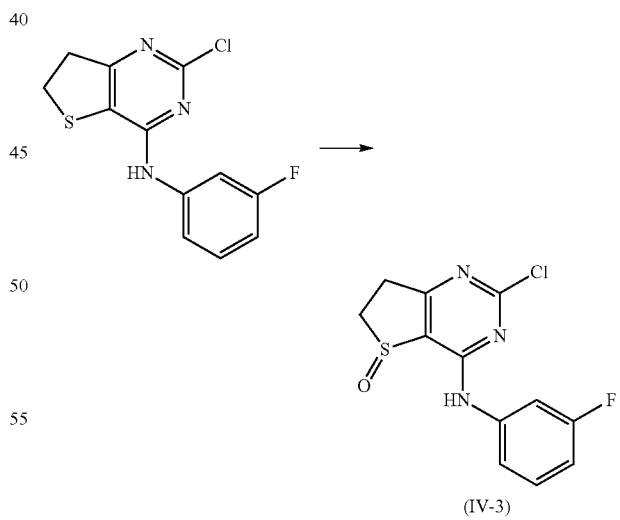

(IV-3)

0.102 g S-(−)-1,1'-bi-2-naphthol are placed in 0.5 ml chloroform under argon, then 0.052 ml titanium(IV) isopropoxide and 0.064 ml of water are added. The reaction mixture is stirred for 45 minutes at ambient temperature. Then a suspension of 0.5 g (III-3) in 25 ml chloroform is added. The reaction mixture is cooled to −2°/−4° C. and after 20 minutes 0.323 ml tert-butylhydroperoxide 5-6 M in decane are added dropwise. The reaction mixture is stirred further at −2/−4° C. until there is no further reaction and mixed with water. The product is extracted with dichloromethane and purified by chromatography (silica gel, dichloromethane/methanol 100/0 to 95/5). 0.47 g (IV-3) are obtained as a solid.

Analytical HPLC-MS (method A): RT=1.15 min.

3.3 2-(4-bromophenyl)-2,5-diazabicyclo[2,2,1]heptane (V-2)

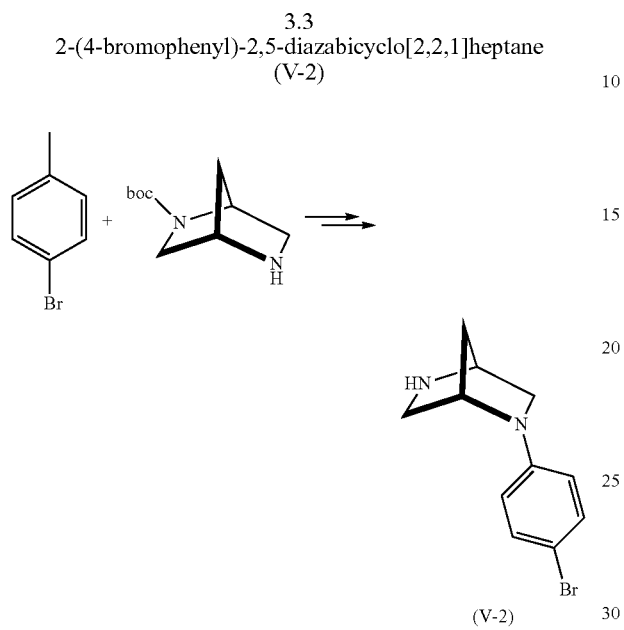

5.5 g of 2,5-diazabicyclo[2,2,1]heptane-2-BOC, 7.9 g 4-bromoiodobenzene, 0.77 g tris(dibenzylideneacetone)dipalladium(0), 0.79 g rac-BINAP, 3.8 g sodium-tert-butoxide and 10.4 g 1,4,7,10,13,16-hexaoxacyclooctadecane are suspended in 55 ml anhydrous, degassed tetrahydrofuran and stirred under argon at ambient temperature until there is no further reaction. The reaction mixture is evaporated to dryness and mixed with water. The product is extracted with dichloromethane and purified by chromatography (silica gel dichloromethane/methanol 100/0 to 0/100). 2.28 g 5-(4-bromophenyl)-2,5-diazabicyclo[2,2,1]heptane-2-BOC are obtained. The product obtained and 8.6 ml trifluoroacetic acid are suspended in 54 ml dichloromethane and stirred at ambient temperature until there is no further reaction. The reaction mixture is then evaporated to dryness. The residue is suspended in diethyl ether and the solid is suction filtered. 2.34 g (V-2) are obtained as the trifluoroacetate.

Analytical HPLC-MS (method A): RT=1.06 min.

3.4 {2-[5-(4-bromophenyl)-2,5-diazabicyclo[2,2,1]hept-2-yl]-5-oxo-6,7-dihydro-5H-5λ⁴-thieno[3,2-d]pyrimidin-4-yl}-(3-fluorophenyl)-amine Example 21

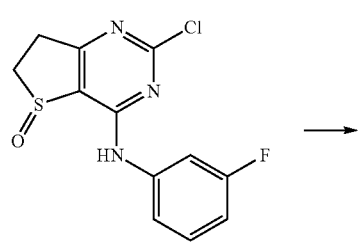

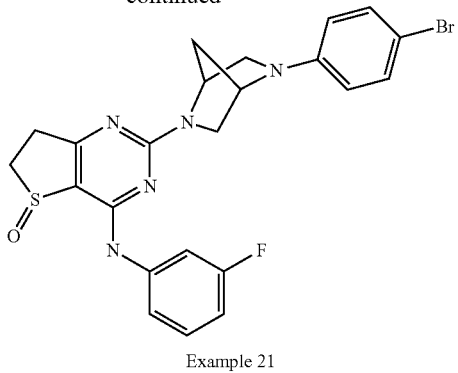

Example 21

0.179 g (IV-3) is placed in 1.6 ml N-methyl-2-pyrrolidone (NMP). 0.32 ml diisopropylethylamine and 0.26 g (V-2) (see 3.3) are added. The reaction mixture is heated in the microwave at 120° C. until there is no further reaction. The product is purified by chromatography (preparative HPLC, method D). 0.13 g of Example 21 are obtained as a solid. Analytical HPLC-MS (method A): RT=1.34 min.

4. SYNTHESIS OF (1-{2-[5-(4-FLUOROPHENYL)-2,5-DIAZABICYCLO[2,2,1]HEPT-2-YL]-5-OXO-6,7-DIHYDRO-5H-5λ⁴-THIENO[3,2-D]PYRIMIDIN-4-YLAMINO}-CYCLOPROPYL)-METHANOL

Example 24

4.1 tert-butyl (1-hydroxymethylcyclopropyl)-carbamidate

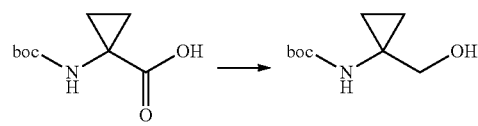

1 g 1-(BOC-amino)-cyclopropanecarboxylic acid is dissolved in 20 ml dimethoxyethane and cooled to −70° C. Then 0.65 ml of N-methylmorpholine are added. 0.71 ml of isobutyl chloroformate in 5 ml dimethoxyethane are added dropwise. The reaction mixture is heated to −5° C. The precipitate is suction filtered. The eluate is cooled to −15° C. and 0.303 g sodium borohydride are slowly added. The reaction mixture is then stirred for 30 minutes at ambient temperature, mixed with water and the product is extracted with dichloromethane. The organic phase is dried and evaporated to dryness. 1.04 g product are obtained as a solid.

$^1$H NMR (400 MHz, DMSO): 1.36 (9H, s); 0.61 (2H, t); 0.52 (2H, t).

4.2 1-aminocyclopropanemethanol

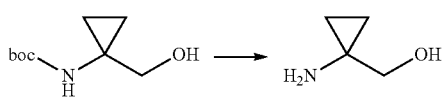

1.04 g tert-butyl (1-hydroxymethylcyclopropyl)-carbamidate are placed in 5 ml dioxane. 2.5 ml HCl in dioxane (4 mol/l) are added dropwise. The reaction mixture is stirred for 15 h at ambient temperature. The solvent is evaporated down by half and the precipitated solid is suction filtered. 0.5 g product are obtained as the hydrochloride.

$^1$H NMR (400 MHz, DMSO): 5.27 (1H, t); 0.91 (2H, t); 0.71 (2H, t).

4.3 [1-(2-chloro-6,7-dihydrothieno[3,2-d]pyrimidin-4-ylamino)-cyclopropyl]-methanol (III-4)

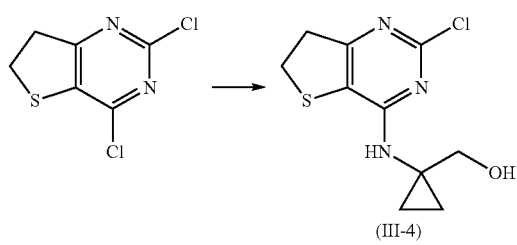

(III-4)

1.4 g (II) are placed in 10 ml dioxane, then 3.6 ml diisopropylethylamine followed by 1 g of 1-aminocyclopropanemethanol (see 4.2) are added. The reaction mixture is heated at 160° C. until there is no further reaction, and after cooling evaporated down. The residue is treated with cyclohexane/ethyl acetate (8:2) in the ultrasound bath and the solid is suction filtered and dried. 1.24 g (III-4) are obtained as a solid.

Analytical HPLC-MS (method A): RT=1.01 min.

4.4 [1-(2-chloro-5-oxo-6,7-dihydro-5H-5λ$^4$-thieno[3,2-d]pyrimidin-4-ylamino)-cyclopropyl]-methanol (IV-4)

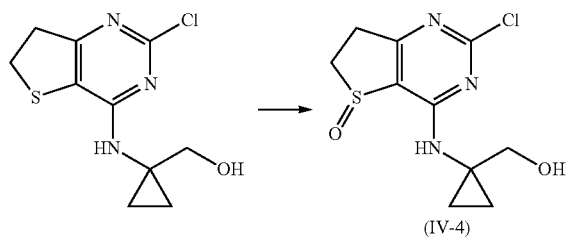

(IV-4)

0.28 g S-(−)-1,1'-bi-2-naphthol are placed in 20 ml chloroform under argon, then 0.14 ml titanium(IV) isopropoxide and 0.17 ml of water are added. The reaction mixture is stirred for 1 hour at ambient temperature. Then a suspension of 1.2 g (III-4) in 40 ml dichloromethane and 2 ml of methanol is added. The reaction mixture is cooled to −5° C. and after 30 minutes 0.91 ml tert-butylhydroperoxide 5-6 M in decane are added dropwise. The reaction mixture is stirred further at −5° C. until there is no further reaction and made basic with NH$_4$OH. The aqueous phase is washed with dichloromethane and freeze-dried. 1 g (IV-4) is obtained as a solid. Analytical HPLC-MS (method A) RT=0.85 min.

4.5 (1-{2-[5-(4-fluorophenyl)-2,5-diazabicyclo[2,2,1]hept-2-yl]-5-oxo-6,7-dihydro-5H-5λ$^4$-thieno[3,2-d]pyrimidin-4-ylamino}-cyclopropyl)-methanol Example 24

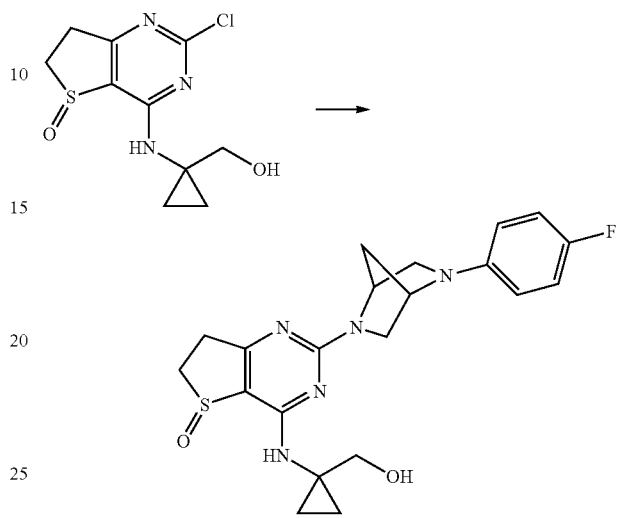

Example 24

Starting from 0.1 g (IV-4) (see 4.4) and 0.115 g-(4-fluorophenyl)-2,5-diazabicyclo[2,2,1]heptane, 0.142 g of Example 24 are prepared analogously to Example 21 (see 3.4). The product is purified by chromatography (preparative HPLC, method D). 0.142 g Example 24 are obtained as a solid. Analytical HPLC-MS (method A): RT=1.08 min.

5. SYNTHESIS OF (1-{2-[3-(4-BROMOPHENYL)-3,8-DIAZABICYCLO[3.2.1]OCT-8-YL]-5-OXO-6,7-DIHYDRO-5H-5λ$^4$-THIENO[3,2-D]PYRIMIDIN-4-YLAMINO}-CYCLOPROPYL)-METHANOL TRIFLUORACETAT

Example 28

5.1 3-(4-bromophenyl)-3,8-diazabicyclo[3.2.1]octane (V-3)

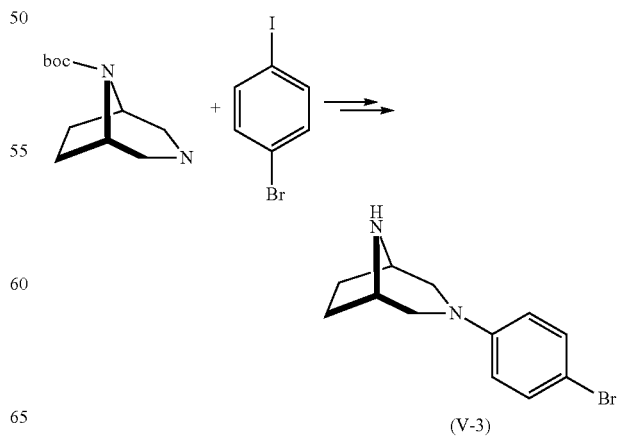

(V-3)

0.300 g 8-BOC-3,8-diazabicyclo[3.2.1]octane, 0.402 g 4-bromoiodobenzene, 0.035 g tris(dibenzylideneacetone)dipalladium(0), 0.064 g Xantphos and 0.660 g caesium carbonate are heated to 110° C. in 6 ml anhydrous, degassed dioxane and under argon for 42 hours. The reaction mixture is filtered through Celite and the eluate is combined with a saturated sodium chloride solution. The product is extracted with ethyl acetate. 0.610 g (1R.5S)-3-(4-bromo-phenyl)-3,8-diazabicyclo[3.2.1]octane-8-BOC are obtained.

The product obtained is further processed analogously to (V-2) (see 3.3). 0.520 g (V-3) are obtained as the trifluoroacetate. Analytical HPLC-MS (method B): RT=1.26 min.

5.2 (1-{2-[3-(4-bromophenyl)-3,8-diazabicyclo[3.2.1]oct-8-yl]-5-oxo-6,7-dihydro-5H-5λ⁴-thieno[3,2-d]pyrimidin-4-ylamino}-cyclopropyl)-methanol trifluoroacetate Example 28

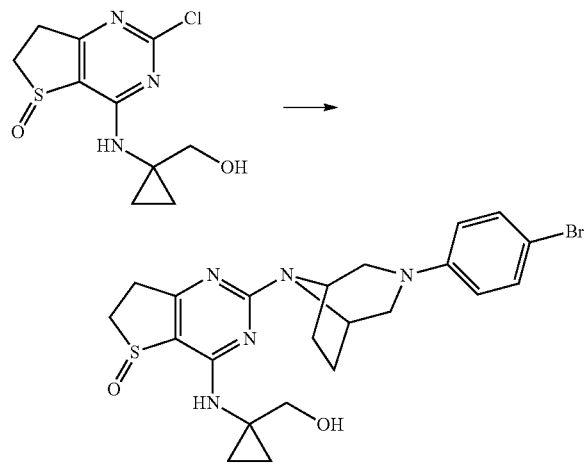

Example 28

Starting from 0.1 g (IV-4) (see 4.4) and 0.18 g (V-3) (see 5.1) 0.052 g Example 28 are prepared as the trifluoroacetate analogously to Example 21 (see 3.4). The product is purified by chromatography (preparative HPLC, method E).
Analytical HPLC-MS (method B): RT=1.37 min.

6. SYNTHESIS OF [2-(5-BENZOXAZOL-2-YL-2,5-DIAZABICYCLO[2,2,1]HEPT-2-YL)-5-OXO-6,7-DIHYDRO-5H-5λ⁴-THIENO[3,2-D]PYRIMIDIN-4-YL]-(TETRAHYDROPYRAN-4-YL)-AMINE

Example 29

6.1 (2-chloro-6,7-dihydrothieno[3,2-d]pyrimidin-4-yl)-(tetrahydropyran-4-yl)-amine (III-5)

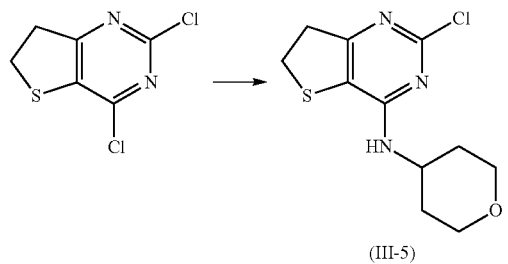 [SMILES: Clc1nc(Cl)c2c(n1)CCS2 ; Clc1nc2c(c(NC3CCOCC3)n1)SCC2 ; "(III-5)"]

0.68 g (II) are placed in 6 ml dioxane, then 1.72 ml diisopropylethylamine followed by 0.6 g 4-aminotetrahydropyran are added. The reaction mixture is heated at 130° C. until there is no further reaction and after cooling evaporated down. The product is treated with water in the ultrasound bath, suction filtered and dried. 0.66 g (III-5) are obtained as a solid.
Analytical HPLC-MS (method A): RT=1.08 min.

6.2 (2-chloro-5-oxo-6,7-dihydro-5H-5λ⁴-thieno[3,2-d]pyrimidin-4-yl)-(tetrahydropyran-4-yl)-amine (IV-5)

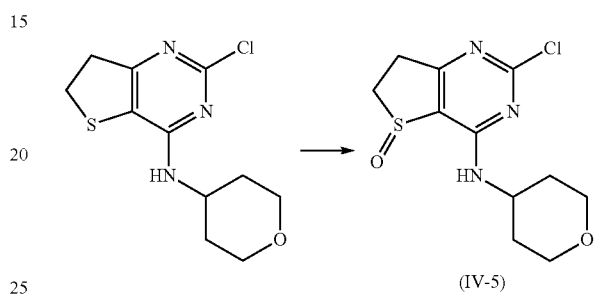

0.14 g S-(−)-1,1'-bi-2-naphthol are placed in 5 ml chloroform under argon, then 0.072 ml titanium(IV) isopropoxide and 0.087 ml of water are added. The reaction mixture is stirred for 45 minutes at ambient temperature. Then a suspension of 0.66 g (III-5) in 25 ml chloroform is added. The reaction mixture is cooled to −10° C. and after 60 minutes 0.444 ml of tert-butylhydroperoxide 5-6 M in decane are added dropwise. The reaction mixture is stirred further at −10 to −4° C. until there is no further reaction and mixed with water. The product is extracted with dichloromethane and purified by chromatography (silica gel, ethyl acetate/methanol 100/0 to 80/20). 0.42 g (IV-5) are obtained as a solid.
Analytical HPLC-MS (method A): RT=0.94 min.

6.3 (1S.4S)-2-(2,5-diazabicyclo[2,2,1]hept-2-yl-benzoxazole (V-4)

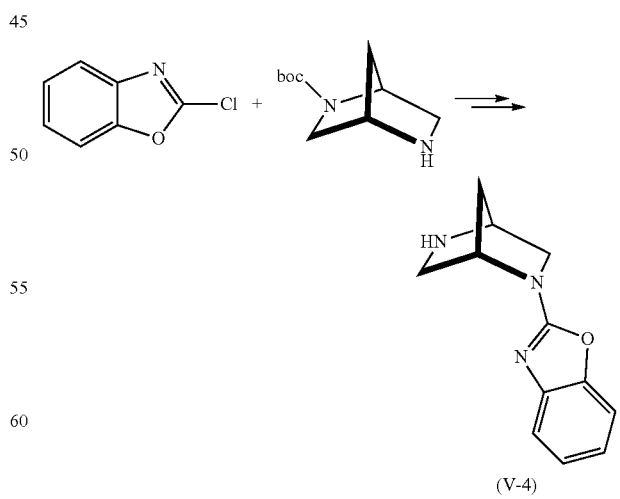

0.145 ml 2-chlorobenzoxazols are placed in 5 ml chloroform, then 0.225 ml diisopropylethylamine followed by 0.250 g (1S.4S)-2,5-diazabicyclo[2,2,1]heptane-2-BOC are added. The reaction mixture is stirred for 15 hours at ambient temperature, then mixed with water and the product is extracted with chloroform. 0.370 g (V-4) are obtained as a solid. The product obtained is further processed analogously to (V-2) (see 3.3). 0.320 g (V-4) are obtained as the trifluoroacetate. Analytical HPLC-MS (method B): RT=1.02 min.

6.4 [2-(5-benzoxazol-2-yl-2,5-diazabicyclo[2,2,1]hept-2-yl)-5-oxo-6,7-dihydro-5H-5λ⁴-thieno[3,2-d]pyrimidin-4-yl]-(tetrahydropyran-4-yl)-amine Example 29

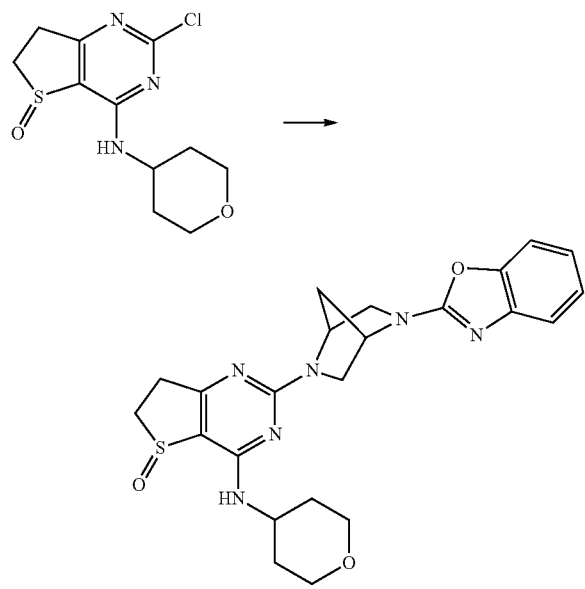

Example 29

Starting from 0.17 g (IV-5) (see 6.2) and 0.205 g (V-4) (see 6.3) 0.183 g of Example 29 are prepared analogously to Example 21 (see 3.4).

Analytical HPLC-MS (method A): RT=1.05 min.

7. SYNTHESIS OF {1-[2-(5,6-DIHYDRO-8H-[1,2,4]TRIAZOLO[4,3-A]PYRAZIN-7-YL)-5-OXO-6,7-DIHYDRO-5H-5λ⁴-THIENO[3,2-D]PYRIMIDIN-4-YLAMINO]-CYCLOPROPYL}-METHANOL TRIFLUORACETATE

Example 33

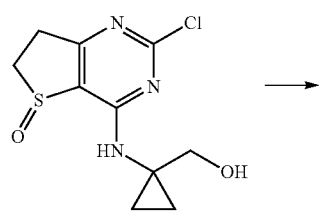

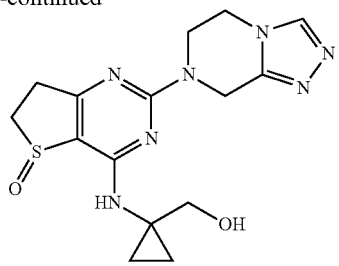

Example 33

(IV-4) (see 4.4) (0.1 mmol) is placed in 750 µl N-methyl-2-pyrrolidone (NMP) and 50 µl diisopropylethylamine, mixed with a solution of 5,6,7,8-tetrahydro-[1,2,4]triazolo[4,3-a]pyrazine (0.1 mmol) in 400 µl NMP and heated for 30 min at 120° C. in the microwave. Then 600 µL DMF are added, the reaction solution is purified by preparative HPLC-MS (method A) and the product fractions are freeze-dried. Example 33 is obtained as the trifluoroacetate. Analytical HPLC-MS (method C): RT=1.62 min.

8. SYNTHESIS OF [2-(5,6-DIHYDRO-8H-[1,2,4]TRIAZOLO[4,3-A]PYRAZIN-7-YL)-5-OXO-6,7-DIHYDRO-5H-5λ⁴-THIENO[3,2-D]PYRIMIDIN-4-YL]-(TETRAHYDRO-PYRAN-4-YL)-AMINE TRIFLUOROACETATE

Example 37

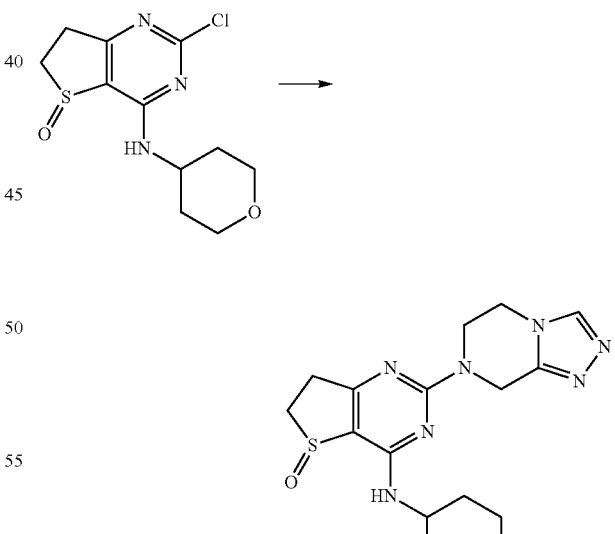

Example 37

Starting from (IV-5) (see 6.2) and 5,6,7,8-tetrahydro-[1,2,4]triazolo[4,3-a]pyrazine Example 37 is prepared and purified as the trifluoroacetate analogously to Example 33 (see 7). Analytical HPLC-MS (method C): RT=1.35 min.

9. SYNTHESIS OF (3-FLUOROPHENYL)-{2-[3-(4-FLUOROPHENYL)-5,6-DIHYDRO-8H-[1,2,4]TRIAZOLO[4,3-A]PYRAZIN-7-YL]-5-OXO-6,7-DIHYDRO-5H-5λ⁴-THIENO[3,2-D]PYRIMIDIN-4-YL}-AMINE TRIFLUOROACETATE

Example 39

9.1 3-(4-fluorophenyl)-5,6,7,8-tetrahydro-[1,2,4]triazolo[4,3-a]pyrazine (V-5)

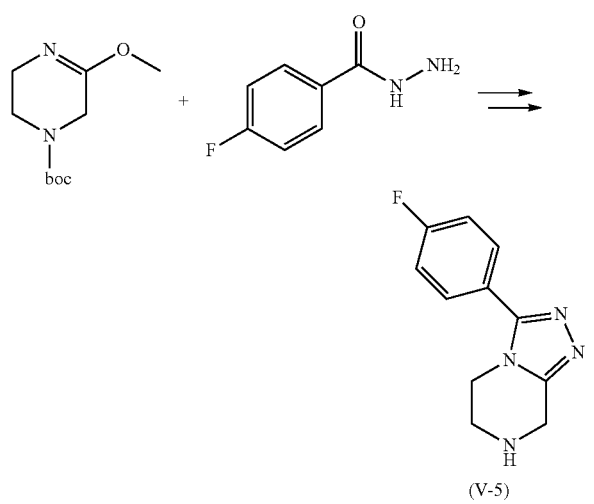

(V-5)

2.9 g 5-methoxy-3,6-dihydro-2H-pyrazine-1-BOC (EP1477490), 2.1 g 4-fluorobenzhydrazide are suspended in 50 ml of ethanol and 50 ml glacial acetic acid. The reaction mixture is heated to 70° C. until there is no further reaction, then evaporated to dryness. The residue is suspended in 10 ml dichloromethane and 10 ml trifluoroacetic acid, stirred for 4 hours at 40° C. and evaporated to dryness. The residue is suspended in diethyl ether and the solid is suction filtered. 3.1 g (V-5) are obtained as the trifluoroacetate.

¹H NMR (400 MHz, DMSO): 4.61 (2H, s); 4.34 (2H, t); 3.61 (2H, t).

9.2 (3-fluorophenyl)-{2-[3-(4-fluorophenyl)-5,6-dihydro-8H-[1,2,4]triazolo[4,3-a]pyrazin-7-yl]-5-oxo-6,7-dihydro-5H-5λ⁴-thieno[3,2-d]pyrimidin-4-yl}-amine

Example 39

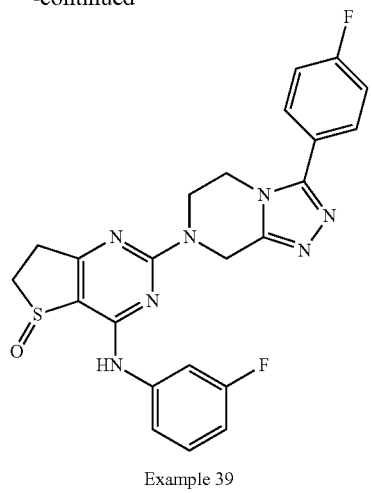

Example 39

Starting from (IV-3) (see 3.2) and (V-5) (see 9.1) Example 39 is prepared and purified as the trifluoroacetate analogously to Example 33 (see 7).

Analytical HPLC-MS (method C): RT=1.89 min.

10. SYNTHESIS OF {2-[3-(3,4-DICHLORBENZYL)-5,6-DIHYDRO-8H-[1,2,4]TRIAZOLO[4,3-A]PYRAZIN-7-YL]-5-OXO-6,7-DIHYDRO-5H-5λ⁴-THIENO[3,2-D]PYRIMIDIN-4-YL}-(3-FLUOROPHENYL)-AMINE TRIFLUOROACETATE

Example 40

10.1 3-(3,4-Dichlorobenzyl)-5,6,7,8-tetrahydro-[1,2,4]triazolo[4,3-a]pyrazine (V-6)

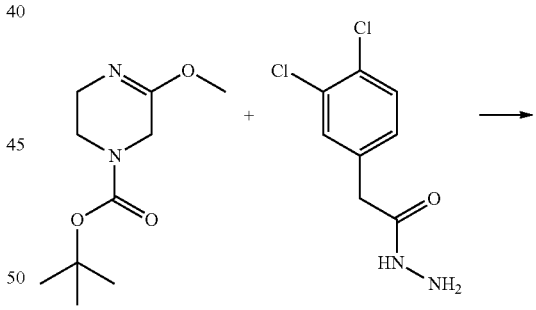

(V-6)

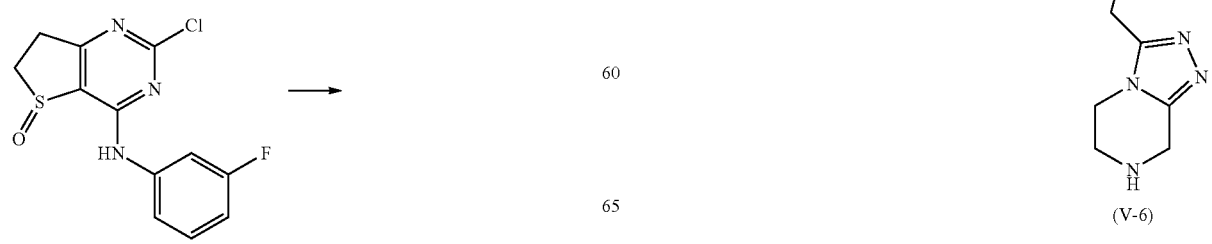

Starting from 2.9 g 5-methoxy-3,6-dihydro-2H-pyrazin-1-BOC (EP1477490), and 3 g (3,4-dichlorophenyl)-acetic acid hydrazide analogously to (V-5) (see 9.1), 3.9 g (V-6) are obtained as the trifluoroacetate.

$^1$H NMR (400 MHz, DMSO): 4.51 (2H, s); 4.22 (2H, s); 4.03 (2H, t); 3.57 (2H, t).

10.2 {2-[3-(3,4-dichlorobenzyl)-5,6-dihydro-8H-[1,2,4]triazolo[4,3-a]pyrazin-7-yl]-5-oxo-6,7-dihydro-5H-5λ$^4$-thieno[3,2-d]pyrimidin-4-yl}-(3-fluorophenyl)-amine Example 40

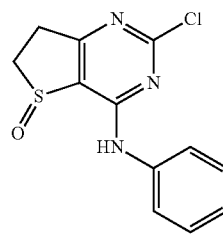

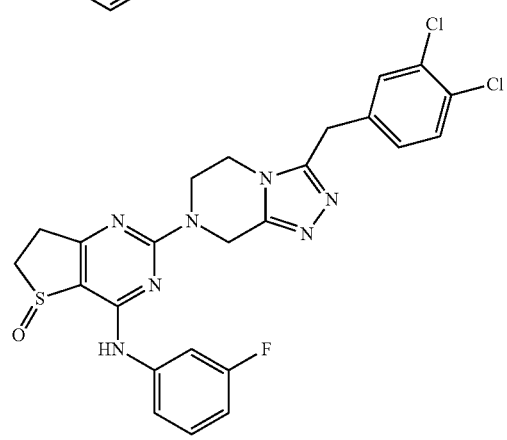

Example 40

Starting from (IV-3) (see 3.2) and (V-6) (see 10.1) Example 40 is prepared and purified as the trifluoroacetate analogously to Example 33 (see 7).
Analytical HPLC-MS (method C): RT=2.02 min.

11. SYNTHESIS OF [2-(5,6-DIHYDRO-8H-[1,2,4]TRIAZOLO[4,3-A]PYRAZIN-7-YL)-5-OXO-6,7-DIHYDRO-5H-5λ$^4$-THIENO[3,2-D]PYRIMIDIN-4-YL]-(3-FLUOROPHENYL)-AMINE TRIFLUOROACETATE

Example 41

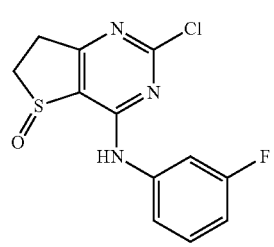

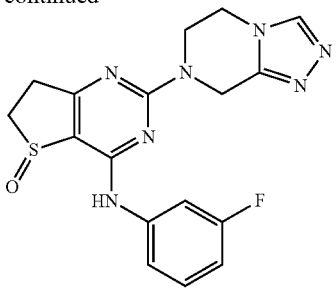

Example 41

Starting from (IV-3) (see 3.2) and 5,6,7,8-tetrahydro-[1,2,4]triazolo[4,3-a]pyrazine Example 41 is prepared and purified as the trifluoroacetate analogously to Example 33 (see 7).
Analytical HPLC-MS (method C): RT=1.6 min.

12. SYNTHESIS OF (R)-2-[2-(5,6-DIHYDRO-8H-[1,2,4]TRIAZOLO[4,3-A]PYRAZIN-7-YL)-5-OXO-6,7-DIHYDRO-5H-5λ$^4$-THIENO[3,2-D]PYRIMIDIN-4-YLAMINO]-3-METHYL-BUTAN-1-OL TRIFLUOROACETATE

Example 45

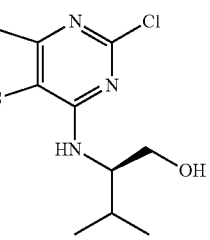

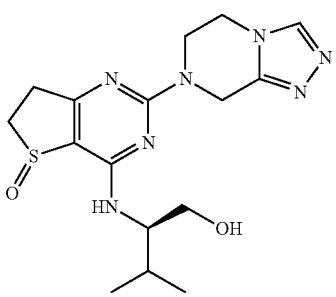

Example 45

Starting from (IV-1) (see 1.2) and 5,6,7,8-tetrahydro-[1,2,4]triazolo[4,3-a]pyrazine Example 45 is prepared and purified as the trifluoroacetate analogously to Example 33 (see 7).
Analytical HPLC-MS (method C): RT=1.35 min.

13. SYNTHESIS OF MORPHOLIN-4-YL-{7-[5-OXO-4-(TETRAHYDROPYRAN-4-YLAMINO)-6,7-DIHYDRO-5H-5λ⁴-THIENO[3,2-D]PYRIMIDIN-2-YL]-5,6,7,8-TETRAHYDROIMIDAZO[1,2-a]PYRAZIN-2-YL}-METHANONE

Example 48

13.1 7-[5-oxo-4-(tetrahydropyran-4-ylamino)-6,7-dihydro-5H-5λ⁴-thieno[3,2-d]pyrimidin-2-yl]-5,6,7,8-tetrahydroimidazo[1,2-a]pyrazine-2-carboxylic acid

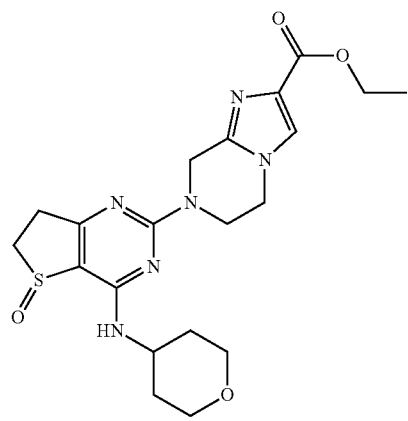

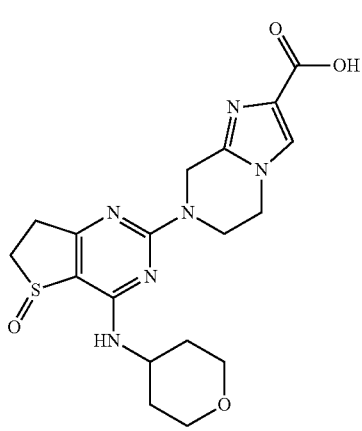

1.18 g Example 34 are suspended in 34.7 ml of ethanol and 9 ml of 1N NaOH are added. The reaction mixture is stirred for 12 hours at ambient temperature, neutralised with 1N HCl and evaporated to dryness. The product is purified by preparative HPLC (method B). 550 mg product are obtained as a solid. Analytical HPLC-MS (method D): RT=0.36 min.

13.2 Morpholin-4-yl-{7-[5-oxo-4-(tetrahydropyran-4-ylamino)-6,7-dihydro-5H-5λ⁴-thieno[3,2-d]pyrimidin-2-yl]-5,6,7,8-tetrahydroimidazo[1,2-a]pyrazin-2-yl}-methanone

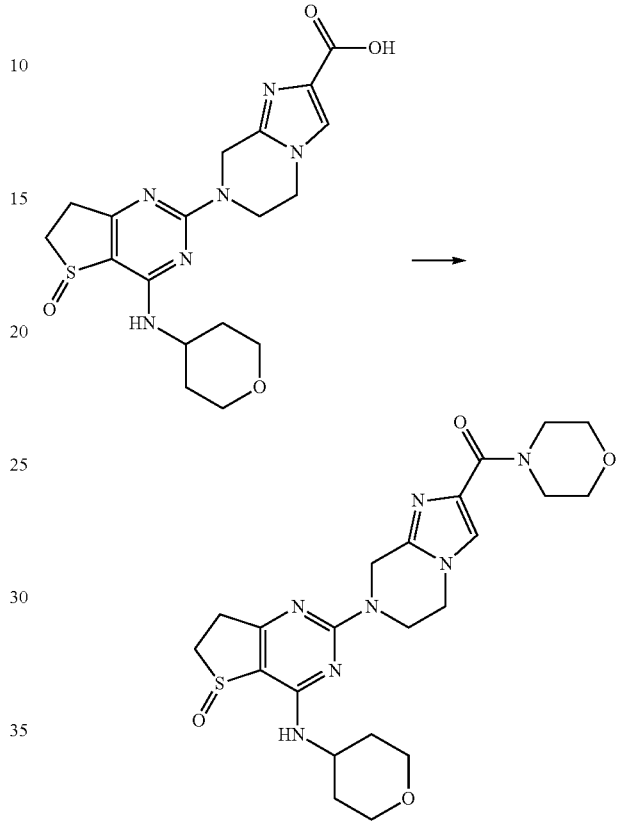

Example 48

50 mg of 7-[5-oxo-4-(tetrahydropyran-4-ylamino)-6,7-dihydro-5H-5λ⁴-thieno[3,2-d]pyrimidin-2-yl]-5,6,7,8-tetrahydroimidazo[1,2-a]pyrazine-2-carboxylic acid (see 13.1) are placed in 2 ml dimethylformamide, then 66 µl diisopropylethylamine and 54.2 mg O-(7-azabenzotriazol-1-yl-)-N,N,N',N'-tetramethyluronium hexafluorophosphate (HATU) are added. After 15 min a suspension of 11.4 mg morpholine in 300 µl dimethylformamide is added. The reaction mixture is stirred at ambient temperature until there is no further reaction, and the product is purified directly by preparative HPLC (method B). 40 mg of Example 48 are obtained as a solid. Analytical HPLC-MS (method D): RT=0.79 min.

Methods of Chromatography

The Example compounds prepared using the synthesis scheme shown hereinbefore were characterised by the following chromatographic methods, which, if they were carried out, are individually specified in Tables B, C and D.
Analytical HPLC-MS, Method A Waters ZMD mass spectrometer (positive ionisation (ESI+)), Alliance 2690/2695 HPLC (diode array detector, wavelength range: 210 to 500 nm), Waters 2700 Autosampler, Waters 996/2996.
A: water with 0.10% TFA
B: acetonitrile with 0.10% TFA

| time in min | % A | % B | flow rate in ml/min |
|---|---|---|---|
| 0.00 | 95 | 5 | 2.50 |
| 0.20 | 95 | 5 | 2.50 |
| 1.50 | 2 | 98 | 2.50 |
| 1.70 | 2 | 98 | 2.50 |
| 1.90 | 95 | 5 | 2.50 |
| 2.20 | 95 | 5 | 2.50 |

The stationary phase used is a Merck Chromolith™ Flash RP-18e column, 4.6 mm×25 mm (column temperature: constant at 25° C.).
Analytical HPLC-MS, Method B
Waters ZMD mass spectrometer (positive ionisation (ESI+)), Alliance 2690/2695 HPLC (diode array detector, wavelength range: 210 to 500 nm), Waters 2700 Autosampler, Waters 996/2996.
A: water with 0.10% TFA
B: acetonitrile with 0.10% TFA

| time in min | % A | % B | flow rate in ml/min |
|---|---|---|---|
| 0.00 | 95 | 5 | 2.80 |
| 0.30 | 95 | 5 | 2.80 |
| 1.60 | 2 | 98 | 2.80 |
| 1.90 | 2 | 98 | 2.80 |
| 2.00 | 95 | 5 | 2.50 |

The stationary phase used is a Merck Chromolith™ Flash RP-18e column, 3 mm×100 mm (column temperature: constant at 25° C.).
Analytical HPLC-MS, Method C:
Waters ZQ2000 mass spectrometer (positive ionisation (ESI+)), HP1100 HPLC (DAD, wavelength range: 210 to 500 nm), and Gilson 215 Autosampler.
A: water with 0.10% TFA
B: acetonitrile with 0.10% TFA

| time in min | % A | % B | flow rate in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

The stationary phase used is a Sunfire C18 column, 4.6×50 mm, 3.5 μm, column temperature 40° C.
Analytical HPLC-MS, Method D
Waters ZMD mass spectrometer (positive ionisation (ESI+)), Alliance 2690/2695 HPLC (diode array detector, wavelength range: 210 to 500 nm), Waters 2700 Autosampler, Waters 996/2996.
A: water with 0.10% $NH_3$
B: acetonitrile with 0.10% $NH_3$

| time in min | % A | % B | flow rate in ml/min |
|---|---|---|---|
| 0.00 | 95 | 5 | 3.00 |
| 0.20 | 95 | 5 | 3.00 |
| 1.50 | 2 | 98 | 3.00 |
| 1.90 | 2 | 98 | 3.00 |
| 2.00 | 2 | 98 | 3.00 |

The stationary phase used is Waters, X-Bridge, C18, 3.5 nm, 4.6×20 mm. Ambient temperature
Preparative HPLC-MS, Method A
Waters ZQ2000 mass spectrometer (positive ionisation (ESI+)), HP1100 HPLC (DAD, wavelength range: 210-500 nm), and Gilson 215 Autosampler.
A: water with 0.10% TFA
B: acetonitrile

| time in min | % A | % B | flow rate in ml/min |
|---|---|---|---|
| 0.00 | 90 | 10 | 50 |
| 1.50 | 90 | 10 | 50 |
| 8.00 | 40 | 60 | 50 |
| 10.00 | 40 | 60 | 50 |
| 11.00 | 90 | 10 | 50 |

The stationary phase used is a Sunfire C18 column, 30×100 mm, 5 μm, ambient temperature.
Preparative HPLC, Method A
Gilson HPLC with Gilson UV-VIS-155 detector, 231 XL sampling injector.
The wavelength given is the substance-specific UV maximum.
A: water with 0.13% TFA
B: acetonitrile with 0.1% TFA

| time in min | % A | % B | flow rate in ml/min |
|---|---|---|---|
| 0.00 | 90 | 10 | 120 |
| 3.60 | 90 | 10 | 120 |
| 17.80 | 0 | 100 | 120 |
| 22.00 | 0 | 100 | 120 |
| 23.00 | 90 | 10 | 120 |
| 26.50 | 90 | 10 | 120 |

The stationary phase used is a Microsorb RP 18 column, 8 μm, 41.4×250 mm, ambient temperature.
Preparative HPLC, Method B
Gilson HPLC with Gilson UV-VIS-155 detector, 231 XL sampling injector.
The wavelength given is the substance-specific UV maximum.
A: water with 0.15% ammonia 35%
B: acetonitrile with 0.15% ammonia 35%

| time in min | % A | % B | flow rate in ml/min |
|---|---|---|---|
| 0.00 | 90 | 10 | 120 |
| 3.00 | 90 | 10 | 120 |
| 15.00 | 0 | 100 | 120 |
| 18.00 | 0 | 100 | 120 |
| 18.50 | 90 | 10 | 120 |
| 21.00 | 90 | 10 | 120 |

The stationary phase used is a Varian Xbridge C 18 column, 5 μm, 50×162 mm, ambient temperature.
Preparative HPLC, Method C
Gilson HPLC with Gilson UV-VIS-155 detector, 231 XL sampling injector.
The wavelength given is the substance-specific UV maximum.
A: water with 0.13% TFA
B: acetonitrile with 0.1% TFA

| time in min | % A | % B | flow rate in ml/min |
|---|---|---|---|
| 0.00 | 95 | 5 | 165 |
| 1.30 | 95 | 5 | 165 |
| 8.90 | 2 | 98 | 165 |
| 10.00 | 2 | 98 | 165 |
| 10.50 | 95 | 5 | 165 |
| 11.60 | 95 | 5 | 165 |

The stationary phase used is a Microsorb RP 18 column, 8 μm, 50×65 mm, ambient temperature.

Preparative HPLC, Method D

Gilson HPLC with Gilson UV-VIS-155 detector, 231 XL sampling injector.

The wavelength given is the substance-specific UV maximum.

A: water with 0.1% ammonia 35%
B: acetonitrile

| time in min | % A | % B | flow rate in ml/min |
|---|---|---|---|
| 0.00 | 95 | 5 | 180 |
| 1.40 | 95 | 5 | 180 |
| 17.00 | 2 | 98 | 180 |
| 18.50 | 2 | 98 | 180 |
| 18.70 | 95 | 5 | 180 |
| 20.-50 | 95 | 5 | 180 |

The stationary phase used is a Pursuit XRS RP 18 column, 10 μm, 50×150 mm, ambient temperature.

Preparative HPLC, Method E

Gilson HPLC with Gilson UV-VIS-155 detector, 231 XL sampling injector.

The wavelength given is the substance-specific UV maximum.

A: water with 0.1% TFA
B: acetonitrile with 0.13% TFA

| time in min | % A | % B | flow rate in ml/min |
|---|---|---|---|
| 0.00 | 95 | 5 | 180 |
| 1.40 | 95 | 5 | 180 |
| 17.00 | 2 | 98 | 180 |
| 18.50 | 2 | 98 | 180 |
| 18.70 | 95 | 5 | 180 |
| 20.-50 | 95 | 5 | 180 |

The stationary phase used is a Microsorb RP 18 column, 100 A, 8 μm, 50×150 mm, ambient temperature.

Examples

The following Examples were prepared analogously to the synthesis methods described above (as indicated in the Table). These compounds are suitable as PDE4-inhibitors and have $IC_{50}$ values of less than or equal to 1 μmol. The inhibitions (in %) at 1 μM of the individual Example substances are included in the following Tables of Examples and were determined as follows:

The Scintilation Proximity (SPA) Assays (GE Healthcare, No. TRKQ7090) make use of the different affinities of cyclic 3"-5"-adenosine monophosphate (cAMP, low affinity) and linear 5'-adenosine monophosphate (AMP, high affinity) for yttrium silicate scintillator beads. The cAMP specific phosphodiesterase (PDE) PDE4B cleaves the 3'-phosphoester bond of the tritium-labelled [H3]-cAMP to form the [H3]-5'-AMP. Because of its higher affinity for the scintillator beads this [H3]-AMP accumulates on the beads and causes scintillation events (flashes of light) which are measured in a Wallac Microbeta Scintillation Counter.

The test starts with one hour's incubation of [H3]-cAMP with the PDE4B enzyme in assay buffer at 30° C., once with the Example substance that is to be tested (in a concentration of 1 μM) and once without the Example substance that is to be tested. After this incubation the reaction is stopped by the addition of the beads. The beads are given an opportunity to settle over the next 45 minutes, then they are measured in the Scintillation Counter. If the substance is capable of inhibiting the enzymatic activity of the PDE4B, less [H3]-AMP is formed during the incubation phase and fewer scintillation events can be measured. These results are expressed as a percentage inhibition at a concentration of the test substance of 1 μM.

The Examples relate to compounds of the following formula 1,

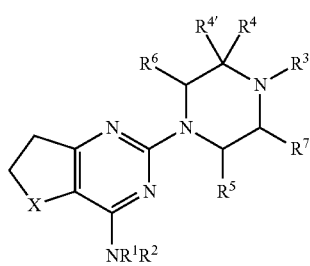

having the properties designated in Tables A and B that follow:

TABLE A

Chemical structures of Example substances 1-29

| # | Structure | $R^1$ | $R^2$ | $R^3$ | $R^4$ | $R^{4'}$ | $R^5$ | $R^6$ | $R^7$ | % Inhibition PDE4B @ 1 μM |
|---|---|---|---|---|---|---|---|---|---|---|
| 1 | | Cl | H | *⟨⟩OH | Cl | H | H | $CH_3$ | H | H | 84 |

TABLE A-continued

Chemical structures of Example substances 1-29

| # | Structure | R¹ | R² | R³ | R⁴ | R⁴' | R⁵ | R⁶ | R⁷ | % Inhibition PDE4B @ 1 μM |
|---|---|---|---|---|---|---|---|---|---|---|
| 2 | | 4-Cl-C₆H₄ | H | *CH(iPr)CH₂OH | 4-Cl-C₆H₄ | H | H | CH₃ | H | H | 94 |
| 3 | | 4-Cl-C₆H₄ | H | *(5)-1-methyl-2-oxopiperidin-5-yl | 4-Cl-C₆H₄ | H | H | CH₃ | H | H | 96 |
| 4 | | 4-Cl-C₆H₄ | H | *tetrahydropyran-4-yl | 4-Cl-C₆H₄ | H | H | CH₃ | H | H | 95 |
| 5 | | 4-Cl-C₆H₄ | H | *1-(hydroxymethyl)cyclopropyl | 4-Cl-C₆H₄ | H | H | CH₃ | H | H | 95 |

TABLE A-continued

Chemical structures of Example substances 1-29

| # | Structure | R¹ | R² | R³ | R⁴ | R⁴' | R⁵ | R⁶ | R⁷ | % Inhibition PDE4B @ 1 μM |
|---|---|---|---|---|---|---|---|---|---|---|
| 6 | 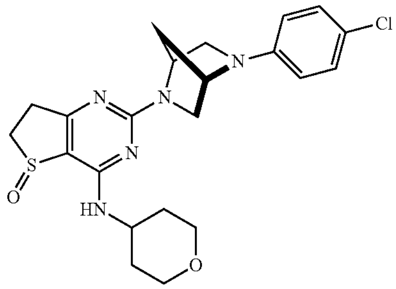 | H | *-tetrahydropyran-4-yl | 4-Cl-phenyl | H | H | H | together form —CH₂— | | 95 |
| 7 | 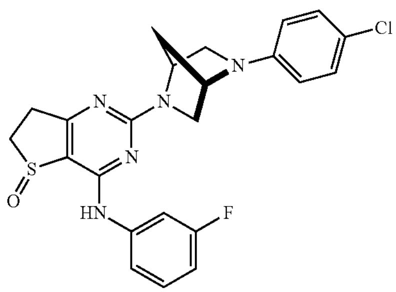 | H | *-(3-fluorophenyl) | 4-Cl-phenyl | H | H | H | together form —CH₂— | | 95 |
| 8 | 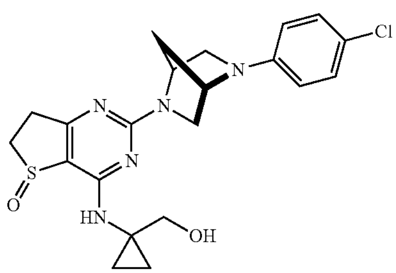 | H | *-(1-hydroxymethyl-cyclopropyl) | 4-Cl-phenyl | H | H | H | together form —CH₂— | | 95 |
| 9 | 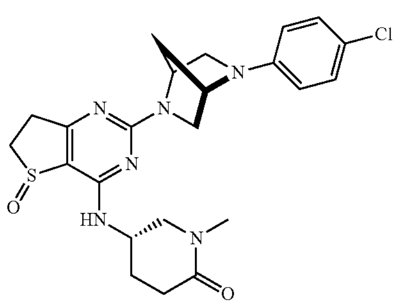 | H | *-(1-methyl-2-oxo-piperidin-5-yl) | 4-Cl-phenyl | H | H | H | together form —CH₂— | | 96 |

TABLE A-continued

Chemical structures of Example substances 1-29

| # | Structure | R¹ | R² | R³ | R⁴ | R⁴' | R⁵ | R⁶ | R⁷ | % Inhibition PDE4B @ 1 μM |
|---|---|---|---|---|---|---|---|---|---|---|
| 10 | 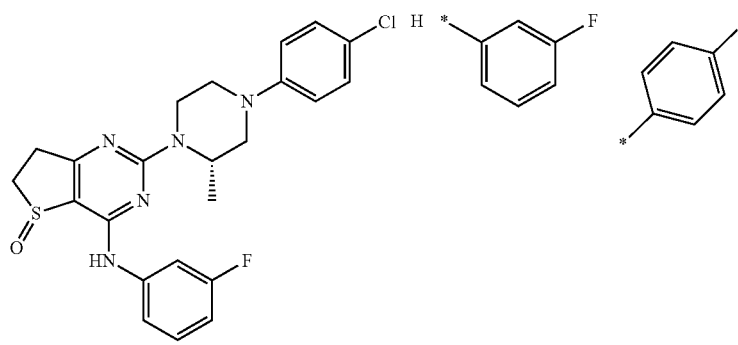 | 4-Cl-phenyl | H | 3-F-phenyl | 4-Cl-phenyl | H | H | CH₃ | H | H | 94 |
| 11 | 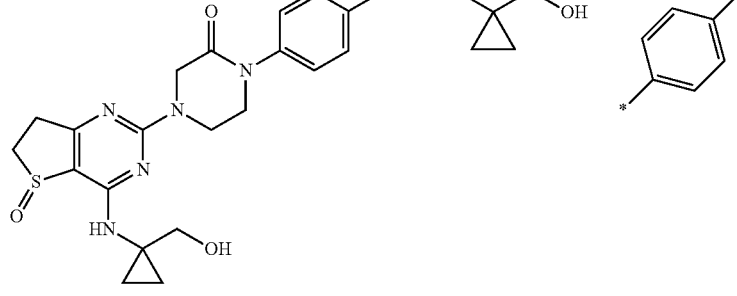 | 4-Br-phenyl | H | 1-(hydroxymethyl)cyclopropyl | 4-Br-phenyl | together form an oxo group | | H | H | H | 90 |
| 12 | 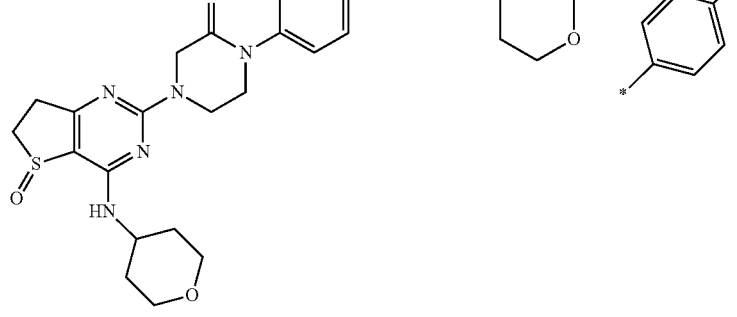 | 4-Br-phenyl | H | tetrahydropyran-4-yl | 4-Br-phenyl | together form an oxo group | | H | H | H | 93 |
| 13 | 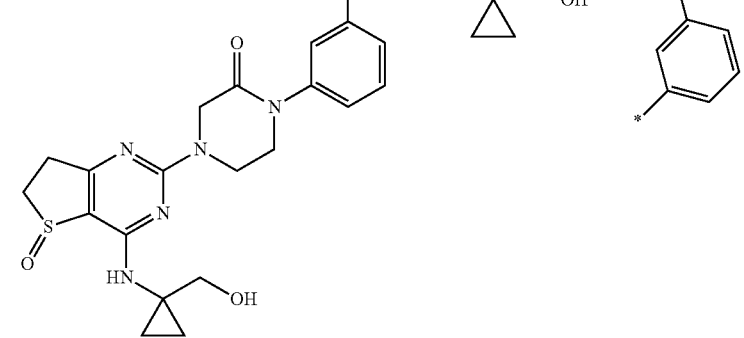 | 3-Br-phenyl | H | 1-(hydroxymethyl)cyclopropyl | 3-Br-phenyl | together form an oxo group | | H | H | H | 19 |

TABLE A-continued

Chemical structures of Example substances 1-29

| # | Structure | R¹ | R² | R³ | R⁴ R⁴' | R⁵ | R⁶ | R⁷ | % Inhibition PDE4B @ 1 μM |
|---|---|---|---|---|---|---|---|---|---|
| 14 | 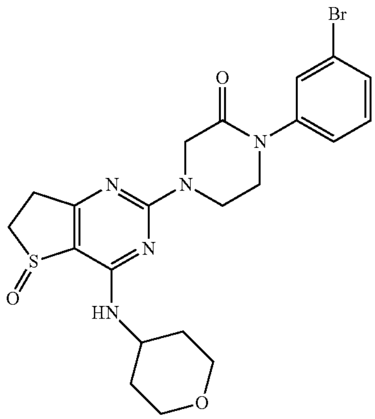 | H | *tetrahydropyran-4-yl | 3-bromophenyl | together form an oxo group | H | H | H | 92 |
| 15 | 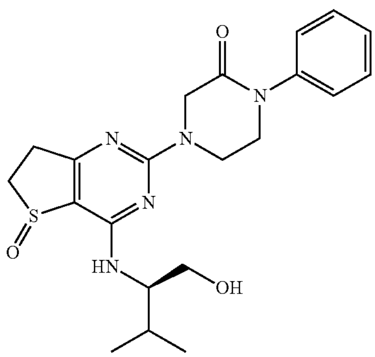 | H | *CH(iPr)CH₂OH | phenyl | together form an oxo group | H | H | H | 77 |
| 16 | 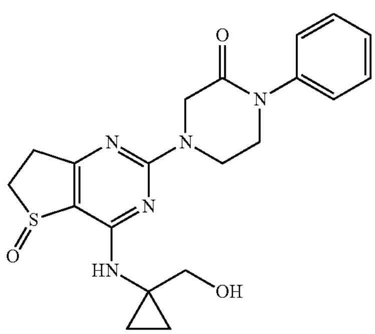 | H | *C(cyclopropyl)CH₂OH | phenyl | together form an oxo group | H | H | H | 86 |
| 17 | 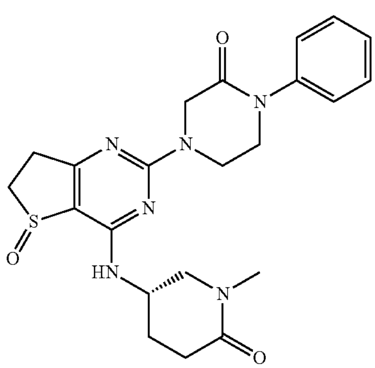 | H | *N-methyl-piperidin-2-one-5-yl | phenyl | together form an oxo group | H | H | H | 96 |

TABLE A-continued

Chemical structures of Example substances 1-29

| # | Structure | R¹ | R² | R³ | R⁴ R⁴' | R⁵ | R⁶ | R⁷ | % Inhibition PDE4B @ 1 μM |
|---|---|---|---|---|---|---|---|---|---|
| 18 | 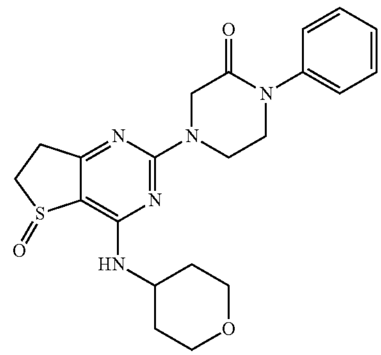 | H | *-tetrahydropyran-4-yl | *-phenyl | together form an oxo group | H | H | H | 93 |
| 19 | 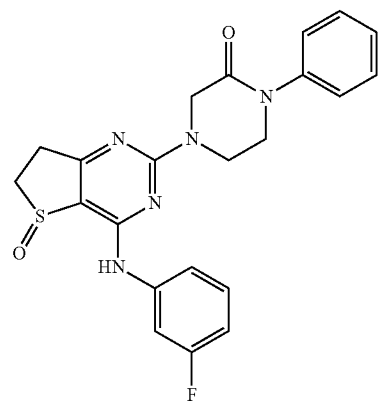 | H | *-(3-fluorophenyl) | *-phenyl | together form an oxo group | H | H | H | 95 |
| 20 | 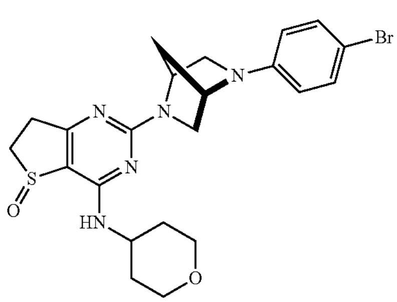 | H | *-tetrahydropyran-4-yl | *-(4-bromophenyl) | H H | H | H | together form —CH₂— | 95 |
| 21 | 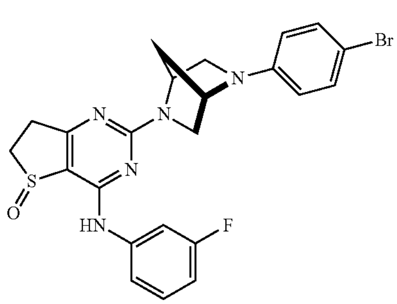 | H | *-(3-fluorophenyl) | *-(4-bromophenyl) | H H | H | H | together form —CH₂— | 95 |

TABLE A-continued

Chemical structures of Example substances 1-29

| # | Structure | R¹ | R² | R³ | R⁴ | R⁴' | R⁵ | R⁶ | R⁷ | % Inhibition PDE4B @ 1 μM |
|---|---|---|---|---|---|---|---|---|---|---|
| 22 | 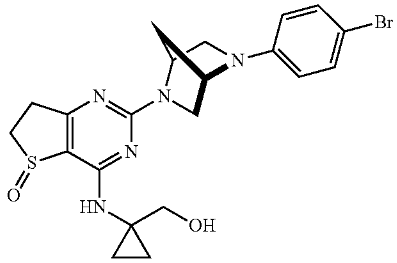 | H | *―C(cyclopropyl)―CH₂OH | 4-Br-C₆H₄― | H | H | H | together form ―CH₂― | | 95 |
| 23 | 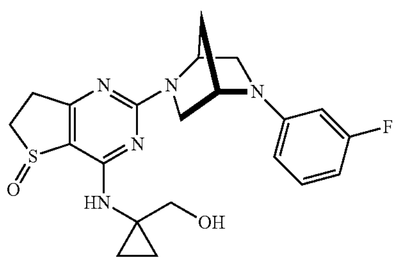 | H | *―C(cyclopropyl)―CH₂OH | 3-F-C₆H₄― | H | H | H | together form ―CH₂― | | 93 |
| 24 | 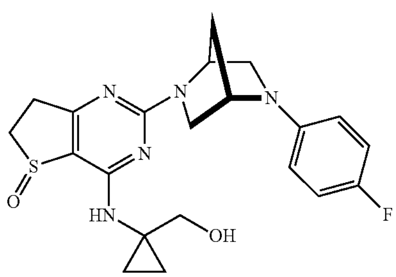 | H | *―C(cyclopropyl)―CH₂OH | 4-F-C₆H₄― | H | H | H | together form ―CH₂― | | 93 |
| 25 | 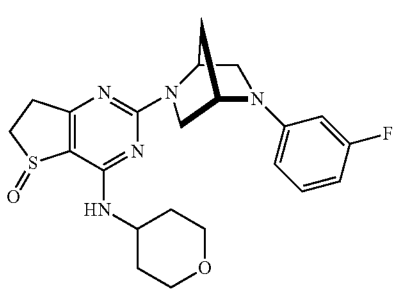 | H | *―(tetrahydropyran-4-yl) | 3-F-C₆H₄― | H | H | H | together form ―CH₂― | | 94 |

TABLE A-continued

Chemical structures of Example substances 1-29

| # | Structure | R¹ | R² | R³ | R⁴ | R⁴' | R⁵ | R⁶ | R⁷ | % Inhibition PDE4B @ 1 μM |
|---|---|---|---|---|---|---|---|---|---|---|
| 26 | 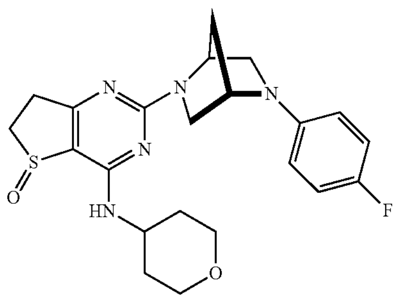 | H | *-tetrahydropyran-4-yl | *-(4-fluorophenyl) | H | H | H | together form —CH₂— | | 94 |
| 27 | 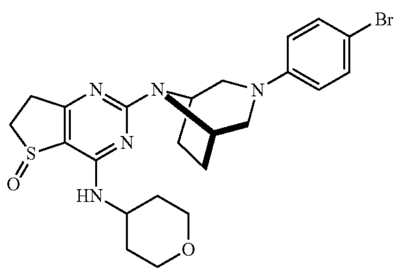 | 4-Br-phenyl | H | *-tetrahydropyran-4-yl | 4-Br-phenyl | H | H | together form —CH₂—CH₂— | H | 97 |
| 28 | 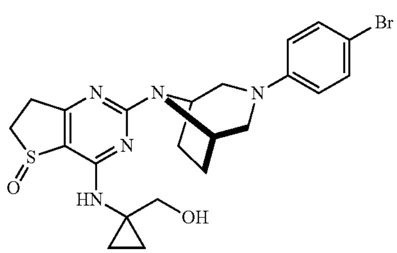 | 4-Br-phenyl | H | *-C(cyclopropyl)(CH₂OH) | 4-Br-phenyl | H | H | together form —CH₂—CH₂— | H | 97 |
| 29 | 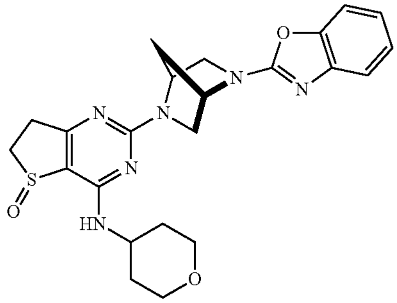 | benzoxazol-2-yl | H | *-tetrahydropyran-4-yl | benzoxazol-2-yl | H | H | together form —CH₂—CH₂— | | 97 |

The following Table B gives detailed information on the chemical syntheses and analysis of the individual Example substances 1-29.

TABLE B

Detailed information on the preparation of the individual Example substances 1-29

| # | structure | prepared analogously to #* | non-commercial arylpiperazine component (V) | literature on preparing the non-commercial arylpiperazine component (V) | analytical HPLC-MS, RT [min], method |
|---|---|---|---|---|---|
| 1 | 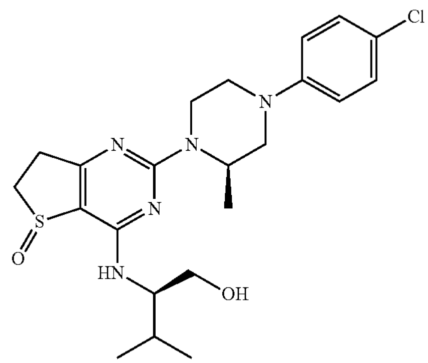 [SMILES: CC(C)[C@H](CO)Nc1nc(N2CCN(c3ccc(Cl)cc3)C[C@H]2C)nc2c1S(=O)CC2] | see experim. section | | | 1.26 method A |
| 2 | 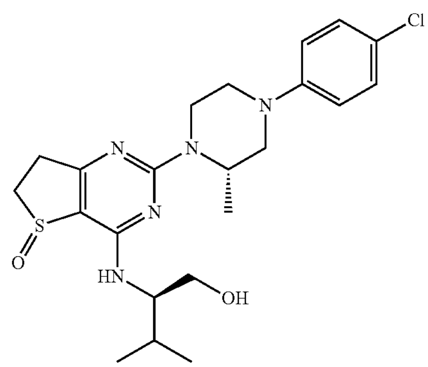 [SMILES: CC(C)[C@H](CO)Nc1nc(N2CCN(c3ccc(Cl)cc3)C[C@@H]2C)nc2c1S(=O)CC2] | 1 | | Tet. Asymm. 2002, 2303 | 1.20 method A |
| 3 | 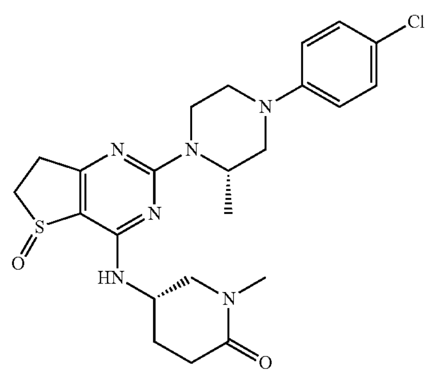 [SMILES: C[C@H]1CN(c2ccc(Cl)cc2)CCN1c1nc2c(c(N[C@H]3CCC(=O)N(C)C3)n1)S(=O)CC2] | 9 | | Tet. Asymm. 2002, 2303 | 1.21 method A |
| 4 | 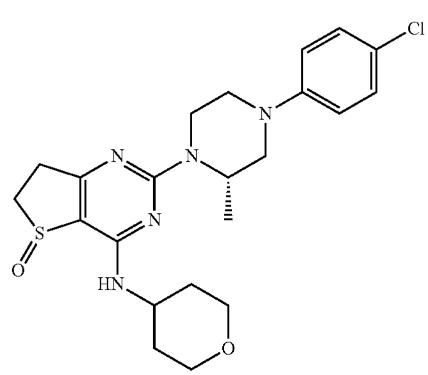 [SMILES: C[C@H]1CN(c2ccc(Cl)cc2)CCN1c1nc2c(c(NC3CCOCC3)n1)S(=O)CC2] | 29 | | Tet. Asymm. 2002, 2304 | 1.27 method A |

TABLE B-continued

Detailed information on the preparation of the individual Example substances 1-29

| # | structure | prepared analogously to #* | non-commercial arylpiperazine component (V) | literature on preparing the non-commercial arylpiperazine component (V) | analytical HPLC-MS, RT [min], method |
|---|---|---|---|---|---|
| 5 | 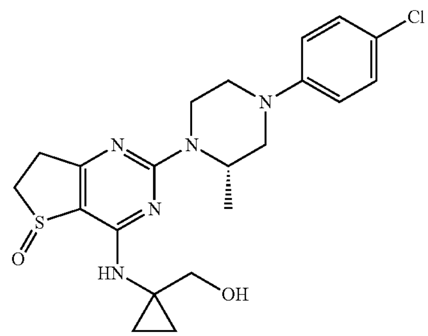 [SMILES: C[C@H]1CN(c2ccc(Cl)cc2)CCN1c1nc2c(c(NC3(CO)CC3)n1)S(=O)CC2] | 24 | | Tet. Asymm. 2002, 2305 | 1.24 method A |
| 6 | 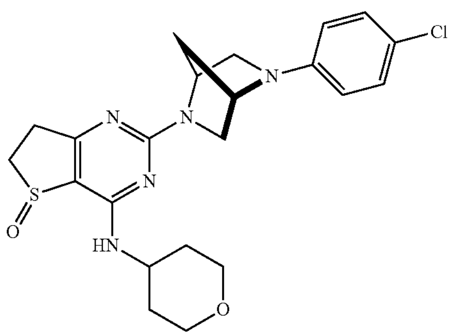 | 29 | | | 1.16 method A |
| 7 | 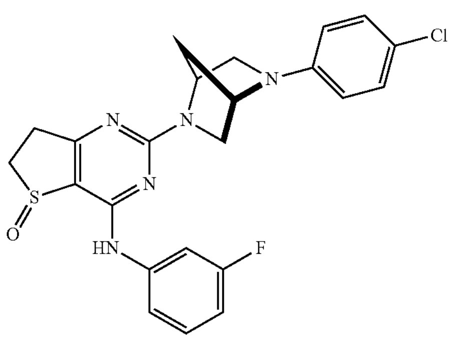 | 21 | | | 1.32 method A |
| 8 | 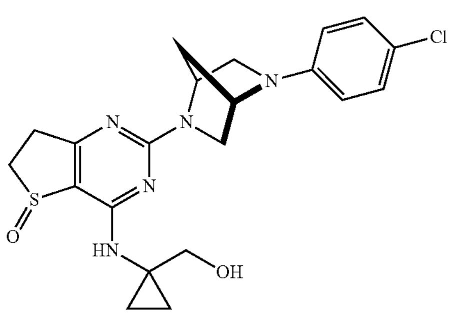 | 24 | | | 1.10 method A |

TABLE B-continued
Detailed information on the preparation of the individual Example substances 1-29
| # | structure | prepared analogously to #* | non-commercial arylpiperazine component (V) | literature on preparing the non-commercial arylpiperazine component (V) | analytical HPLC-MS, RT [min], method |
|---|---|---|---|---|---|
| 9 | 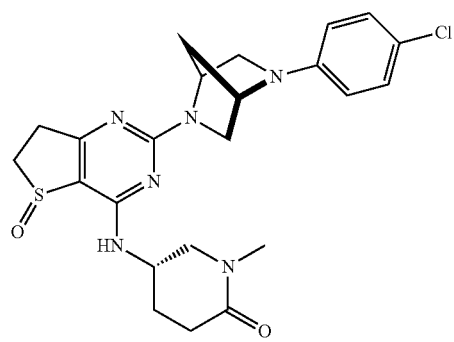 | see experim. section | | | 1.13 method A |
| 10 | 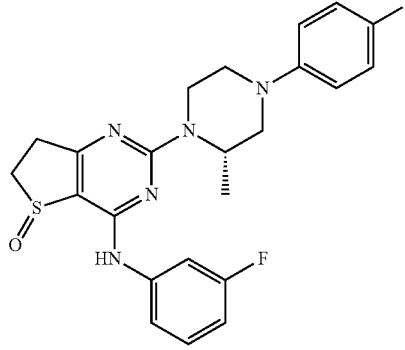 | 21 | 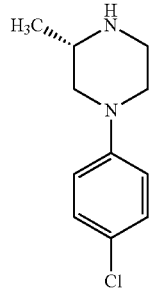 | Tet. Asymm. 2002, 2305 | 1.47 method A |
| 11 | 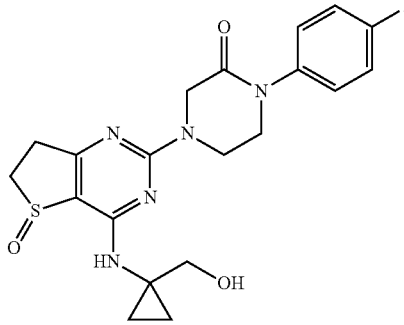 | 24 | | | 1.00 method D |
| 12 | 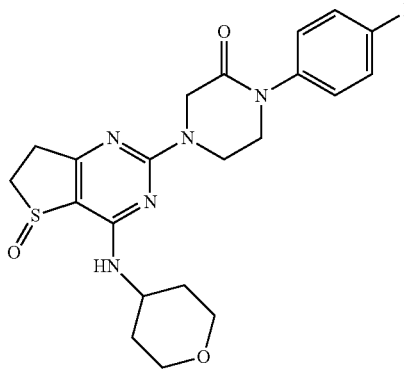 | 29 | | | 1.04 method D |

TABLE B-continued

Detailed information on the preparation of the individual Example substances 1-29

| # | structure | prepared analogously to #* | non-commercial arylpiperazine component (V) | literature on preparing the non-commercial arylpiperazine component (V) | analytical HPLC-MS, RT [min], method |
|---|---|---|---|---|---|
| 13 | 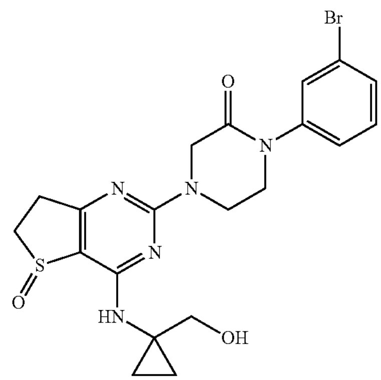 [SMILES: O=C1CN(c2nc3c(c(NC4(CO)CC4)n2)S(=O)CC3)CCN1c1cccc(Br)c1] | 24 | | | 1.00 method D |
| 14 | 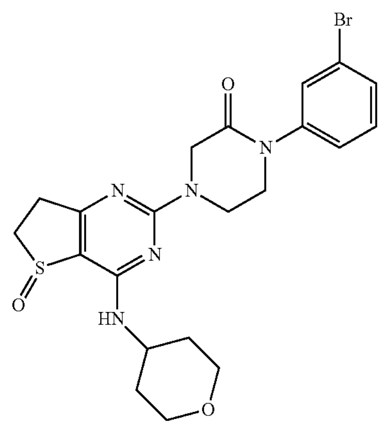 [SMILES: O=C1CN(c2nc3c(c(NC4CCOCC4)n2)S(=O)CC3)CCN1c1cccc(Br)c1] | 29 | | | 1.04 method D |
| 15 | 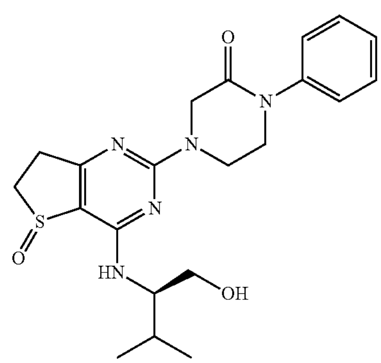 [SMILES: CC(C)[C@H](CO)Nc1nc(N2CCN(c3ccccc3)C(=O)C2)nc2c1S(=O)CC2] | 1 | | | 1.61 method C |
| 16 | 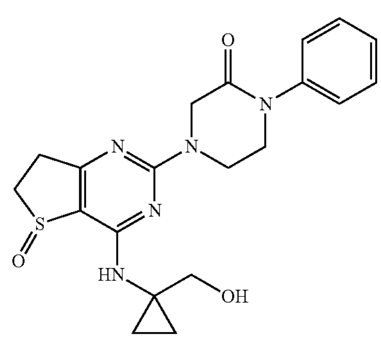 [SMILES: O=C1CN(c2nc3c(c(NC4(CO)CC4)n2)S(=O)CC3)CCN1c1ccccc1] | 24 | | | 1.61 method C |

TABLE B-continued

Detailed information on the preparation of the individual Example substances 1-29

| # | structure | prepared analogously to #* | non-commercial arylpiperazine component (V) | literature on preparing the non-commercial arylpiperazine component (V) | analytical HPLC-MS, RT [min], method |
|---|---|---|---|---|---|
| 17 | 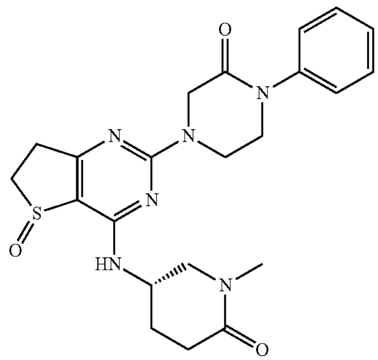 [SMILES: CN1C[C@@H](Nc2nc(N3CCN(c4ccccc4)C(=O)C3)nc3c2S(=O)CC3)CCC1=O] | 9 | | | 1.61 method C |
| 18 | 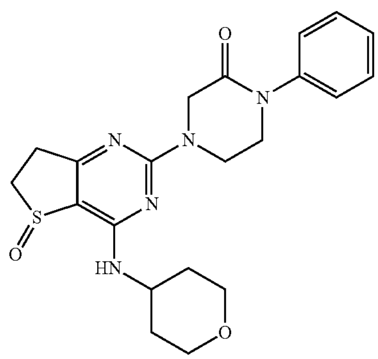 [SMILES: O=C1CN(c2nc3c(c(NC4CCOCC4)n2)S(=O)CC3)CCN1c1ccccc1] | 29 | | | 1.61 method C |
| 19 | 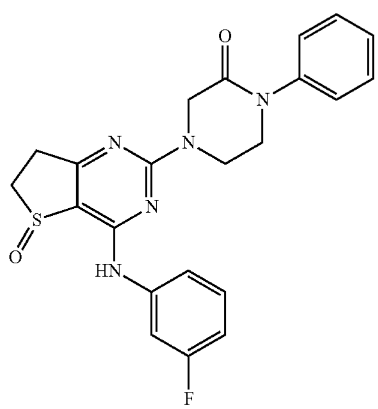 [SMILES: O=C1CN(c2nc3c(c(Nc4cccc(F)c4)n2)S(=O)CC3)CCN1c1ccccc1] | 21 | | | 1.61 method C |
| 20 | 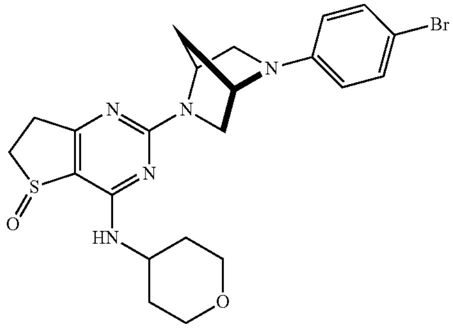 | 29 | | see experim. section § 3.3, component (V-2) | 1.19 method A |

TABLE B-continued

Detailed information on the preparation of the individual Example substances 1-29

| # | structure | prepared analogously to #* | non-commercial arylpiperazine component (V) | literature on preparing the non-commercial arylpiperazine component (V) | analytical HPLC-MS, RT [min], method |
|---|---|---|---|---|---|
| 21 | 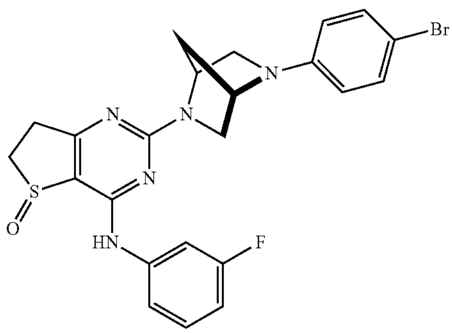 | | see experim. section | | 1.19 method A |
| 22 | 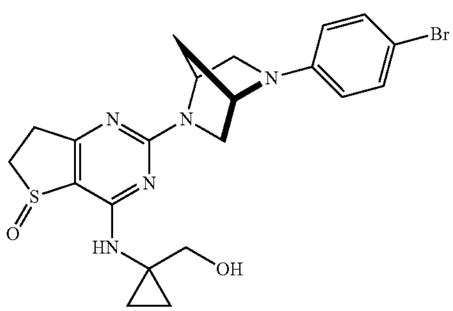 | 24 | | see experim. section § 3.3, component (V-2) | 1.16 method A |
| 23 | 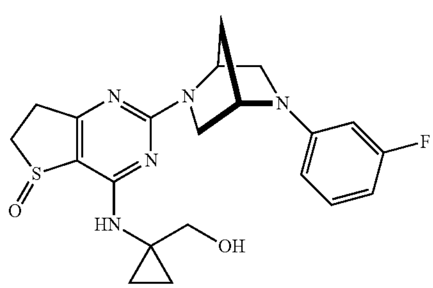 | 24 | | | 1.10 method A |
| 24 | 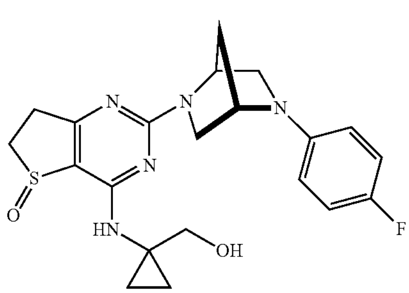 | | see experim. section | | 1.08 method A |

TABLE B-continued

Detailed information on the preparation of the individual Example substances 1-29

| # | structure | prepared analogously to #* | non-commercial arylpiperazine component (V) | literature on preparing the non-commercial arylpiperazine component (V) | analytical HPLC-MS, RT [min], method |
|---|---|---|---|---|---|
| 25 | 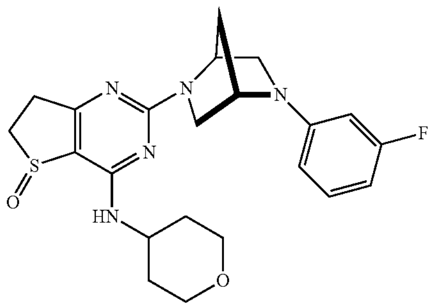 | 29 | | | 1.16 method A |
| 26 | 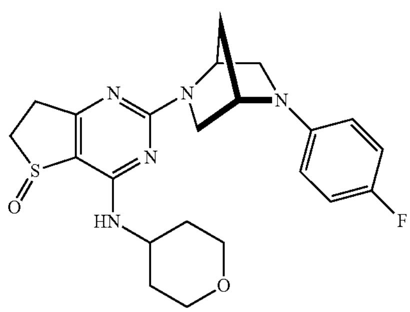 | 29 | | | 1.14 method A |
| 27 | 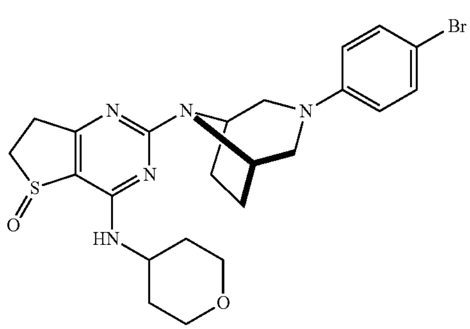 | 29 | | see experim. section § 5.1, component (V-3) | 1.40 method B |
| 28 | 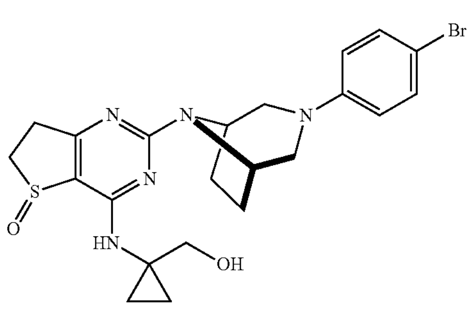 | see experim. section | | | 1.37 method B |

TABLE B-continued

Detailed information on the preparation of the individual Example substances 1-29

| # | structure | prepared analogously to #* | non-commercial arylpiperazine component (V) | literature on preparing the non-commercial arylpiperazine component (V) | analytical HPLC-MS, RT [min], method |
|---|---|---|---|---|---|
| 29 | 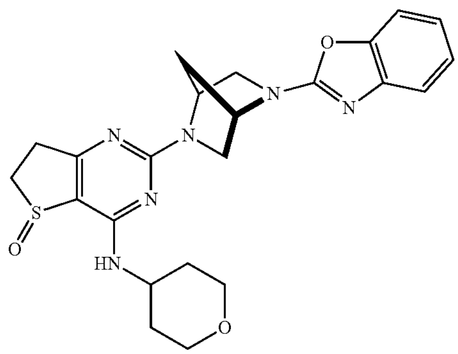 | | | see experim. section | 1.05 method A |

*the Example may be prepared and purified analogously.

The Examples also relate to the following compounds 30-45 of general formula 1, which are listed in Table C:

TABLE C

Chemical structures and details for preparing Example substances 30-45

| # | structure | prepared analogously to #* | non-commercial arylpiperazine component (V) | literature on preparing the non-commercial arylpiperazine component (V) | analytical HPLC-MS, RT [min], method | % inhibition PDE4B @ 1 μM |
|---|---|---|---|---|---|---|
| 30 | 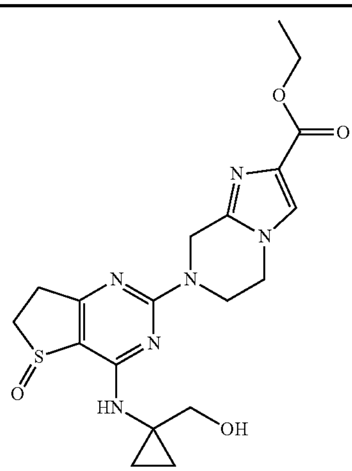 | 33 | | | 1.48 method C | 95 |
| 31 | 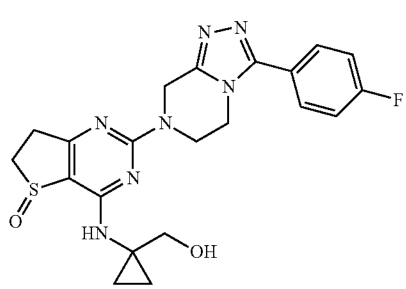 [SMILES: O=S1CCc2nc(N3CCn4c(nnc4-c4ccc(F)cc4)C3)nc(NC3(CO)CC3)c21] | 33 | | see experim. section § 9.1, component (V-5) | 1.61 method C | 93 |

TABLE C-continued

Chemical structures and details for preparing Example substances 30-45

| # | structure | prepared analogously to #* | non-commercial arylpiperazine component (V) | literature on preparing the non-commercial arylpiperazine component (V) | analytical HPLC-MS, RT [min], method | % inhibition PDE4B @ 1 μM |
|---|---|---|---|---|---|---|
| 32 | 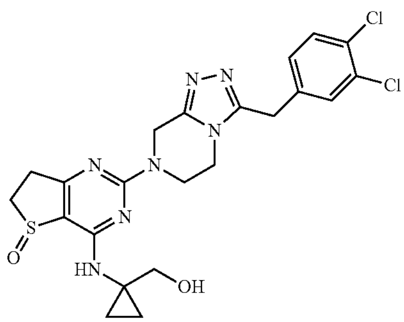 [SMILES: O=S1CCc2nc(N3CCn4c(Cc5ccc(Cl)c(Cl)c5)nnc4C3)nc(NC3(CO)CC3)c21] | 33 | | see experim. section § 10.1, component (V-6) | 1.76 method C | 91 |
| 33 | 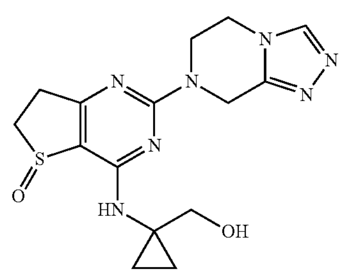 [SMILES: O=S1CCc2nc(N3CCn4cnnc4C3)nc(NC3(CO)CC3)c21] | see experim. section | | | 1.62 method C | 75 |
| 34 | 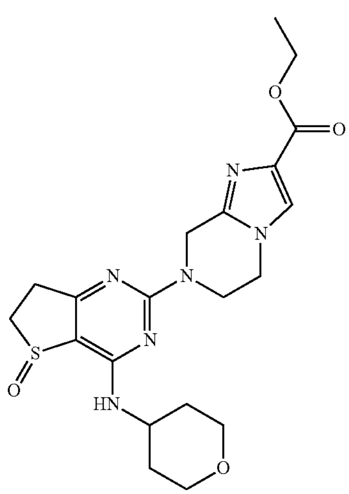 [SMILES: CCOC(=O)c1cn2c(n1)CN(c1nc3c(c(NC4CCOCC4)n1)S(=O)CC3)CC2] | 37 | | | 1.51 method C | 95 |
| 35 | 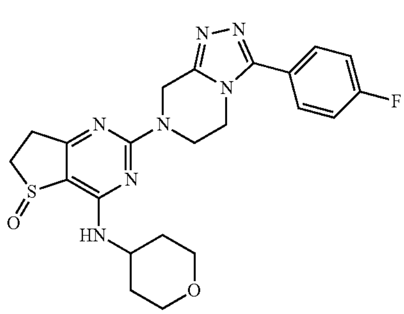 [SMILES: O=S1CCc2nc(N3CCn4c(nnc4-c4ccc(F)cc4)C3)nc(NC3CCOCC3)c21] | 37 | | see experim. section § 9.1, component (V-5) | 1.65 method C | 94 |

TABLE C-continued

Chemical structures and details for preparing Example substances 30-45

| # | structure | prepared analogously to #* | non-commercial arylpiperazine component (V) | literature on preparing the non-commercial arylpiperazine component (V) | analytical HPLC-MS, RT [min], method | % inhibition PDE4B @ 1 μM |
|---|---|---|---|---|---|---|
| 36 | 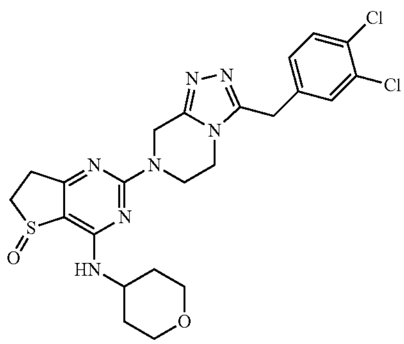 [SMILES: O=S1CCc2nc(N3CCn4c(Cc5ccc(Cl)c(Cl)c5)nnc4C3)nc(NC3CCOCC3)c21] | 37 | | see experim. section § 10.1, component (V-6) | 1.79 method C | 93 |
| 37 | 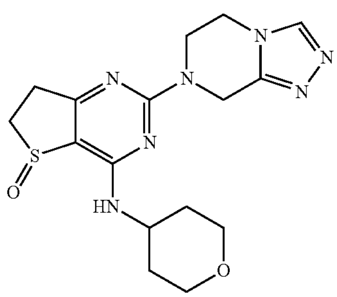 [SMILES: O=S1CCc2nc(N3CCn4cnnc4C3)nc(NC3CCOCC3)c21] | | see experim. section | | 1.35 method C | 87 |
| 38 | 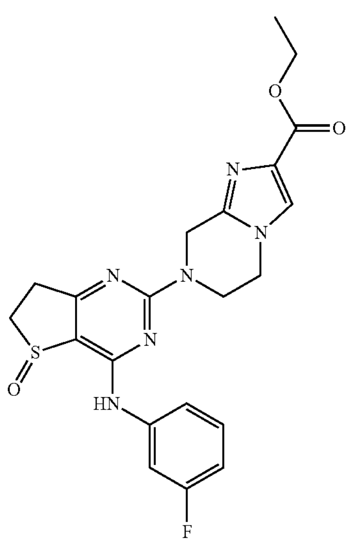 [SMILES: CCOC(=O)c1cn2c(n1)CN(c1nc3c(c(Nc4cccc(F)c4)n1)S(=O)CC3)CC2] | 39 | | | 1.74 method C | 95 |

TABLE C-continued

Chemical structures and details for preparing Example substances 30-45

| # | structure | prepared analogously to #* | non-commercial arylpiperazine component (V) | literature on preparing the non-commercial arylpiperazine component (V) | analytical HPLC-MS, RT [min], method | % inhibition PDE4B @ 1 µM |
|---|---|---|---|---|---|---|
| 39 | 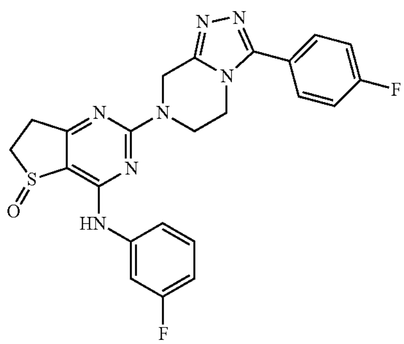 [SMILES: O=S1CCc2nc(N3CCn4c(nnc4-c4ccc(F)cc4)C3)nc(Nc3cccc(F)c3)c21] | see experim. section | | | 1.89 method C | 95 |
| 40 | 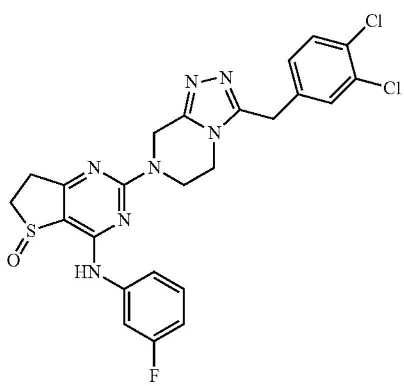 [SMILES: O=S1CCc2nc(N3CCn4c(Cc5ccc(Cl)c(Cl)c5)nnc4C3)nc(Nc3cccc(F)c3)c21] | see experim. section | | | 2.02 method C | 94 |
| 41 | 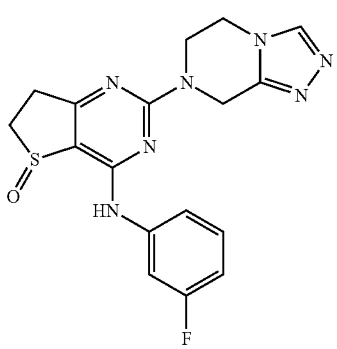 [SMILES: O=S1CCc2nc(N3CCn4cnnc4C3)nc(Nc3cccc(F)c3)c21] | see experim. section | | | 1.6 method C | 90 |
| 42 | 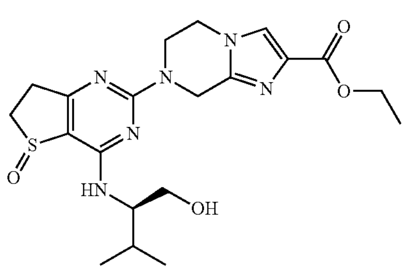 [SMILES: CCOC(=O)c1cn2c(n1)CN(c1nc3c(c(N[C@@H](CO)C(C)C)n1)S(=O)CC3)CC2] | 45 | | | 1.53 method C | 94 |

TABLE C-continued

Chemical structures and details for preparing Example substances 30-45

| # | structure | prepared analogously to #* | non-commercial arylpiperazine component (V) | literature on preparing the non-commercial arylpiperazine component (V) | analytical HPLC-MS, RT [min], method | % inhibition PDE4B @ 1 µM |
|---|---|---|---|---|---|---|
| 43 | 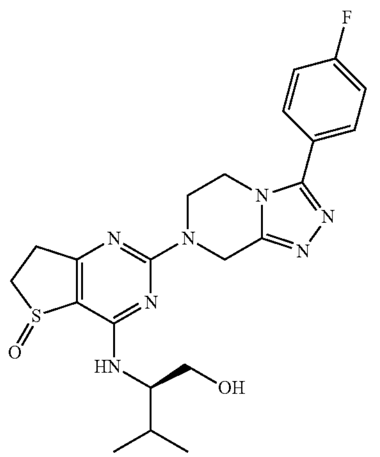 [SMILES: CC(C)[C@H](CO)Nc1nc(N2CCn3c(nnc3-c3ccc(F)cc3)C2)nc2c1S(=O)CC2] | 45 | | see experim. section § 9.1, component (V-5) | 1.64 method C | 88 |
| 44 | 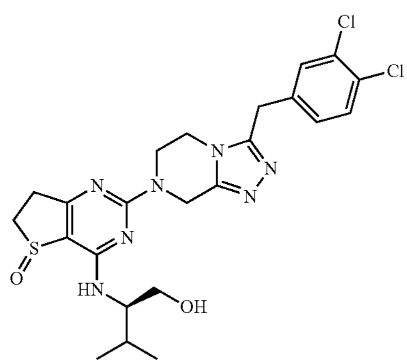 [SMILES: CC(C)[C@H](CO)Nc1nc(N2CCn3c(Cc4ccc(Cl)c(Cl)c4)nnc3C2)nc2c1S(=O)CC2] | 45 | | see experim. section § 10.1, component (V-6) | 1.79 method C | 78 |
| 45 | 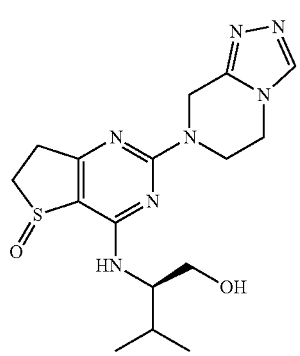 [SMILES: CC(C)[C@H](CO)Nc1nc(N2CCn3cnnc3C2)nc2c1S(=O)CC2] | | | see experim. section | 1.35 method C | 55 |

*the Example may be prepared and purified analogously.

The Examples also relate to the following compounds 46-57 of general formula 1, which are listed in Table D:

TABLE D
Chemical structures and details for preparing Example substances 46-57
| # | structure | prepared analogously to #* | non-commercial arylpiperidine component (V) | literature on preparing component (V) | analytical HPLC-MS, RT [min], method | % inhibition PDE4B @ 1 μM |
|---|---|---|---|---|---|---|
| 46 | 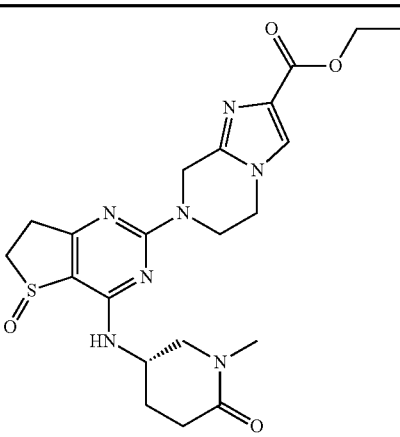 | 9 | | | 1.05 method B | 97 |
| 47 | 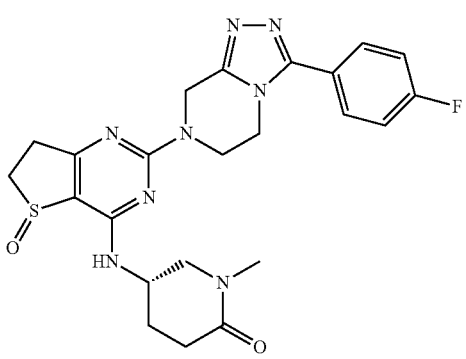 [SMILES: CN1C[C@@H](Nc2nc(N3CCn4c(nnc4-c4ccc(F)cc4)C3)nc3c2S(=O)CC3)CCC1=O] | 9 | 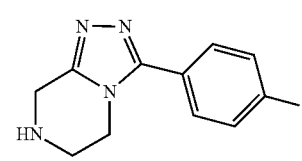 | see experim. section § 9.1, component (V-5) | 1.12 method B | 96 |
| 48 | 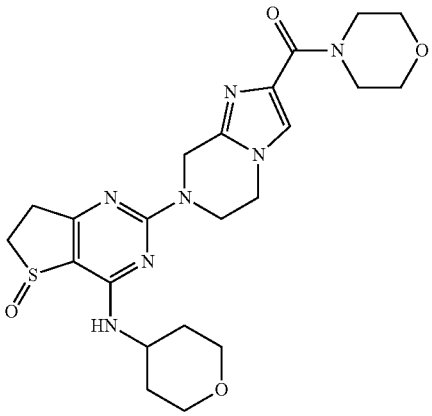 [SMILES: O=C(c1cn2c(n1)CN(c1nc3c(c(NC4CCOCC4)n1)S(=O)CC3)CC2)N1CCOCC1] | see experim. section | | | 0.79 method D | 93 |

TABLE D-continued

Chemical structures and details for preparing Example substances 46-57

| # | structure | prepared analogously to #* | non-commercial arylpiperidine component (V) | literature on preparing component (V) | analytical HPLC-MS, RT [min], method | % inhibition PDE4B @ 1 μM |
|---|---|---|---|---|---|---|
| 49 | 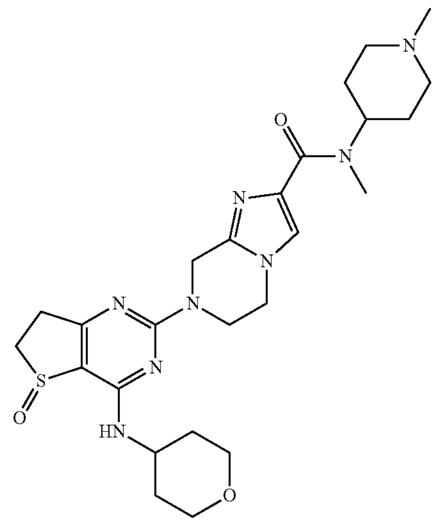 [SMILES: CN1CCC(N(C)C(=O)c2cn3c(n2)CN(c2nc4c(c(NC5CCOCC5)n2)S(=O)CC4)CC3)CC1] | 48 | | | 0.81 method D | 93 |
| 50 | 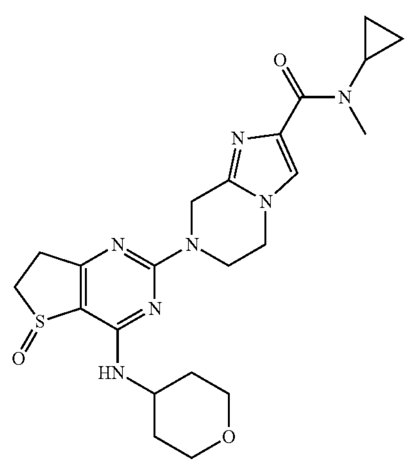 [SMILES: CN(C(=O)c1cn2c(n1)CN(c1nc3c(c(NC4CCOCC4)n1)S(=O)CC3)CC2)C1CC1] | 48 | | | 0.83 method D | 93 |
| 51 | 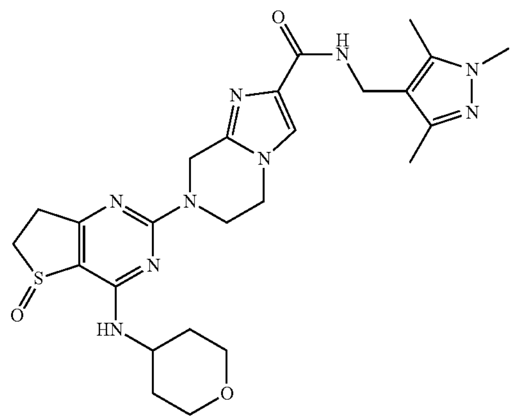 [SMILES: Cc1nn(C)c(C)c1CNC(=O)c1cn2c(n1)CN(c1nc3c(c(NC4CCOCC4)n1)S(=O)CC3)CC2] | 48 | | | 0.84 method D | 94 |

TABLE D-continued

Chemical structures and details for preparing Example substances 46-57

| # | structure | prepared analogously to #* | non-commercial arylpiperidine component (V) | literature on preparing component (V) | analytical HPLC-MS, RT [min], method | % inhibition PDE4B @ 1 μM |
|---|---|---|---|---|---|---|
| 52 | 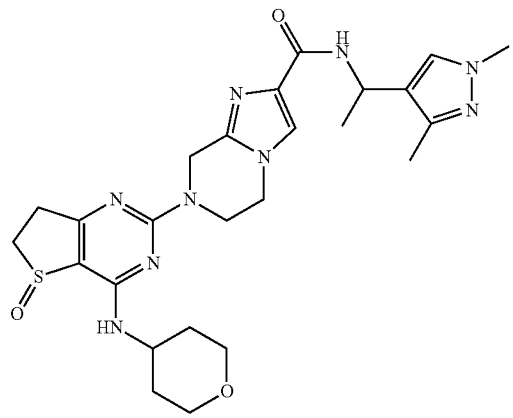 [SMILES: Cc1nn(C)cc1C(C)NC(=O)c1cn2c(n1)CN(c1nc3c(c(NC4CCOCC4)n1)S(=O)CC3)CC2] | 48 | | | 1.09 method B | 93 |
| 53 | 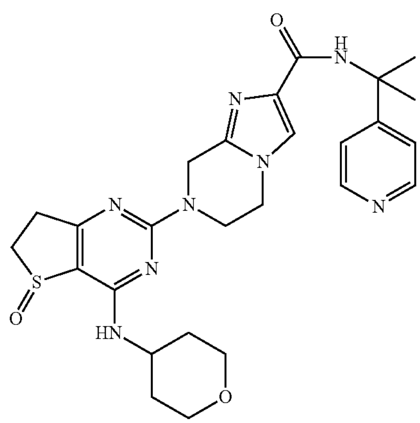 [SMILES: CC(C)(NC(=O)c1cn2c(n1)CN(c1nc3c(c(NC4CCOCC4)n1)S(=O)CC3)CC2)c1ccncc1] | 48 | | | 1.06 method B | 94 |
| 54 | 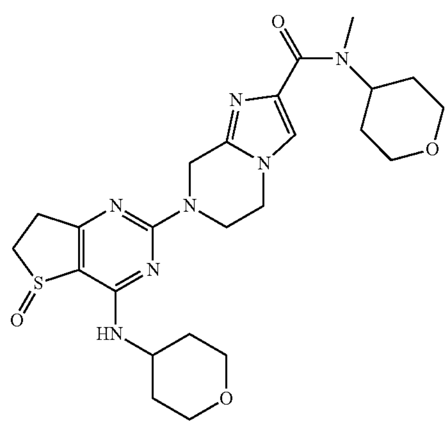 [SMILES: CN(C(=O)c1cn2c(n1)CN(c1nc3c(c(NC4CCOCC4)n1)S(=O)CC3)CC2)C1CCOCC1] | 48 | | | 1.07 method B | 94 |

TABLE D-continued
Chemical structures and details for preparing Example substances 46-57
| # | structure | prepared analogously to #* | non-commercial arylpiperidine component (V) | literature on preparing component (V) | analytical HPLC-MS, RT [min], method | % inhibition PDE4B @ 1 µM |
|---|---|---|---|---|---|---|
| 55 | 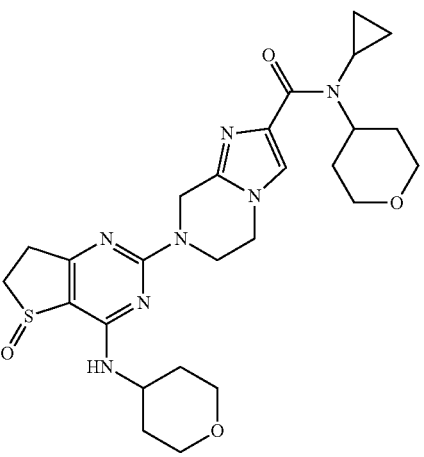 [SMILES: O=C(c1cn2c(n1)CN(c1nc3c(c(NC4CCOCC4)n1)S(=O)CC3)CC2)N(C1CCOCC1)C1CC1] | 48 | | | 1.11 method B | 93 |
| 56 | 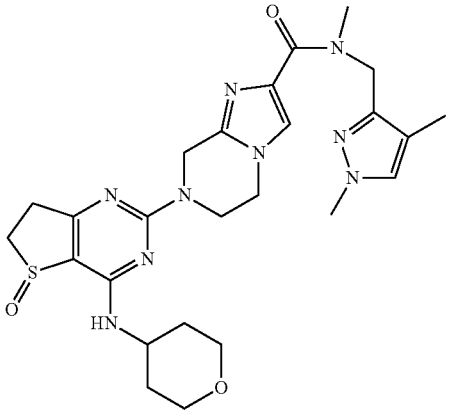 [SMILES: Cc1cn(C)nc1CN(C)C(=O)c1cn2c(n1)CN(c1nc3c(c(NC4CCOCC4)n1)S(=O)CC3)CC2] | 48 | | | 1.07 method B | 94 |
| 57 | 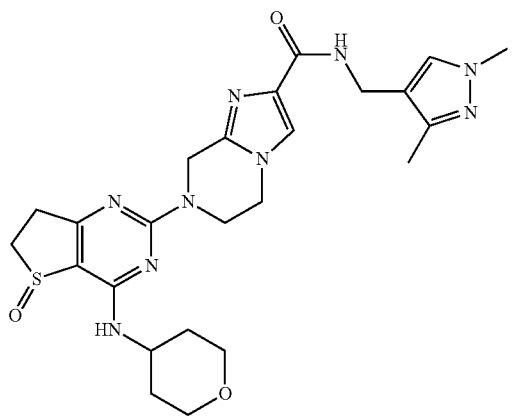 [SMILES: Cc1nn(C)cc1CNC(=O)c1cn2c(n1)CN(c1nc3c(c(NC4CCOCC4)n1)S(=O)CC3)CC2] | 48 | | | 1.05 method B | 94 |
*the Example may be prepared and purified analogously.

Indications

As has been found, the compounds of formula 1 are characterised by their wide range of applications in the therapeutic field. Particular mention should be made of those applications for which the compounds according to the invention of formula 1 are preferably suited on account of their pharmaceutical efficacy as PDE4 inhibitors. Examples include respiratory or gastrointestinal diseases or complaints, inflammatory diseases of the joints, skin or eyes, cancers, and also diseases of the peripheral or central nervous system.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Also deserving special mention is the treatment of inflammatory diseases of the gastrointestinal tract. Examples include acute or chronic inflammatory changes in gall bladder inflammation, Crohn's disease, ulcerative colitis, inflammatory pseudopolyps, juvenile polyps, colitis cystica profunda, pneumatosis cystoides intestinales, diseases of the bile duct and gall bladder, e.g. gallstones and conglomerates, for the treatment of inflammatory diseases of the joints such as rheumatoid arthritis or inflammatory diseases of the skin and eyes.

Preferential mention should also be made of the treatment of cancers. Examples include all forms of acute and chronic leukaemias such as acute lymphatic and acute myeloid leukaemia, chronic lymphatic and chronic myeloid leukaemia, and bone tumours such as osteosarcoma and all types of glioma such as oligodendroglioma and glioblastoma.

Preferential mention should also be made of the prevention and treatment of diseases of the peripheral or central nervous system. Examples of these include depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

Particularly preferably the present invention relates to the use of compounds of formula 1 for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, idiopathic pulmonary fibrosis, fibrosing alveolitis, COPD, chronic bronchitis, chronic sinusitis, asthma, Crohn's disease, ulcerative colitis, particularly COPD, chronic bronchitis and asthma.

It is most preferable to use the compounds of formula 1 for the treatment of inflammatory and obstructive diseases such as COPD, chronic bronchitis, chronic sinusitis, asthma, Crohn's disease, ulcerative colitis, particularly COPD, chronic bronchitis and asthma.

It is also preferable to use the compounds of formula 1 for the treatment of diseases of the peripheral or central nervous system such as depression, bipolar or manic depression, acute and chronic anxiety states, schizophrenia, Alzheimer's disease, Parkinson's disease, acute and chronic multiple sclerosis or acute and chronic pain as well as injuries to the brain caused by stroke, hypoxia or craniocerebral trauma.

An outstanding aspect of the present invention is the reduced profile of side effects. This means, within the scope of the invention, being able to administer a dose of a pharmaceutical composition without inducing vomiting, preferably nausea and most preferably malaise in the patient. It is particularly preferable to be able to administer a therapeutically effective quantity of substance without inducing emesis or nausea, at every stage of the disease.

Combinations

The compounds of formula 1 may be used on their own or in conjunction with other active substances of formula 1 according to the invention. If desired the compounds of formula 1 may also be used in combination with other pharmacologically active substances. It is preferable to use for this purpose active substances selected for example from among betamimetics, anticholinergics, corticosteroids, other PDE4-inhibitors, LTD4-antagonists, EGFR-inhibitors, MRP4-inhibitors, dopamine agonists, H1-antihistamines, PAF-antagonists and PI3-kinase inhibitors or double or triple combinations thereof, such as for example combinations of compounds of formula 1 with one or two compounds selected from among betamimetics, corticosteroids, PDE4-inhibitors, EGFR-inhibitors and LTD4-antagonists, anticholinergics, betamimetics, corticosteroids, PDE4-inhibitors, EGFR-inhibitors and LTD4-antagonists, PDE4-inhibitors, corticosteroids, EGFR-inhibitors and LTD4-antagonists EGFR-inhibitors, PDE4-inhibitors and LTD4-antagonists EGFR-inhibitors and LTD4-antagonists, CCR3-inhibitors, iNOS-inhibitors (inducible nitric oxide synthase inhibitors), (6R)-L-erythro-5,6,7,8-tetrahydrobiopterin (hereinafter referred to as "BH4") and the derivatives thereof as mentioned in WO 2006/120176 and SYK-inhibitors (spleen tyrosine kinase-inhibitors)

anticholinergics, betamimetics, corticosteroids, PDE4-inhibitors and MRP4-inhibitors.

The invention also encompasses combinations of three active substances, each selected from one of the above-mentioned categories of compounds.

Suitable betamimetics used are preferably compounds selected from among albuterol, bambuterol, bitolterol, broxaterol, carbuterol, clenbuterol, fenoterol, formoterol, arformoterol, zinterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5.6-diethyl-indan-2-ylamino)-1-hydroxy-ethyl]-8-hydroxy-1H-quinolin-2-one, 4-hydroxy-7-[2-{[2-{[3-(2-phenylethoxy)propyl] sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo- 4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3.4-dihydro-2H-benzo[1,4]oxazin-8-yl)-ethylamino]-2-methyl-propyl}-phenoxy)-butyric acid, 8-{2-[2-(3.4-difluoro-phenyl)-1,1-dimethyl-ethylamino]-1-hydroxy-ethyl}-6-hydroxy-4H-benzo[1,4]oxazin-3-one and 1-(4-ethoxy-carbonylamino-3-cyano-5-fluorophenyl)-2-(tert.-butylamino)ethanol, optionally in the form of the racemates, enantiomers, diastereomers and optionally in the form of the pharmacologically acceptable acid addition salts, solvates or hydrates thereof.

Preferably the betamimetics are selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-hydroxy-2-(4-hydroxy-3-hydroxymethyl-phenyl)-ethylamino]-hexyloxy}-butyl)-benzenesulphonamide, 5-[2-(5.6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl-4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1.1 dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxycarbonylamino-3-cyano-5-fluorophenyl)-2-(tert.-butylamino)ethanol, optionally in the form of the racemates, enantiomers, diastereomers and optionally in the form of the pharmacologically acceptable acid addition salts, solvates or hydrates thereof.

Particularly preferred betamimetics are selected from among fenoterol, formoterol, salmeterol, 3-(4-{6-[2-hydroxy-2-(4-hydroxy-3-hydroxymethyl-phenyl)-ethylamino]-hexyloxy}-butyl)-benzenesulphonamide, 5-[2-(5.6-diethyl-indan-2-ylamino)-1-hydroxy-ethyl]-8-hydroxy-1H-quinoline-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, enantiomers, diastereomers and optionally in the form of the pharmacologically acceptable acid addition salts, solvates or hydrates thereof.

Of these betamimetics the particularly preferred ones according to the invention are formoterol, salmeterol, 3-(4-{6-[2-hydroxy-2-(4-hydroxy-3-hydroxymethyl-phenyl)-ethylamino]-hexyloxy}-butyl)-benzenesulphonamide, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3- one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1.1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 5-[2-(5,6-diethyl-indan-2-ylamino)-1-hydroxy-ethyl]-8-hydroxy-1H-quinoline-2-one, optionally in the form of the racemates, enantiomers, diastereomers and optionally in the form of the pharmacologically acceptable acid addition salts, solvates or hydrates thereof.

According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among the tiotropium salts, oxitropium salts, flutropium salts, ipratropium salts, glycopyrronium salts, trospium salts, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, -scopine 3,3'-difluorobenzilate methobromide, tropenol 9-hydroxy-fluorene-9-carboxylate-methobromide, tropenol 9-fluoro-fluorene-9-carboxylate-methobromide, scopine 9-hydroxy-fluoren-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, -cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl cyclopropyltropine 4,4'-difluorobenzilate methobromide, tropenol 9-hydroxy-xanthene-9-carboxylate-methobromide, -scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide, optionally in the form of the solvates or hydrates thereof.

In the above-mentioned salts the cations tiotropium, oxitropium, flutropium, ipratropium, glycopyrronium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among prednisolone, prednisone, butixocortpropionate, flunisolide, beclomethasone, triamcinolone, budesonide, fluticasone, mometasone, ciclesonide, rofleponide, dexamethasone, betamethasone, deflazacort, RPR-106541, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among flunisolide, beclomethasone, triamcinolone, budesonide, fluticasone, mometasone, ciclesonide, rofleponide, dexamethasone, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulfobenzoates, phosphates, isonicotinates, acetates, propionates, dihydrogen phosphates, palmitates, pivalates or furoates thereof.

Other PDE4 inhibitors which may be used are preferably compounds selected from among enprofyllin, theophyllin, roflumilast, ariflo (cilomilast), tofimilast, pumafentrin, lirimilast, arofyllin, atizoram, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370, N-(3,5-dichloro-1-oxo-pyridin-4-yl)-4-difluoromethoxy-3-cyclopropyl-methoxybenzamide, (−)p-[(4aR*.10bS*)-9-ethoxy-1,2,3,4, 4a, 10b-hexahydro-8-methoxy-2-methylbenzo[s][1.6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferably the PDE4-inhibitor is selected from among enprofyllin, roflumilast, ariflo (cilomilast), arofyllin, atizoram, AWD-12-281 (GW-842470), T-440, T-2585, PD-168787, V-11294A, CI-1018, CDC-801, D-22888, YM-58997, Z-15370, N-(3,5-dichloro-1-oxo-pyridin-4-yl)-4-difluoromethoxy-3-cyclopropyl methoxy-benzamide, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferably the PDE4-inhibitor is selected from among roflumilast, ariflo (cilomilast), arofyllin, AWD-12-281 (GW-842470), 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], atizoram, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2.3-dichlorothieno[3,2-b]pyridin-5-yl)-(E)-ethenyl)phenyl)-3-(2-(1-hydroxy-1-methylethyl)phenyl)propyl)thio)methyl)cyclo-propane-acetic acid and [2-[[2-(4-tert-butyl-2-thiazolyl)-5-benzofuranyl]oxymethyl]phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

Preferably the LTD4-antagonist is selected from among montelukast, pranlukast, zafirlukast, MCC-847 (ZD-3523), MN-001, MEN-91507 (LM-1507), VUF-5078, VUF-K-8707 and L-733321, optionally in the form of the racemates, enantiomers or diastereomers, optionally in the form of the pharmacologically acceptable acid addition salts and optionally in the form of the salts and derivatives, solvates and/or hydrates thereof.

Particularly preferably the LTD4-antagonist is selected from among montelukast, to pranlukast, zafirlukast, MCC-847 (ZD-3523), MN-001 and MEN-91507 (LM-1507), optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({-4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1- oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]cyclohexan-1-yloxy}-7-methoxy-quinazoline, 4-[(3-ethynyl-phenyl)amino]-6-(piperidin- 4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, cetuximab, trastuzumab, ABX-EGF and Mab ICR-62, optionally in the form of the racemates, enantiomers or diastereomers thereof, optionally in the form of the pharmacologically acceptable acid addition salts thereof, the solvates and/or hydrates thereof.

Preferred EGFR-inhibitors are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({-4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({-4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({-4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and cetuximab, optionally in the form of the racemates, enantiomers or diastereomers thereof, optionally in the form of the pharmacologically acceptable acid addition salts thereof, the solvates and/or hydrates thereof.

It is particularly preferable within the scope of the present invention to use those EGFR-inhibitors which are selected from among 4-[(3-chloro-4-fluorophenyl)amino]-6-{4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]

amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxy-ethyl)carbonyl]-piperidin-4-yloxy}-7-methoxy-quinazoline, optionally in the form of the racemates, enantiomers or diastereomers thereof, optionally in the form of the pharmacologically acceptable acid addition salts thereof, the solvates and/or hydrates thereof.

Particularly preferred EGFR-inhibitors according to the invention are the compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluoro-phenyl)amino]-6-{([4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-ethynyl-phenyl)amino]-6,7-bis-(2-methoxy-ethoxy)-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans- 4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline and 4-[(3-chloro-4-fluoro-phenyl)amino]-6-(1-cyano-piperidin-4-yloxy)-7-methoxy-quinazoline, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, nnethanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepines.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-beta-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, clycolithocholic acid sulphate, ibuprofen, indomethacin, indoprofen, ketoprofen, lithocholic acid sulphate, methotrexate, MK571 ((E)-3-[[[3-[2-(7-chloro-2-quinolinyl)ethenyl]phenyl]-[[3-dimethylamino)-3-oxopropyl]thio]methyl]thio]-propanoic acid), alpha-naphthyl-beta-D-glucuronide, nitrobenzyl mercaptopurine riboside, probenecid, PSC833, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

Preferably the invention relates to the use of MRP4-inhibitors for preparing a pharmaceutical composition for the treatment of respiratory complaints, containing the PDE4B-inhibitors and MRP4-inhibitors, the MRP4-inhibitors preferably being selected from among N-acetyl-dinitrophenyl-cysteine, dehydroepiandrosterone 3-sulphate, dilazep, dinitrophenyl-S-glutathione, estradiol 3,17-disulphate, flurbiprofen, glycocholate, glycolithocholic acid sulphate, ibuprofen, indomethacin, indoprofen, lithocholic acid sulphate, MK571, PSC833, sildenafil, taurochenodeoxycholate, taurocholate, taurolithocholate, taurolithocholic acid sulphate, trequinsin and zaprinast, dipyridamole, optionally in the form of the racemates, enantiomers, diastereomers and the pharmacologically acceptable acid addition salts and hydrates thereof.

The invention relates more preferably to the use of MRP4-inhibitors for preparing a pharmaceutical composition for treating respiratory complaints, containing the PDE4B-inhibitors and MRP4-inhibitors according to the invention, the MRP4-inhibitors preferably being selected from among dehydroepiandrosterone 3-sulphate, estradiol 3,17-disulphate, flurbiprofen, indomethacin, indoprofen, MK571, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the PDE4B-inhibitors, MRP4-inhibitors and another active substance according to the invention, such as, for example, an anticholinergic, a steroid, an LTD4-antagonist or a betamimetic, and the preparation thereof and the use thereof for treating respiratory complaints.

The iNOS-inhibitors used are preferably compounds selected from among: S-(2-aminoethyl)isothiourea, aminoguanidine, 2-aminomethylpyridine, AMT, L-canavanine, 2-iminopiperidine, S-isopropylisothiourea, S-methylisothiourea, S-ethylisothiourea, S-methyltiocitrulline, S-ethylthiocitrulline, L-NA ($N^\omega$-nitro-L-arginine), L-NAME ($N^\omega$-nitro-L-arginine methylester), L-NMMA ($N^G$-monomethyl-L-arginine), L-NIO ($N^\omega$-iminoethyl-L-ornithine), L-NIL ($N^\omega$-iminoethyl-lysine), (S)-6-acetimidoylamino-2-aminohexanoic acid (1H-tetrazol-5-yl)-amide (SC-51) (*J. Med. Chem.* 2002, 45, 1686-1689), 1400W, (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-

3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-trifluoromethyl-nicotinonitrile (WO 2004/041794), 2-((1R,3S)-3-amino-4-hydroxy-1-thiazol-5-yl-butylsulphanyl)-4-chloro-benzonitrile (WO 2004/041794), 2-((1R,3S)-3-amino-4-hydroxy-1-thiazol-5-yl-butylsulphanyl)-5-chloro-benzonitrile (WO 2004/041794), (2S.4R)-2-amino-4-(2-chloro-5-trifluoromethyl-phenylsulphanyl)-4-thiazol-5-yl-butan-1-ol (WO 2004/041794), 2-((1R,3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamine such as e.g. AR-C102222 (*J. Med. Chem.* 2003, 46, 913-916), (1S,5S,6R)-7-chloro-5-methyl-2-aza-bicyclo[4.1.0]hept-2-en-3-ylamine (ONO-1714) (*Biochem. Biophys. Res. Commun.* 2000, 270, 663-667), (4R,5R)-5-ethyl-4-methyl-thiazolidin-2-ylideneamine (*Bioorg. Med. Chem.* 2004, 12, 4101), (4R,5R)-5-ethyl-4-methyl-selenazolidin-2-ylideneamine (*Bioorg. Med. Chem. Lett.* 2005, 15, 1361), 4-aminotetrahydrobiopterin (*Curr. Drug Metabol.* 2002, 3, 119-121), (E)-3-(4-chloro-phenyl)-N-(1-{2-oxo-2-[4-(6-trifluoromethyl-pyrimidin-4-yloxy)-piperidin-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-ylmethyl-phenoxy)-ethoxy]-2-phenyl-pyridine (PPA250) (*J. Pharmacol. Exp. Ther.* 2002, 303, 52-57), methyl 3-{[(benzo[1,3]dioxol-5-yl-methyl)-carbamoyl]-methyl}-4-(2-imidazol-1-yl-pyrimidin-4-yl)-piperazine-1-carboxylate (BBS-1) (*Drugs Future* 2004, 29, 45-52), (R)-1-(2-imidazol-1-yl-6-methyl-pyrimidin-4-yl)-pyrrolidin-2-carboxylic acid (2-benzo[1,3]dioxol-5-yl-ethyl)-amide (BBS-2) (*Drugs Future* 2004, 29, 45-52) and the pharmaceutical salts, prodrugs or solvates thereof.

Other iNOS-inhibitors that may be used within the scope of the present invention are antisense oligonucleotides, particularly those antisense oligonucleotides that bind iNOS-coding nucleic acids. For example, WO 01/52902 describes antisense oligonucleotides, particularly antisense oligonucleotides that bind iNOS coding nucleic acids, for modulating the expression of iNOS. INOS antisense oligonucleotides of this kind, as described in particular in WO 01/52902 may therefore also be combined with the PDE4-inhibitors of the present invention on the basis of their similarity of activity to that of the iNOS inhibitors.

The SYK-inhibitors used are preferably compounds selected from among: 2-[(2-aminoethyl)amino]-4-[(3-bromophenyl)amino]-5-pyrimidinecarboxamide;
2-[[7-(3,4-dimethoxyphenyl)imidazo[1,2-c]pyrimidin-5-yl]amino]-3-pyridinecarboxamide;
6-[[5-fluoro-2-[3,4,5-trimethoxyphenyl)amino]-4-pyrimidinyl]amino]-2,2-dimethyl-2H-pyrido[3,2-b]-1,4-oxazin-3(4H)-one;
N-[3-bromo-7-(4-methoxyphenyl)-1,6-naphthyridin-5-yl]-1,3-propanediamine
7-(4-methoxyphenyl)-N-methyl-1,6-naphthyridin-5-amine;
N-[7-(4-methoxyphenyl)-1,6-naphthyridin-5-yl]-1,3-propanediamine;
N-[7-(2-thienyl)-1,6-naphthyridin-5-yl-1,3-propanediamine;
N-[7-[4-(dimethylamino)phenyl]-1,6-naphthyridin-5-yl]-1,2-ethanediamine;
N-[7-(4-methoxyphenyl)-2-(trifluoromethyl)-1,6-naphthyridin-5-yl]-1,3-propanediamine;
N-[7-(4-methoxyphenyl)-3-phenyl-1,6-naphthyridin-5-yl]-1,3-propanediamine;
N-(7-phenyl-1,6-naphthyridin-5-yl)-1,3-propanediamine;
N-[7-(3-fluorophenyl)-1,6-naphthyridin-5-yl]-1,3-propanediamine;
N-[7-(3-chlorophenyl)-1,6-naphthyridin-5-yl]-1,3-propanediamine;
N-[7-[3-(trifluoromethoxy)phenyl]-1,6-naphthyridin-5-yl]-1,3-propanediamine;
N-[7-(4-fluorophenyl)-1,6-naphthyridin-5-yl]-1,3-propanediamine;
N-[7-(4-fluorophenyl)-1,6-naphthyridin-5-yl]-1,3-propanediamine;
N-[7-(4-chlorophenyl)-1,6-naphthyridin-5-yl]-1,3-propanediamine;
N-[7-(4'-methyl[1,1'-biphenyl]-4-yl)-1,6-naphthyridin-1,3-propanediamine;
N-[7-[4-(dimethylamino)phenyl]-1,6-naphthyridin-5-yl]-1,3-propanediamine;
N-[7-[4-(diethylamino)phenyl]-1,6-naphthyridin-5-yl]-1,3-propanediamine;
N-[7-[4-(4-morpholinyl)phenyl]-1,6-naphthyridin-5-yl]-1,3-propanediamine;
N-[7-[4-[[2-(dimethylamino)ethyl]methylamino]phenyl]-1,6-naphthyridin-5-yl]-1,3-propanediamine;
N-[7-(4-bromophenyl)-1,6-naphthyridin-5-yl]-1,3-propanediamine;
N-[7-(4-methylphenyl)-1,6-naphthyridin-5-yl]-1,3-propanediamine;
N-[7-[4-(methylthio)phenyl]-1,6-naphthyridin-5-yl]-1,3-propanediamine;
N-[7-[4-(1-methylethyl)phenyl]-1,6-naphthyridin-5-yl]-1,3-propanediamine;
7-[4-(dimethylamino)phenyl]-N-methyl-1,6-naphthyridin-5-amine;
7-[4-(dimethylamino)phenyl]-N,N-dimethyl-1,6-naphthyridin-5-amine;
N-[7-[4-(dimethylamino)phenyl]-1,6-naphthyridin-5-yl]-1,4-butanediamine;
N-[7-[4-(dimethylamino)phenyl]-1,6-naphthyridin-5-yl]-1,5-pentanediamine;
3-[[7-[4-(dimethylamino)phenyl]-1,6-naphthyridin-5-yl]oxy]-1-propanol;
4-[5-(4-aminobutoxy)-1,6-naphthyridin-7-yl]-N,N-dimethyl-benzenamine;
4-[[7-[4-(dimethylamino)phenyl]-1,6-naphthyridin-5-yl]amino]-1-butanol;
N-[7-[4-(dimethylamino)phenyl]-1,6-naphthyridin-5-yl]-N-methyl-1,3-propanediamine;
N-[7-[4-(dimethylamino)phenyl]-1,6-naphthyridin-5-yl]-N'-methyl-1,3-propanediamine;
N-[7-[4-(dimethylamino)phenyl]-1,6-naphthyridin-5-yl]-N,N'-dimethyl-1,3-propanediamine;
1-amino-3-[[7-[4-(dimethylamino)phenyl]-1,6-naphthyridin-5-yl]amino]-2-propanol;
N-[7-[4-(dimethylamino)phenyl]-1,6-naphthyridin-5-yl]-2,2-dimethyl-1,3-propanediamine;
7-[4-(dimethylamino)phenyl]-N-(3-pyridinylmethyl)-1,6-naphthyridin-5-amine;
N-[(2-aminophenyl)methyl]-7-[4-(dimethylamino)phenyl]-1,6-naphthyridin-5-amine;
N-[7-[6-(dimethylamino)[1,1'-biphenyl]-3-yl]-1,6-naphthyridin-5-yl]-1,3-propanediamine,
N-[7-[3-chloro-4-(diethylamino)phenyl]-1,6-naphthyridin-5-yl]-1,3-propanediamine;
N-[7-[4-(dimethylamino)-3-methoxyphenyl]-1,6-naphthyridin-5-yl]-1,3-propanediamine;
N-[7-[4-(diethylamino)phenyl]-3-methyl-1,6-naphthyridin-5-yl]-1,3-propanediamine;

N-[7-(3'-fluoro[1,1-biphenyl]-3-yl)-1,6-naphthyridin-5-yl]-1,2-ethanediamine,
N-[7-(4-methoxyphenyl)-1,6-naphthyridin-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridin-5-yl]-1,6-naphthyridine-1,3-propanediamine;
N5-(3-aminopropyl)-7-(4-methoxyphenyl)-N2-(phenylmethyl)-2,5-diamine;
N-[7-(2-naphthalenyl)-1,6-naphthyridin-5-yl]-1,3-propanediamine;
N-[7-(2'-fluoro[1,1'-biphenyl]-4-yl)-1,6-naphthyridin-5-yl]-1,3-propanediamine;
N-[7-(3,4,5-trimethoxyphenyl)-1,6-naphthyridin-5-yl]-1,3-propanediamine;
N-[7-(3,4-dimethylphenyl)-1,6-naphthyridin-5-yl]-1,3-propanediamine;
1-amino-3-[[7-(2-naphthalenyl)-1,6-naphthyridin-5-yl]amino]-2-propanol;
1-amino-3-[[7-(2'-fluoro[1,1'-biphenyl]-4-yl)-1,6-naphthyridin-5-yl]amino]-2-propanol;
1-amino-3-[[7-(4'-methoxy[1,1'-biphenyl]-4-yl)-1,6-naphthyridin-5-yl]amino]-2-propanol;
1-amino-3-[[7-(3,4,5-trimethoxyphenyl)-1,6-naphthyridin-5-yl]amino]-2-propanol;
1-amino-3-[[7-(4-bromophenyl)-1,6-naphthyridin-5-yl]amino]-2-propanol;
N-[7-(4'-methoxy[1,1'-biphenyl]-4-yl)-1,6-naphthyridin-5-yl]-2,2-dimethyl-1,3-propanediamine;
1-[[7-[4-(dimethylamino)phenyl]-1,6-naphthyridin-5-yl]amino]-2-propanol;
2-[[2-[[7-[4-(dimethylamino)phenyl]-1,6-naphthyridin-5-yl]amino]ethyl]thio]-ethanol;
7-[4-(dimethylamino)phenyl]-N-(3-methyl-5-isoxazolyl)-1,6-naphthyridin-5-amine;
7-[4-(dimethylamino)phenyl]-N-4-pyrimidinyl-1,6-naphthyridin-5-amine;
N-[7-[4-(dimethylamino)phenyl]-1,6-naphthyridin-5-yl]-1,3-cyclohexanediamine;
N,N-dimethyl-4-[5-(1-piperazinyl)-1,6-naphthyridin-7-yl]-benzenamine;
4-[5-(2-methoxyethoxy)-1,6-naphthyridin-7-yl]N,N-dimethyl-benzenamine;
1-[7-[4-(dimethylamino)phenyl]-1,6-naphthyridin-5-yl]-4-piperidinol;
1-[7-[4-(dimethylamino)phenyl]-1,6-naphthyridin-5-yl]-3-pyrrolidinol;
7-[4-(dimethylamino)phenyl]-N-(2-furanylmethyl)-1,6-naphthyridin-5-amine;
7-[4-(dimethylamino)phenyl]-N-[3-(1H-imidazol-1-yl)-propyl]-1,6-naphthyridin-5-amine;
1-[7-[4-(dimethylamino)phenyl]-1,6-naphthyridin-5-yl]-4-piperidinecarboxamide;
1-[3-[[7-[4-(dimethylamino)phenyl]-1,6-naphthyridin-5-yl]amino]propyl]-2-pyrrolidinone;
N-[3'-[5-[(3-aminopropyl)amino]-1,6-naphthyridin-7-yl][1,1'-biphenyl]-3-yl]-acetamide;
N-[7-(4'-fluoro[1,1'-biphenyl]-4-yl)-1,6-naphthyridin-5-yl]-1,3-propanediamine;
N-[4'-[5-[(3-aminopropyl)amino]-1,6-naphthyridin-7-yl][1,1'-biphenyl]-3-yl]-acetamide;
N-[7-[4-(1,3-benzodioxol-5-yl)phenyl]-1,6-naphthyridin-5-yl]-1,3-propanediamine;
N-[7-[4-(2-thienyl)phenyl]-1,6-naphthyridin-5-yl]-1,3-propanediamine;
N-[7-[4-fluoro-3-(trifluoromethyl)phenyl]-1,6-naphthyridin-5-yl]-1,3-propanediamine;
N-[7-[4-(3-pyridinyl)phenyl]-1,6-naphthyridin-5-yl]-1,3-propanediamine;
N-[7-(1,3-benzodioxol-5-yl)-1,6-naphthyridin-5-yl]-1,3-propanediamine;
N-[7-(6-methoxy-2-naphthalenyl)-1,6-naphthyridin-5-yl]-1,3-propanediamine;
7-[4-(dimethylamino)phenyl]-N-(4-pyridinylmethyl)-1,6-naphthyridin-5-amine;
3-[[7-[4-(dimethylamino)phenyl]-1,6-naphthyridin-5-yl]methylamino]-propanenitrile;
7-[4-(dimethylamino)phenyl]-N-[1-(phenylmethyl)-4-piperidinyl]-1,6-naphthyridin-5-amine;
N-[7-[4-(dimethylamino)phenyl]-1,6-naphthyridin-5-yl]-1,2-cyclohexanediamine,
(1R,2S)-rel-.
N-[7-[4-(dimethylamino)phenyl]-1,6-naphthyridin-5-yl]-1,2-benzenedimethanamine;
N-[7-[4-(diethylamino)phenyl]-1,6-naphthyridin-5-yl]-1,4-butanediamine;
N-[7-[3',5'-bis(trifluoromethyl)[1,1'-biphenyl]-4-yl]-1,6-naphthyridin-5-yl]0.3-propanediamine;
N-[7-(3'-methoxy[1,1'-biphenyl]-4-yl)-1,6-naphthyridin-5-yl]-1,3-propanediamine;
N-[7-(3'-fluoro[1,1'-biphenyl]-4-yl)-1,6-naphthyridin-5-yl]-1,3-propanediamine;
4-[[7-[4-(dimethylamino)phenyl]-1,6-naphthyridin-5-yl]oxy]-1-butanol;
N-[7-[4-(dimethylamino)phenyl]-1,6-naphthyridin-5-yl]-1,4-cyclohexanediamine;
7-[4-(dimethylamino)phenyl]-N-(2,2,6,6-tetramethyl-4-piperidinyl)-1,6-naphthyridin-5-amine;
N-[7-[3-bromo-4-(dimethylamino)phenyl]-1,6-naphthyridin-5-yl]-1,3-propanediamine;
N-[7-(1-methyl-1H-indol-5-yl)-1,6-naphthyridin-5-yl]-1,3-propanediamine;
N-[7-(3-trifluoromethyl)phenyl]-1,6-naphthyridin-5-yl]-1,3-propanediamine;
N-[7-[4-(trifluoromethyl)phenyl]-1,6-naphthyridin-5-yl]-1,3-propanediamine;
N-[7-(3-bromo-4-methoxyphenyl)-1,6-naphthyridin-5-yl]-1,3-propanediamine;
N-[7-[4-[[3-(dimethylamino)propyl]methylamino]phenyl]-1,6-naphthyridin-5-yl]-1,4-cyclohexanediamine;
N-[7-[4-[[2-(dimethylamino)ethyl]methylamino]phenyl]-1,6-naphthyridin-5-yl]-1,4-cyclohexanediamine;
N-[7-[4-(dimethylamino)-3-methoxyphenyl]-1,6-naphthyridin-5-yl]-1,4-cyclohexanediamine;
N-[7-[4-(4-morpholinyl)phenyl]-1,6-naphthyridin-5-yl]-1,4-cyclohexanediamine;
N-[7-[3-bromo-4-(4-morpholinyl)phenyl]-1,6-naphthyridin-5-yl]-1,4-cyclohexanediamine;
4-[[7-[4-[[2-(dimethylamino)ethyl]methylamino]phenyl]-1,6-naphthyridin-5-yl]oxy]-cyclohexanol;
N-[7-[3-bromo-4-(4-morpholinyl)phenyl]-1,6-naphthyridin-5-yl]-1,3-propanediamine;
N,N-dimethyl-4-[5-(4-methyl-1-piperazinyl)-1,6-naphthyridin-7-yl]-benzenamine;
4-[[7-[4-[[3-(dimethylamino)propyl]methylamino]phenyl]-1,6-naphthyridin-5-yl]oxy]-cyclohexanol;
N-[7-[4-[[2-(dimethylamino)ethyl]methylamino]phenyl]-1,6-naphthyridin-5-yl]-1,4-butanediamine;
1,1-dimethylethyl[3-[[5-[(3-aminopropyl)amino]-7-(4-methoxyphenyl)-1,6-naphthyridin-2-yl]amino]propyl]-carbamate.

Formulations

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain the compounds of formula 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, dihydrothienopyrimidine and one or more combination partners selected from those described above.

The invention claimed is:
1. A compound of formula 1

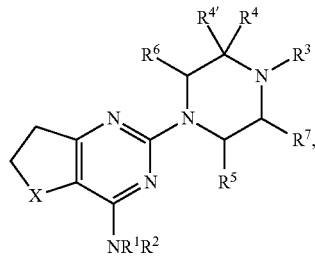

wherein:
X is SO or $SO_2$,
$R^1$ is H or $C_{1-6}$-alkyl, $R^2$ is H or a group selected from $C_{1-10}$-alkyl and $C_{2-6}$-alkenyl, each optionally substituted by one or more groups selected from halogen and $C_{1-3}$-fluoroalkyl or optionally substituted by one or more groups selected from $OR^{2.1}$, $COOR^{2.1}$, $CONR^{2.2}R^{2.3}$, $SR^{2.1}$, $SO-R^{2.1}$, $SO_2-R^{2.1}$, $C_{6-10}$-aryl, a het, a hetaryl, a mono- or bicyclic $C_{3-10}$-cycloalkyl, $CH_2-NR^{2.2}R^{2.3}$, and $NR^{2.2}R^{2.3}$, each optionally substituted by one or more groups selected from OH, halogen, $OR^{2.1}$, oxo, $CF_3$, $CHF_2$, $CH_2F$, $C_{1-6}$-alkyl, $C_{1-6}$-alkanol, $C_{6-10}$-aryl, $COOR^{2.1}$, $CH_2-NR^{2.2}R^{2.3}$, and $NR^{2.2}R^{2.3}$, $R^2$ is a mono- or polycyclic $C_{3-10}$ cycloalkyl optionally mono- or poly-bridged via $C_{1-3}$-alkyl groups and optionally substituted by a group selected from branched or unbranched $C_{1-6}$-alkanol, $C_{1-3}$-fluoroalkyl, $C_{1-3}$-alkylene-$OR^{2.1}$, $OR^{2.1}$, $COOR^{2.1}$, $SO_2-NR^{2.2}R^{2.3}$, het, $C_{6-10}$-aryl, $C_{1-6}$-alkyl, $C_{6-10}$-aryl-$C_{1-6}$-alkylene, hetaryl-$C_{1-6}$-alkylene, mono- or bicyclic $C_{3-10}$ cycloalkyl, and $NR^{2.2}R^{2.3}$, each-optionally substituted by one or more groups selected from OH, $OR^{2.1}$, oxo, halogen, $CF_3$, $CHF_2$, $CH_2F$, $C_{1-6}$-alkyl, $C_{6-10}$-aryl, and $NR^{2.2}R^{2.3}$, $R^2$ is a mono- or polycyclic $C_{6-10}$-aryl optionally substituted by OH, SH, or halogen or by one or more groups selected from $OR^{2.1}$, $COOR^{2.1}$, $NR^{2.2}R^{2.3}$, $CH_2-NR^{2.2}R^{2.3}$, $C_{3-10}$-cycloalkyl, het, $C_{1-6}$-alkyl, $C_{1-3}$-fluoroalkyl, $C_{6-10}$-aryl-$C_{1-6}$-alkylene, het-$C_{1-6}$-alkylene, hetaryl-$C_{1-6}$-alkylene, $C_{6-10}$-aryl, $SO_2-CH_3$, $SO_2-CH_2CH_3$, and $SO_2-NR^{2.2}R^{2.3}$, each optionally substituted by one or more groups selected from OH, $OR^{2.1}$, oxo, halogen, $CF_3$, $CHF_2$, $CH_2F$, $C_{1-6}$-alkyl, $C_{6-10}$-aryl, and $NR^{2.2}R^{2.3}$, $R^2$ is a group selected from a het and a hetaryl, each optionally substituted by one or more groups selected from halogen, OH, oxo, $CF_3$, $CHF_2$, and $CH_2F$ or by one or more groups selected from $OR^{2.1}$, $C_{1-3}$-alkylene-$OR^{2.1}$, $SR^{2.1}$, $SO-R^{2.1}$, $SO_2-R^{2.1}$, $COOR^{2.1}$, $COR^{2.1}$, $C_{1-6}$-alkanol, $C_{3-10}$-cycloalkyl, $C_{6-10}$-aryl, $C_{1-6}$-alkyl, $C_{6-10}$-aryl-$C_{1-6}$-alkylene, hetaryl-$C_{1-6}$-alkylene, het, hetaryl, $C_{1-3}$-alkylene-$OR^{2.1}$, and $NR^{2.2}R^{2.3}$, each optionally substituted by one or more groups selected from OH, $OR^{2.1}$, oxo, halogen, $CF_3$, $CHF_2$, $CH_2F$, $C_{1-6}$-alkyl, $C_{6-10}$-aryl, and $NR^{2.2}R^{2.3}$, or $NR^1R^2$ together is a heterocyclic four- to seven-membered ring optionally bridged, which contains 1, 2, or 3 heteroatoms selected from N, O, and S and optionally substituted by one or more groups selected from OH, $OR^{2.1}$, $C_{1-3}$-alkylene-$OR^{2.1}$, oxo, halogen, $C_{1-6}$-alkyl, $C_{6-10}$-aryl, $COOR^{2.1}$, $CH_2-NR^{2.2}-COO-R^{2.1}$, $CH_2-NR^{2.2}-CO-R^{2.1}$, $CH_2-NR^{2.2}-CO-CH_2-NR^{2.2}R^{2.3}$, $CH_2-NR^{2.2}-SO_2-C_{1-3}$-alkyl, $CH_2-NR^{2.2}-SO_2-NR^{2.2}R^{2.3}$, $CH_2-NR^{2.2}-CO-NR^{2.2}R^{2.3}$, $CO-NR^{2.2}R^{2.3}$, $CH_2-NR^{2.2}R^{2.3}$, and $NR^{2.2}R^{2.3}$, $R^3$ is a group selected from a mono- or bicyclic $C_{6-10}$-aryl, a het, and a hetaryl, each optionally substituted by one or more groups selected from halogen, —$C_{1-3}$-alkyl, cyclopropyl, —$C_{1-3}$-fluoroalkyl, —$C_{1-3}$-alkylene-$OR^{2.1}$, —OH, and —O—$C_{1-3}$-alkyl, $R^4$ is H, $C_{1-6}$-alkyl, F, $C_{1-3}$-fluoroalkyl, ($C_{1-6}$-alkylene)-OH, ($C_{1-6}$-alkylene)-$OCH_3$, ($C_{1-6}$-alkylene)-$NH_2$, ($C_{1-6}$-alkylene)-NH($C_{1-3}$-alkyl), or ($C_{1-6}$-alkylene)-N($C_{1-3}$-alkyl)$_2$, $R^{4'}$ is H or F, and $R^5$ is H, F, $C_{1-6}$-alkyl, $C_{1-3}$-fluoroalkyl, $C_{1-6}$-alkylene-OH, $C_{1-6}$-alkylene-$OCH_3$, $C_{1-6}$-alkylene-$NH_2$, $C_{1-6}$-alkylene-NH($C_{1-3}$-alkyl), or $C_{1-6}$-alkylene-N($C_{1-3}$-alkyl)$_2$, and $R^6$ and $R^7$ together form a bridge selected from methylene, ethylene, and propylene, each optionally substituted by a group selected from —$CH_3$, —OH, —F, —$CF_3$, —$CHF_2$, —$CH_2F$, —$NH_2$, —$NH(C_{1-3}$-alkyl), —$N(C_{1-3}$-alkyl)$_2$, and O—($C_{1-3}$-alkyl), or $R^7$ is H, F, $C_{1-6}$-alkyl, $C_{1-3}$-fluoroalkyl, $C_{1-6}$-alkylene-OH, $C_{1-6}$-alkylene-OCH$_3$, $C_{1-6}$ alkylene-NH$_2$, $C_{1-6}$-alkylene-NH($C_{1-3}$-alkyl), or $C_{1-6}$-alkylene-N($C_{1-3}$-alkyl)$_2$, and $R^5$ and $R^6$ together form a bridge selected from methylene, ethylene, and propylene, each optionally substituted by a group selected from $CH_3$, —OH, —F, —$CF_3$, —$CHF_2$, —$CH_2F$, —$NH_2$, —$NH(C_{1-3}$-alkyl), —$N(C_{1-3}$-alkyl)$_2$, and OCH$_3$, wherein:

$R^{2.1}$ is H or a group selected from $C_{1-6}$-alkyl, $C_{1-6}$-alkanol, $C_{1-3}$-fluoroalkyl, mono- or bicyclic $C_{3-10}$ cycloalkyl, $C_{6-10}$-aryl-$C_{1-6}$-alkylene, hetaryl-$C_{1-6}$-alkylene, het-$C_{1-6}$-alkylene, $C_{3-10}$-cycloalkyl-$C_{1-6}$-alkylene, a mono- or bicyclic $C_{6-10}$-aryl, a hetaryl, and a het, each optionally substituted by one or more groups selected from OH, O—($C_{1-3}$-alkyl), halogen, $C_{1-6}$-alkyl, and $C_{6-10}$-aryl, $R^{2.2}$ and $R^{2.3}$ are each independently H or a group selected from $C_{1-6}$-alkyl, mono- or bicyclic $C_{3-10}$-cycloalkyl, $C_{6-10}$-aryl-$C_{1-6}$-alkylene, hetaryl-$C_{1-6}$-alkylene, mono- or bicyclic $C_{6-10}$-aryl, a het, a hetaryl, CO—NH$_2$, CO—NH(CH$_3$), CO—N(CH$_3$)$_2$, SO$_2$—($C_{1-2}$-alkyl), CO—$R^{2.1}$, and COOR$^{2.1}$, each optionally substituted by one or more groups selected from OH, halogen, $C_{1-6}$-alkyl, $C_{6-10}$-aryl, and COOR$^{2.1}$, het is a three- to eleven-membered, mono- or bicyclic, saturated or partially saturated, optionally annelated or optionally bridged heterocyclic group, which contains 1, 2, 3, or 4 heteroatoms independently selected from N, S, or O, hetaryl is a five- to ten-membered, mono- or bicyclic, optionally annelated heteroaryl, which contains 1, 2, 3, or 4 heteroatoms independently selected from N, S, or O, and cycloalkyl is saturated or partially saturated,
and the pharmacologically acceptable salts thereof.

2. The compound of formula 1 according to claim 1, wherein:

$R^2$ is a group selected from monocyclic, saturated three-, four-, five-, six- or seven-membered heterocyclic groups with 1, 2, or 3 heteroatoms in each case selected from N, O, and S, each optionally substituted by one or more groups selected from fluorine, OH, CF$_3$, CHF$_2$, CH$_2$F, and oxo or by one or more groups selected from OR$^{2.1}$, $C_{1-3}$-alkylene-OR$^{2.1}$, SR$^{2.1}$, SO—R$^{2.1}$, SO$_2$—R$^{2.1}$, COOR$^{2.1}$, COR$^{2.1}$, $C_{1-6}$-alkanol, $C_{3-10}$-cycloalkyl, phenyl, $C_{1-6}$-alkyl, phenyl-$C_{1-6}$-alkylene, hetaryl-$C_{1-6}$-alkylene, het, hetaryl, and NR$^{2.2}$R$^{2.3}$, each optionally substituted by one or more groups selected from OH, OR$^{2.1}$, oxo, F, Cl, CF$_3$, CHF$_2$, CH$_2$F, $C_{1-6}$-alkyl, phenyl, and NR$^{2.2}$R$^{2.3}$, and the pharmacologically acceptable salts thereof.

3. The compound of formula 1 according to claim 2, wherein:

$R^2$ is a group selected from a monocyclic, saturated six-membered heterocyclic group with at least one heteroatom selected in each case from N, O, and S, each optionally substituted by one or more groups selected from F, CF$_3$, CHF$_2$, CH$_2$F, OH, oxo, NH$_2$, NHCH$_3$, N(CH$_3$)$_2$, methyl, ethyl, propyl, isopropyl, cyclopropyl, methoxy, and ethoxy, and the pharmacologically acceptable salts thereof.

4. The compound of formula 1 according to claim 3, wherein:

$R^2$ is a group selected from piperidine or tetrahydropyran, each optionally substituted by one or more groups selected from F, OH, CF$_3$, CHF$_2$, CH$_2$F, NH$_2$, NHCH$_3$, N(CH$_3$)$_2$, oxo, methyl, and methoxy, and the pharmacologically acceptable salts thereof.

5. The compound of formula 1 according to claim 1, wherein:

$R^3$ is a group selected from the group comprising a phenyl optionally substituted by one or more groups selected from F, Cl, Br, methyl, ethyl, propyl, isopropyl, cyclopropyl, $C_{1-3}$-fluoroalkyl, $C_{1-3}$-alkanol, OH, and O—$C_{1-3}$-alkyl, and the pharmacologically acceptable salts thereof.

6. The compound of formula 1 according to claim 1, wherein:

$R^4$ is H or methyl, and
$R^{4'}$ is H and the pharmacologically acceptable salts thereof.

7. The compound of formula 1 according to claim 1, wherein:

$R^6$ and $R^7$ together form a bridge selected from among methylene and ethylene, or wherein
$R^5$ and $R^6$ together form a bridge selected from among methylene and ethylene, and the pharmacologically acceptable salts thereof.

8. The compound of formula 1 according to claim 1, wherein the compound is selected from:

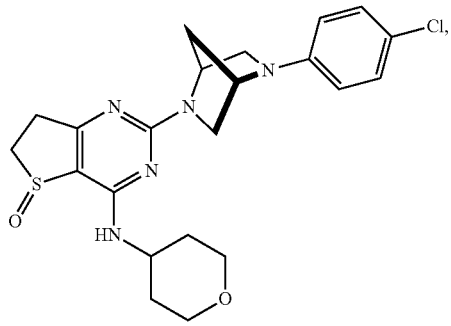

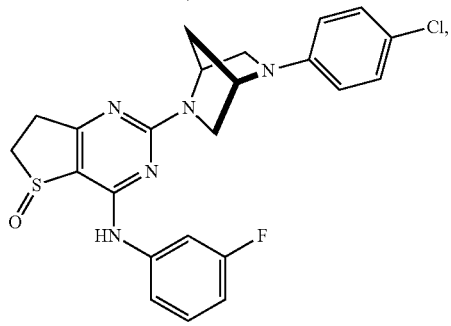

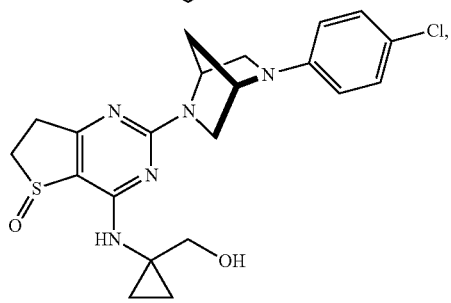

133
-continued
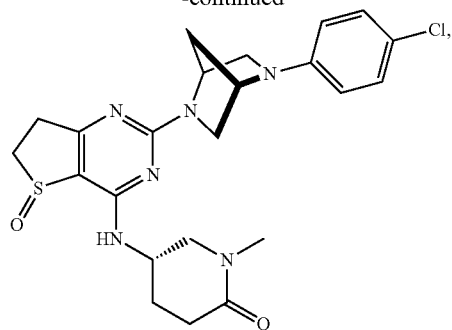
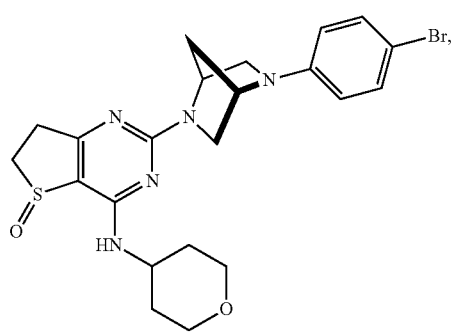
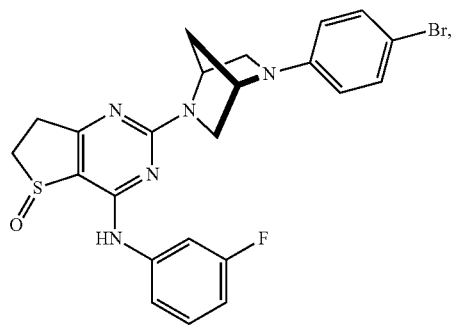
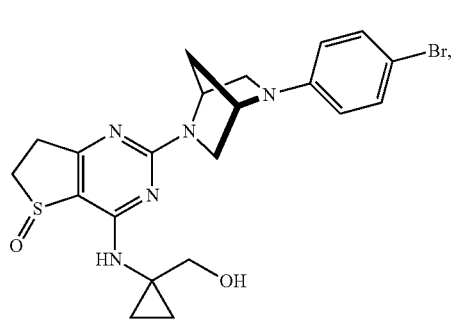
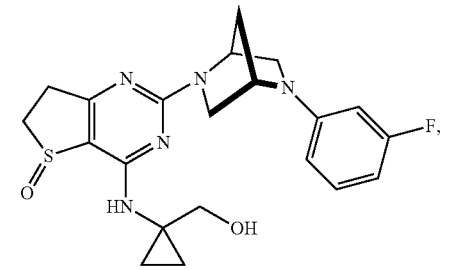
134
-continued
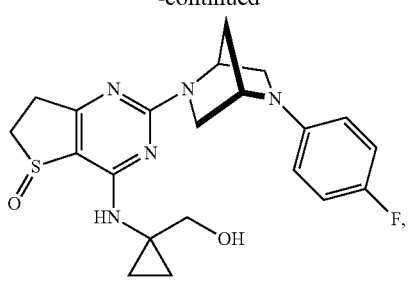
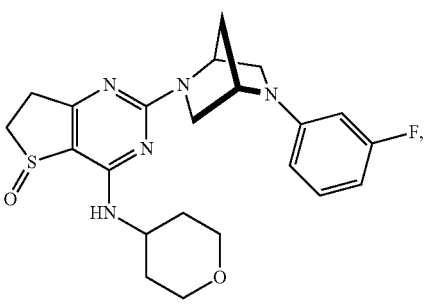
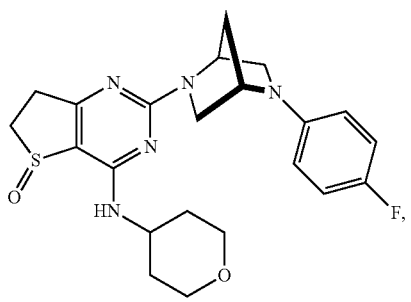
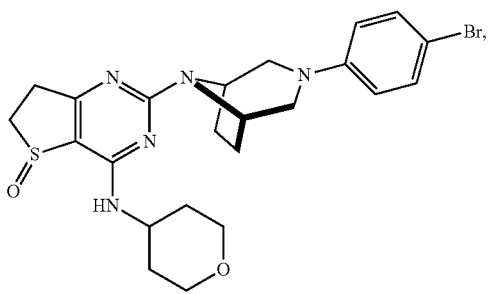
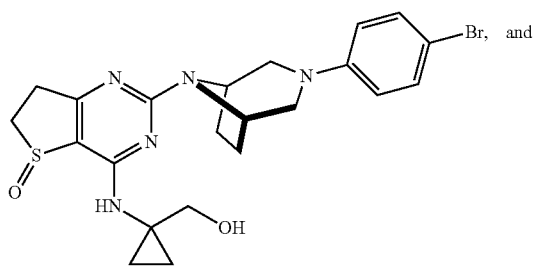

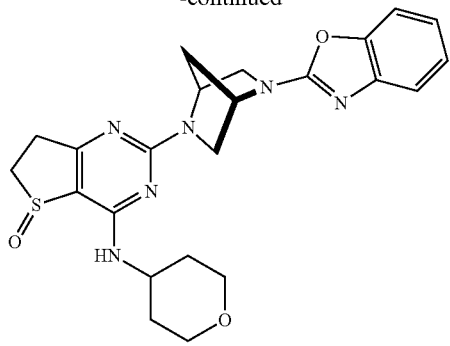

and the pharmacologically acceptable salts thereof.

9. A pharmaceutical formulation comprising a compound of formula 1 according to claim 1 and a pharmaceutical excipient.

10. A pharmaceutical formulation comprising a compound of formula 1 according to claim 1 and an active substance selected from betamimetics, corticosteroids, other phophodiesterase 4 inhibitors (PDE4-inhibitors), growth factor receptor inhibitors (EGFR-inhibitors) and leukotriene D4-antagonist (LTD4-antagonists), chemokine receptor 3-inhibitors (CCR3-inhibitors), inducible nitric oxide synthase inhibitors (iNOS-inhibitors), and spleen tyrosine kinase inhibitors (SYK-inhibitors).

* * * * *